(12) United States Patent
Childers et al.

(10) Patent No.: US 9,895,426 B2
(45) Date of Patent: *Feb. 20, 2018

(54) SYSTEMIC GENE REPLACEMENT THERAPY FOR TREATMENT OF X-LINKED MYOTUBULAR MYOPATHY (XLMTM)

(71) Applicants: Wake Forest University Health Sciences, Winston-Salem, NC (US); Genethon, Evry (FR); Children's Medical Center Corporation, Boston, MA (US)

(72) Inventors: Martin K. Childers, Seattle, WA (US); Alan H. Beggs, Needham, MA (US); Ana Maria Buj Bello, Paris (FR)

(73) Assignees: Wake Forest University Health Sciences, Winston-Salem, NC (US); Genethon, Evry (FR); Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/384,976

(22) Filed: Dec. 20, 2016

(65) Prior Publication Data

US 2017/0112905 A1 Apr. 27, 2017

Related U.S. Application Data

(63) Continuation of application No. 15/220,139, filed on Jul. 26, 2016, which is a continuation of application No. 14/595,540, filed on Jan. 13, 2015, now Pat. No. 9,415,120, which is a continuation of application No. 14/194,186, filed on Feb. 28, 2014, now Pat. No. 8,957,044.

(60) Provisional application No. 61/771,449, filed on Mar. 1, 2013.

(51) Int. Cl.
*A61K 48/00* (2006.01)
*A61K 38/46* (2006.01)
*C12N 7/00* (2006.01)
*C07H 21/00* (2006.01)
*C07H 21/04* (2006.01)
*C12N 15/00* (2006.01)
*C12N 15/85* (2006.01)
*C12P 21/06* (2006.01)

(52) U.S. Cl.
CPC ........ *A61K 38/465* (2013.01); *A61K 48/0058* (2013.01); *C12N 7/00* (2013.01); *C12Y 301/03* (2013.01); *C12Y 301/03064* (2013.01); *C12N 2750/14143* (2013.01)

(58) Field of Classification Search
None
See application file for complete search history.

(56) References Cited

U.S. PATENT DOCUMENTS

| | | |
|---|---|---|
| 4,962,091 A | 10/1990 | Eppstein et al. |
| 5,350,674 A | 9/1994 | Boenisch et al. |
| 5,399,346 A | 3/1995 | Anderson et al. |
| 5,478,745 A | 12/1995 | Samulski et al. |
| 5,580,859 A | 12/1996 | Felgner et al. |
| 5,585,362 A | 12/1996 | Wilson et al. |
| 5,589,466 A | 12/1996 | Felgner et al. |
| 6,156,303 A | 12/2000 | Russell et al. |
| 6,326,193 B1 | 12/2001 | Liu et al. |
| 7,282,199 B2 | 10/2007 | Gao et al. |
| 8,957,044 B2 | 2/2015 | Childers et al. |
| 9,415,120 B2 | 8/2016 | Childers et al. |
| 2017/0095540 A1* | 4/2017 | Childers .............. A61K 38/465 |

FOREIGN PATENT DOCUMENTS

| | | |
|---|---|---|
| WO | 9407529 A1 | 4/1994 |
| WO | 0129058 A1 | 4/2001 |
| WO | 0196584 A2 | 12/2001 |
| WO | 03042397 A2 | 5/2003 |
| WO | 2005033321 A2 | 4/2005 |
| WO | 2010148010 A1 | 12/2010 |

OTHER PUBLICATIONS

Grieger, et al., "Adeno-associated virus vectorology, manufacturing, and clinical applications", Methods Enzymol. 507, 2012, 229-254.
Wang, et al., "The next step in gene delivery: molecular engineering of adeno-associated virus serotypes", J Mol Cell Cardiol. 50(5), 2011, 793-802.
Al-Qusairi, et al., "T-tubule disorganization and defective excitation-contraction coupling in muscle fibers lacking myotubularin lipid phosphataseProc Natl Acad Sci U S A. Nov. 3, 2009;106(44):18763-8", Proc Natl Acad Sci U S A. 106(44), Nov. 2009, 18763-18768.
Arruda, et al., "Peripheral transvenular delivery of adeno-associated viral vectors to skeletal muscle as a novel therapy for hemophilia B", Blood. 115(23), Jun. 2010, 4678-4688.
Beggs, et al., "MTM1 mutation associated with X-linked myotubular myopathy in Labrador Retrievers", Proc Natl Acad Sci U S A. 107(33), Aug. 2010, 14697-14702.
Buj-Bello, et al., "AAV-mediated intramuscular delivery of myotubularin corrects the myotubular myopathy phenotype in targeted murine muscle and suggests a function in plasma membrane homeostasis", Hum Mol Genet.17(14), Jul. 2008, 2132-2143.

(Continued)

*Primary Examiner* — Nancy J Leith
(74) *Attorney, Agent, or Firm* — Saul Ewing Arnstein & Lehr LLP; Kathryn Doyle

(57) ABSTRACT

The present invention provides compositions and methods for treating a myopathy. In certain embodiments, the invention provides compositions and methods for treating, improving muscle function, and prolonging survival in a subject with X-linked myotubular myopathy (XLMTM). The present invention provides a method comprising systemic administration of a composition that induces the increased expression of myotubularin in the muscle of a subject. The invention provides sustained regional and global increases in muscle function.

56 Claims, 32 Drawing Sheets

(56) References Cited

OTHER PUBLICATIONS

Buj-Bello, et al., "The lipid phosphatase myotubularin is essential for skeletal muscle maintenance but not for myogenesis in mic", Proc Natl Acad Sci U S A. 99(23), Nov. 2002, 15060-15065.

Bykhovskaya, et al., "Missense mutation in pseudouridine synthase 1 (PUS1) causes mitochondrial myopathy and sideroblastic anemia (MLASA)", Am J Hum Genet. 74(6), Jun. 2004, 1303-1308.

Childers, et al., "AAV-mediated gene replacement therapy for X-linked myotubular myopathy", Human Gene Therapy 23(10), Oct. 2012, A36.

Childers, et al., "AAV-MTM1 Prolongs survival and resuces severe muscle weakness in mouse and canine models of X-linked myotubular myopathy", Molecular Therapy 20(Supplement 1), May 2012.

Childers, et al., "In vivo canine muscle function assay", J Vis Exp. (50), Apr. 2011.

Daniele, et al., "Delivery of an adeno-associated virus 9 vector encoding MTMR2 corrects targeted muscles in a murine model of myotubular myopathy", Human Gene Therapy 23(10), Oct. 2012, A129.

Eklund, et al., "Lack of type XV collagen causes a skeletal myopathy and cardiovascular defects in mice", Proc Natl Acad Sci U S A. 98(3):, Jan. 2001, 1194-1199.

Fisher, et al., "Transduction with recombinant adeno-associated virus for gene therapy is limited by leading-strand synthesis", J Virol. 70(1), Jan. 1996, 520-532.

Levak-Frank, et al., "Muscle-specific overexpression of lipoprotein lipase causes a severe myopathy characterized by proliferation of mitochondria and peroxisomes in transgenic mice", J Clin Invest. 96(2), Aug. 1995, 976-986.

Qiao, et al., "Hydrodynamic limb vein injection of adeno-associated virus serotype 8 vector carrying canine myostatin propeptide gene into normal dogs enhances muscle growth", Hum Gene Ther. 20(1), Jan. 2009, 1-10.

Tegeler, et al., "Eccentric contractions induce rapid isometric torque drop in dystrophin-deficient dogs", Muscle Nerve. 42(1), Jul. 2010, 130-132.

Ui-Tei, et al., "Sensitive assay of RNA interference in *Drosophila* and Chinese hamster cultured cells using firefly luciferase gene as target", FEBS Lett. 479(3), Aug. 2000, 79-82.

Vorgerd, et al., "A mutation in the dimerization domain of filamin c causes a novel type of autosomal dominant myofibrillar myopathy", Am J Hum Genet. 77(2), Aug. 2005, 297-304.

Wang, et al., "Sustained AAV-mediated dystrophin expression in a canine model of Duchenne muscular dystrophy with a brief course of immunosuppression", Mol Ther. 15(6), Jun. 2007, 1160-1166.

Wu, et al., "Systemic administration of naked DNA with targeting specificity to mammalian kidneys.", Gene Ther. 12(6), Mar. 2005, 477-786.

\* cited by examiner

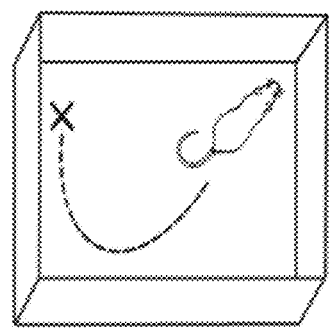
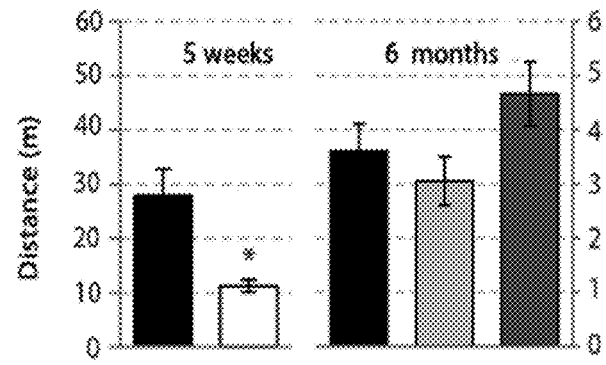
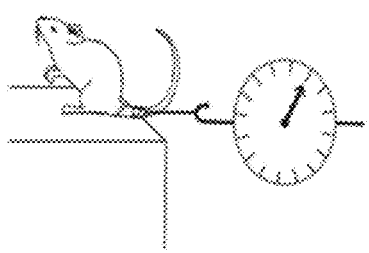
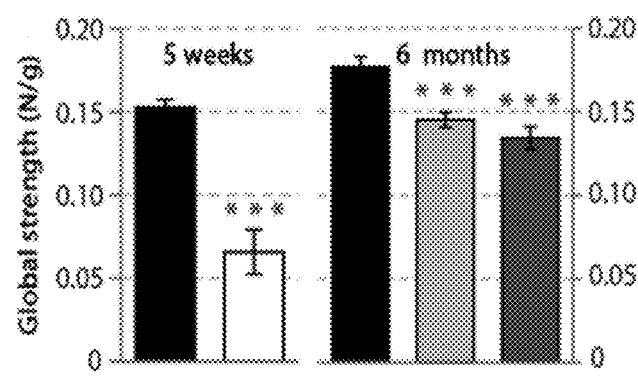
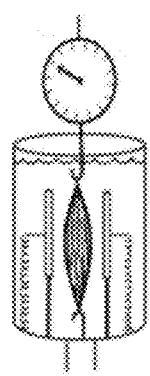
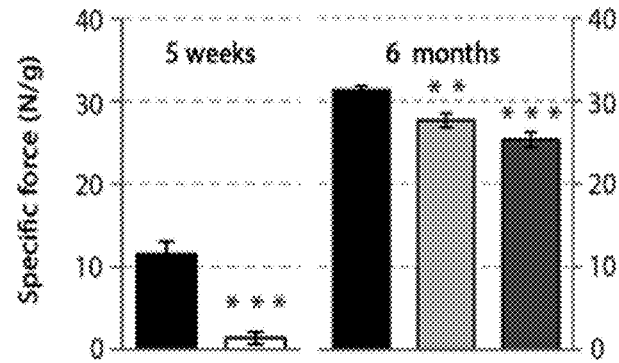
FIGS. 3A-3C

A
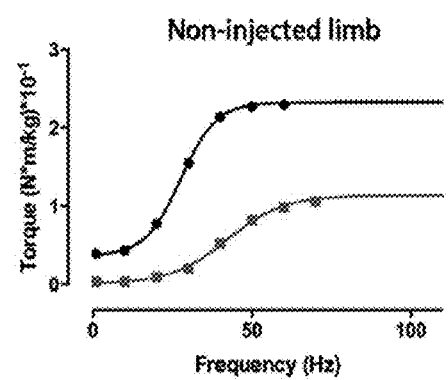
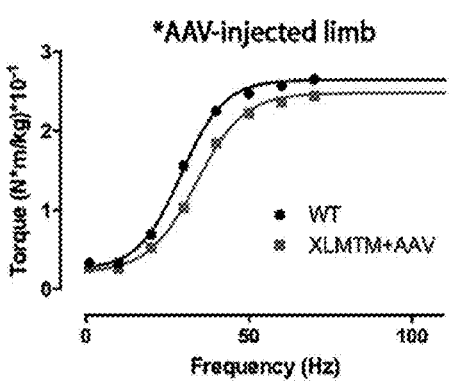
B
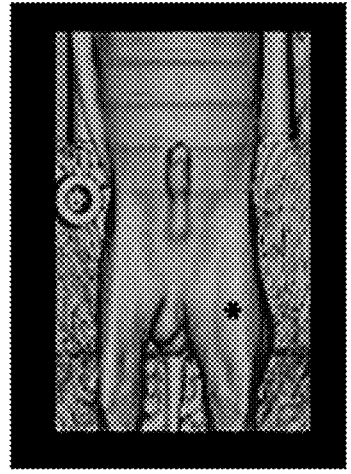
C
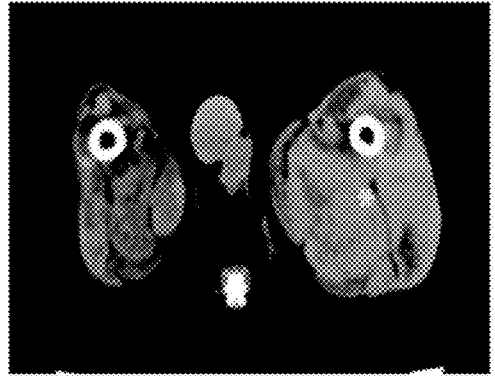
FIGS. 13A-13C

A

B

SEQUENCE LISTING

```
<160> NUMBER OF SEQ ID NOS: 12

<210> SEQ ID NO 1
<211> LENGTH: 1812
<212> TYPE: DNA
<213> ORGANISM: Mus musculus

<400> SEQUENCE: 1
atggcttctg catcagcatc taagtataat tcacactcct tggagaatga atccattaag      60
aaagtgtctc aagatggagt cagtcaggat gtgagtgaga ctgtccctcg gctcccaggg     120
```

-continued

| | |
|---|---|
| gagttactaa ttactgaaaa agaagttatt tacatatgtc ctttcaatgg ccccattaag | 180 |
| ggaagagttt acatcacaaa ttatcgtctt tatttaagaa gtttggaaac ggattctgct | 240 |
| ctaatacttg atgttcctct gggtgtgata tcaagaattg aaaaaatggg aggcgcgaca | 300 |
| agtagaggag aaaattccta tggtctagat attacttgta aagatttgag aaacctgagg | 360 |
| tttgcattga agcaagaagg ccacagcaga agagatatgt tgagatcct tgtaaaacat | 420 |
| gcctttcctc tggcacacaa tctgccatta tttgcatttg taaatgaaga gaagtttaac | 480 |
| gtggatgggt ggactgtta taatccagtt gaagaatata aaggcaggg cctgcccaat | 540 |
| caccattgga ggataagttt tattaacaag tgctatgagc tctgtgagac ataccctgct | 600 |
| cttttggtgg ttccctatcg gacctcagat gatgatctta ggaggatcgc aacgtttaga | 660 |
| tcccgaaatc ggcttcctgt actgtcgtgg attcacccag aaaacaaaat ggtcattatg | 720 |
| cgctgcagtc agcctcttgt cggtatgagt ggtaaaagaa ataaagatga cgagaaatac | 780 |
| ctggatgtga tcaggaaac taacaaacaa acttctaagc tcatgattta tgatgcacga | 840 |
| cccagtgtaa atgcagtcgc caacaaggca acaggaggag gatatgaaag tgatgacgca | 900 |
| tatcaaaact cagaactttc cttcttagac attcataata ttcatgttat gcgagaatct | 960 |
| ttaaaaaaag tgaagatat tgtttatccc aacatagaag aatctcattg gttgtccagt | 1020 |
| ttggagtcta ctcattggtt agaacatatc aagcttgttc tgaccggtgc cattcaagtg | 1080 |
| gcagaccaag tgtcttcagg aaagagctcg gtacttgtgc actgcagtga cggatgggac | 1140 |
| aggaccgctc agctgacatc cttggccatg ctgatgttgg acagcttcta cagaactatt | 1200 |
| gaaggctttg agatattggt acagaaagag tggataagtt ttggccataa atttgcatct | 1260 |
| agaataggtc atggtgataa aaaccatgct gatgctgatc gatctcctat ttttcttcag | 1320 |
| tttattgact gtgtgtggca gatgtcgaaa cagttcccca cagcttttga gttcaatgaa | 1380 |
| ggcttttga ttaccgtttt ggatcatctg tatagctgtc gatttggtac tttcttattc | 1440 |
| aactgtgact cggctcgaga aagacagaaa cttacagaaa gaacagtttc tctatggtcg | 1500 |
| ctaattaaca gcaataaaga caaattcaaa aaccccttct atacaaaaga aatcaatcgg | 1560 |
| gttttgtatc cagttgccag catgcgtcac ttggaactgt gggtgaatta ttacatccga | 1620 |
| tggaatccca gggtcaagca gcaacagccc aacccagtgg agcagcgtta catggagctt | 1680 |
| ttggccttgc gtgacgatta tataaagagg ctcgaggaat gcagctggc caactccgcc | 1740 |
| aagcttgctg atgccccgc ttcgacttcc agttcgtcac agatggtgcc ccatgtgcag | 1800 |
| acgcacttct ga | 1812 |

<210> SEQ ID NO 2
<211> LENGTH: 3339
<212> TYPE: DNA
<213> ORGANISM: Mus musculus

<400> SEQUENCE: 2

| | |
|---|---|
| cggtgagttc gctttcttgg ctgacctggc tcggagccgg gcattgcggg gatccaggat | 60 |
| tggaaaggtt ccaggatggc ttctgcatca gcatctaagt ataattcaca ctccttggag | 120 |
| aatgaatcca ttaagaaagt gtctcaagat ggagtcagtc aggatgtgag tgagactgtc | 180 |
| cctcggctcc caggggagtt actaattact gaaaaagaag ttatttacat atgtcctttc | 240 |
| aatggcccca ttaagggaag agtttacatc acaaattatc gtctttattt aagaagtttg | 300 |
| gaaacggatt ctgctctaat acttgatgtt cctctgggtg tgatatcaag aattgaatat | 360 |

-continued

```
atgggaggcg cgactagtag aggagaaaat tcctatggtc tagatattac ttgtaaagat    420
ttgagaaacc tgaggtttgc attgaagcaa gaaggccaca gcagaagaga tatgtttgag    480
atccttgtaa aacatgcctt tcctctggca cacaatctgc cattatttgc atttgtaaat    540
gaagagaagt ttaacgtgga tgggtggact gtttataatc cagttgaaga atatagaagg    600
cagggcctgc ccaatcacca ttggaggata agttttatta acaagtgcta tgagctctgt    660
gagacatacc ctgctctttt ggtggttccc tatcggacct cagatgatga tcttaggagg    720
atcgcaacgt ttagatcccg aaatcggctt cctgtactgt cgtggattca cccagaaaac    780
aaaatggtca ttatgcgctg cagtcagcct cttgtcggta tgagtggtaa aagaaataaa    840
gatgacgaga ataccctgga tgtgatcagg gaaactaaca aacaaacttc taagctcatg    900
atttatgatg cacgacccag tgtaaatgca gtcgccaaca aggcaacagg aggaggatat    960
gaaagtgatg acgcatatca aaactcagaa ctttccttct tagacattca taatattcat   1020
gttatgcgag aatctttaaa aaagtgaaa gatattgttt atcccaacat agaagaatct   1080
cattggttgt ccagtttgga gtctactcat tggttagaac atatcaagct tgttctgacc   1140
ggtgccattc aagtggcaga ccaagtgtct tcaggaaaga gctcggtact tgtgcactgc   1200
agtgacggat gggacaggac cgctcagctg acatccttgg ccatgctgat gttggacagc   1260
ttctacagaa ctattgaagg ctttgagata ttggtacaga aagagtggat aagttttggc   1320
cataaatttg catctagaat aggtcatggt gataaaaacc atgctgatgc tgatcgatct   1380 cctattttc ttcagtttat tgactgtgtg tggcagatgt cgaaacagtt ccccacagct   1440
tttgagttca atgaaggctt tttgattacc gttttggatc atctgtatag ctgtcgattt   1500
ggtactttct tattcaactg tgactcggct cgagaaagac agaaacttac agaaagaaca   1560
gtttctctat ggtcgctaat taacagcaat aaagacaaat tcaaaaaccc cttctataca   1620
aaagaaatca atcgggtttt gtatccagtt gccagcatgc gtcacttgga actgtgggtg   1680
aattattaca tccgatggaa tcccagggtc aagcagcaac agcccaaccc agtggagcag   1740
cgttacatgg agcttttggc cttgcgtgac gattatataa agaggctcga ggaattgcag   1800
ctggccaact ccgccaagct tgctgatgcc cccgcttcga cttccagttc gtcacagatg   1860
gtgccccatg tgcagacgca cttctgaggg gactcacttc tggcactgca cttgaactct   1920
agataagtga aatagctgac tctcattctg ggcatgtgga caaagtagat ttaaagtgtc   1980
tgcctccatt tagaagttca actaacatct tagacttttg agtatgtgcc ttctgtaata   2040
catatcacaa gaaatcgatg gtgtccgtgt ggcaatcata aggaaggagt caagagggg   2100 ttctggaaaa tcctcatact ttttttaca aagcactttt gcaaagataa aacttaaatt   2160
taatttacct ctatataaat tctacatata cagtatgtat tttgtgggct taattgaaat   2220
attattttaa atccaggggg gagatttgtt tgcaaaatgt attttcctcc agctgcttat   2280
aacagttgct ttggattatc taaaattaat ccaaatgtga agatgggta ttactgccaa   2340 agccaaattg cactctgctt cttcagcaaa ttccaagagc aaggcgttta ataattgcc   2400 aattttatt ttaccataag tggtaaggta aaagaaaga tgaacatttc atcattttga   2460 attttgaaa ataaaaggtt ctcccatcat ttttcaagag aagcacattt ttatattaag   2520 aaaagtgat aaggtttgat ttttttttcc ctcaacattc tcagctttgc tttctaaatt   2580
atcccatgat ttttgtctaa cactgagtca tactcaggtt gaaggaaacc cataaatagc   2640
actgtgcgag gagctggctg gcttctgctg cttagaggaa tatgttcgca acatgcctc   2700 tagtcaattc gccttatctg ctgaagtgta ggggcaccgc cttgaatgga tgagctatgg   2760
```

| ctagagcatc | tttctttaca | gtaatgcccc | aggtgtattc | tgtttatgtc | tctctgttta | 2820 |
| aatggtgtgc | gtgcataaaa | acttgctctg | cacattatta | cttgaagtac | tgggcaattt | 2880 |
| gcttttcag | gttttttttc | attttgtttt | gtagtatgaa | atggaatttt | aaatgcacag | 2940 |
| ttctatttga | tatccgaact | aattcattta | gtaaatatat | ttgtaaaagc | taaagttaaa | 3000 |
| tcaattaatg | ttttacagtg | atttgtaaag | gattatttat | agctaatatg | gttttgtttt | 3060 |
| cagtgaatta | agagagatta | catttatctt | tgtaaattat | tttatgtcat | agcttaatgg | 3120 |
| cctaccaaat | gagacatctc | aaatataata | gtataatgta | tggattttgt | aagtataaaa | 3180 |
| attattagat | attcgtttgc | tttttgtaaa | cactgtaaat | atttcataaa | ttaaaatgtg | 3240 |
| tcactccata | agaagaaaaa | actaatacta | atagttgaca | ggaattggtg | aaatttcatg | 3300 |
| aaaatatttt | cattgcaata | atattaaaaa | gacctgctg | | | 3339 |

<210> SEQ ID NO 3
<211> LENGTH: 1812
<212> TYPE: DNA
<213> ORGANISM: Canis familiaris

<400> SEQUENCE: 3

| atggcttctg | caccaacttc | taaatataat | tcacactcct | tggagaacga | gtctattaag | 60 |
| aggacttcta | gggatggagt | taattgggac | ctgagtgagg | ctgttcctcg | acttccagga | 120 |
| gaaactcgta | tcactgacaa | agaagttatt | tacatatgtc | ctttcaatgg | ccccattaag | 180 |
| ggaagagttt | acatcacaaa | ttatcgtctt | tatttaagaa | gtttggaaac | ggattctgct | 240 |
| ctaatacttg | atgttcctct | gggtgtgatc | tccagaattg | aaaaaatggg | aggcgcgaca | 300 |
| agtagaggag | aaaattcgta | tggtctagat | attacttgta | aagacatgag | gaacttgagg | 360 |
| ttcgcgctga | aacaggaagg | ccacagcagg | agggatatgt | ttgagatcct | cacaagatac | 420 |
| gcctttccct | tggcccacag | tctgccaata | tttgcatttc | taaacgaaga | aaagtttaac | 480 |
| gtggatgggt | ggacagttta | taatccagtc | gaagaataca | aaggcaggg | cttgcccaat | 540 |
| caccactgga | gaataacttt | tatcaacaag | tgctatgagc | tctgtgacac | ttatcctgct | 600 |
| ctcttggtgg | ttccatatcg | tgcctcagat | gacgatctca | ggagagttgc | aacttttaga | 660 |
| tccagaaatc | gaattccagt | gctgtcatgg | attcatccag | aaaacaagac | ggtcattgtg | 720 |
| cgctgcagcc | agcctcttgt | cggaatgagt | ggtaaacgga | ataaagatga | tgagaagtat | 780 |
| ctcgatgtta | tcaggagac | taacagacaa | atttctaaac | tcacaatcta | tgatgccaga | 840 |
| cccaatgtaa | atgccgtggc | caacaaggca | acaggaggag | gatatgaaag | tgatgatgca | 900 |
| tatcataacg | ccgaactttt | cttcttagac | attcataaca | ttcatgttat | gcgggaatct | 960 |
| ttaaaaaag | tcaagacat | cgtttatcct | aatgtgaag | agtctcactg | gctgtccagt | 1020 |
| ttggagtcta | cccattggtt | agaacatatc | aagcttgttt | tgacgggagc | cattcaagta | 1080 |
| gcagacagag | tttcttcagg | gaagagctca | gtgctcgtgc | actgcagcga | tggatgggac | 1140 |
| aggactgccc | agctgacgtc | cttggccatg | ctgatgctcg | acagcttcta | tcggagcatc | 1200 |
| gagggctttg | aaatattggt | acaaaaggaa | tggataagtt | ttggacataa | gtttgcatct | 1260 |
| agaataggtc | atggtgataa | aaaccacgcc | gacgctgacc | ggtctcctat | tttctctccag | 1320 |
| tttattgatt | gtgtatggca | aatgtcaaaa | cagttcccta | cagcttttga | attcaatgaa | 1380 |
| cgatttttga | ttacaatttt | ggatcatctg | tatagttgcc | ggtttggtac | cttcttgtac | 1440 |
| aactgtgaat | ctgctcggga | aaaacagaaa | gtgacggaac | gaacagtatc | tttatggtca | 1500 |

```
ctgataaaca gtaataagga caaattcaaa aatcccttct atactaaaga aatcaatcga    1560
gttttatatc cagttgccag tatgcgtcac ttggaactt t gggtgaatta ctacattaga    1620
tggaacccca ggatcaagca acaacagccc aacccagtgg agcagcggta cgtggagctg    1680
ttggccttgc gtgacgaata catacagcgg ctcgaggagc tgcagctcgc cagctcggcc    1740
aagctgcccg accectcgac ctcaccggcc gggccctcgc agatgatgcc gcacgtgcgc    1800
acacacttct ga                                                        1812
```

<210> SEQ ID NO 4
<211> LENGTH: 1841
<212> TYPE: DNA
<213> ORGANISM: Canis familiaris

<400> SEQUENCE: 4

```
cggtggcgcc cggaccccga gtttccagta tggcttctgc accaacttct aaatataatt      60
cacactcctt ggagaacgag tctattaaga ggacttctag ggatggagtt aattgggacc     120
tgagtgaggc tgttcctcga cttccaggag aaactcgtat cactgacaaa gaagttattt     180
acatatgtcc tttcaatggc cccattaagg aagagtttta catcacaaat tatcgtcttt     240
atttaagaag tttggaaacg gattctgctc taatacttga tgttcctctg ggtgtgatct     300
ccagaattga aaaatgggga ggcgcgacaa gtagaggaga aaattcgtat ggtctagata     360
ttacttgtaa agacatgagg aacttgaggt tcgcgctgaa acaggaaggc cacagcagga     420
gggatatgtt tgagatcctc acaagatacg cctttccctt ggcccacagt ctgccaatat     480
ttgcatttct aaacgaagaa aagtttaacg tggatgggtg gacagtttat aatccagtcg     540
aagaatacag aaggcagggc ttgcccaatc accactggag ataaacttt  atcaacaagt     600 gctatgagct ctgtgacact tatcctgctc tcttggtggt tccatatcgt gcctcagatg     660
acgatctcag gagagttgca acttttagat ccagaaatcg aattccagtg ctgtcatgga     720
ttcatccaga aaacaagacg gtcattgtgc gctgcagcca gcctcttgtc ggaatgagtg     780
gtaaacggaa taagatgat gagaagtatc tcgatgttat cagggagact aacagacaaa     840
tttctaaact cacaatctat gatgccgac  ccaatgtaaa tgccgtggcc aacaaggcaa     900
caggaggagg atatgaaagt gatgatgcat atcataacgc cgaactttc ttcttagaca      960 ttcataacat tcatgttatg cgggaatctt taaaaaagt caaagacatc gtttatccta    1020
atgtggaaga gtctcactgg ctgtccagtt tggagtctac ccattggtta gaacatatca    1080
agcttgtttt gacgggagcc attcaagtag cagacagagt tcttcaggg aagagctcag     1140 tgctcgtgca ctgcagcgat ggatgggaca ggactgccca gctgacgtcc ttggccatgc    1200
tgatgctcga cagcttctat cggagcatcg agggctttga aatattggta caaaaggaat    1260
ggataagttt tggacataag tttgcatcta gaataggtca tggtgataaa aaccacgccg    1320
acgctgaccg gtctcctatt tttctccagt ttattgattg tgtatggcaa atgtcaaaac    1380
agttccctac agcttttgaa ttcaatgaac gatttttgat tacaattttg gatcatctgt    1440
atagttgccg gtttggtacc ttcttgtaca actgtgaatc tgctcgggaa aaacagaaag    1500
tgacggaacg aacagtatct ttatggtcac tgataaacag taataaggac aaattcaaaa    1560
atcccttcta tactaaagaa atcaatcgag ttttatatcc agttgccagt atgcgtcact    1620
tggaactttg ggtgaattac tacattagat ggaacccag gatcaagcaa caacagccca    1680
acccagtgga gcagcggtac gtggagctgt tggccttgcg tgacgaatac atacagcggc    1740
tcgaggagct gcagctcgcc agctcggcca agctgcccga cccctcgacc tcaccggccg    1800
```

-continued ggccctcgca gatgatgccg cacgtgcgca cacacttctg a            1841

<210> SEQ ID NO 5
<211> LENGTH: 1812
<212> TYPE: DNA
<213> ORGANISM: Homo sapiens

<400> SEQUENCE: 5
atggcttctg catcaacttc taaatataat tcacactcct tggagaatga gtctattaag     60
aggacgtctc gagatggagt caatcgagat ctcactgagg ctgttcctcg acttccagga    120
gaaacactaa tcactgacaa agaagttatt tacatatgtc ctttcaatgg ccccattaag    180
ggaagagttt acatcacaaa ttatcgtctt tatttaagaa gtttggaaac ggattcttct    240
ctaatacttg atgttcctct gggtgtgatc tcgagaattg aaaaaatggg aggcgcgaca    300
agtagaggag aaaattccta tggtctagat attacttgta agacatgag aaacctgagg     360
ttcgctttga acaggaagg ccacagcaga agagatatgt tgagatcct cacgagatac      420
gcgtttcccc tggctcacag tctgccatta tttgcatttt taaatgaaga aaagtttaac    480
gtggatggat ggacagttta caatccagtg aagaataca ggaggcaggg cttgcccaat      540
caccattgga gaataacttt tattaataag tgctatgagc tctgtgacac ttaccctgct    600
cttttggtgg ttccgtatcg tgcctcagat gatgacctcc ggagagttgc aacttttagg    660
tcccgaaatc gaattccagt gctgtcatgg attcatccag aaaataagac ggtcattgtg    720
cgttgcagtc agcctcttgt cggtatgagt gggaaacgaa ataaagatga tgagaaatat    780
ctcgatgtta tcagggagac taataaacaa atttctaaac tcaccattta tgatgcaaga    840
cccagcgtaa atgcagtggc caacaaggca acaggaggag gatatgaaag tgatgatgca    900
tatcataacg ccgaactttt cttcttagac attcataata ttcatgttat gcgggaatct    960
ttaaaaaaag tgaaggacat tgtttatcct aatgtagaag aatctcattg gttgtccagt   1020
ttggagtcta ctcattggtt agaacatatc aagctcgttt tgacaggagc cattcaagta   1080
gcagacaaag tttcttcagg gaagagttca gtgcttgtgc attgcagtga cggatgggac   1140
aggactgctc agctgacatc cttggccatg ctgatgttgg atagcttcta taggagcatt   1200
gaagggttcg aaatactggt acaaaaagaa tggataagtt ttggacataa attgcatct     1260
cgaataggtc atggtgataa aaaccacacc gatgctgacc gttctcctat ttttctccag   1320
tttattgatt gtgtgtggca aatgtcaaaa cagttcccta cagcttttga attcaatgaa   1380
caatttttga ttataatttt ggatcatctg tatagttgcc gatttggtac tttcttattc   1440
aactgtgaat ctgctcgaga aagacagaag gttacagaaa ggactgtttc tttatggtca   1500
ctgataaaca gtaataaaga aaaattcaaa aaccccttct atactaaaga aatcaatcga   1560
gttttatatc cagttgccag tatgcgtcac ttggaactct gggtgaatta ctacattaga   1620
tggaacccca ggatcaagca acaacagccg aatccagtgg agcagcgtta catggagctc   1680
ttagccttac gcgacgaata cataaagcgg cttgaggaac tgcagctcgc caactctgcc   1740
aagcttctg atcccccaac ttcaccttcc agtccttcgc aaatgatgcc ccatgtgcaa    1800
actcacttct ga                                                       1812

<210> SEQ ID NO 6
<211> LENGTH: 3452
<212> TYPE: DNA
<213> ORGANISM: Homo sapiens

```
<400> SEQUENCE: 6 agaggggcg gagcagggcc cggcagccga gcagcctggc aacggcggtg gcgcccggag      60
cccgagagtt tccaggatgg cttctgcatc aacttctaaa tataattcac actccttgga    120
gaatgagtct attaagagga cgtctcgaga tggagtcaat cgagatctca ctgaggctgt    180
tcctcgactt ccaggagaaa cactaatcac tgacaaagaa gttatttaca tatgtccttt    240
caatggcccc attaagggaa gagtttacat cacaaattat cgtctttatt taagaagttt    300
ggaaacggat tcttctctaa tacttgatgt tcctctgggt gtgatctcga gaattgaaaa    360
aatgggaggc gcgacaagta gaggagaaaa ttcctatggt ctagatatta cttgtaaaga    420
catgagaaac ctgaggttcg ctttgaaaca ggaaggccac agcagaagag atatgtttga    480
gatcctcacg agatacgcgt ttcccctggc tcacagtctg ccattatttg catttttaaa    540
tgaagaaaag tttaacgtgg atggatggac agtttacaat ccagtggaag aatacaggag    600
gcagggcttg cccaatcacc attggagaat aacttttatt aataagtgct atgagctctg    660
tgacacttac cctgctcttt tggtggttcc gtatcgtgcc tcagatgatg acctccggag    720
agttgcaact tttaggtccc gaaatcgaat tccagtgctg tcatggattc atccagaaaa    780
taagacggtc attgtgcgtt gcagtcagcc tcttgtcggt atgagtggga aacgaaataa    840
agatgatgag aaatatctcg atgttatcag ggagactaat aaacaaattt ctaaactcac    900
catttatgat gcaagaccca gcgtaaatgc agtggccaac aaggcaacag gaggaggata    960
tgaaagtgat gatgcatatc ataacgccga acttttcttc ttagacattc ataatattca   1020
tgttatgcgg gaatctttaa aaaaagtgaa ggacattgtt tatcctaatg tagaagaatc   1080
tcattggttg tccagtttgg agtctactca ttggttagaa catatcaagc tcgttttgac   1140
aggagccatt caagtagcag acaaagtttc ttcaggaaag agttcagtgc ttgtgcattg   1200
cagtgacgga tgggacagga ctgctcagct gacatccttg gccatgctga tgttggatag   1260
cttctatagg agcattgaag ggttcgaaat actggtacaa aaagaatgga taagttttgg   1320
acataaattt gcatctcgaa taggtcatgg tgataaaaac cacaccgatg ctgaccgttc   1380
tcctattttt ctccagtttta ttgattgtgt gtggcaaatg tcaaaacagt ccctacagc   1440
ttttgaattc aatgaacaat ttttgattat aattttggat catctgtata gttgccgatt   1500
tggtactttc ttattcaact gtgaatctgc tcgagaaaga cagaaggtta cagaaaggac   1560
tgtttcttta tggtcactga taaacagtaa taaagaaaaa ttcaaaaacc ccttctatac   1620
taaagaaatc aatcgagttt tatatccagt tgccagtatg cgtcacttgg aactctgggt   1680
gaattactac attagatgga accccaggat caagcaacaa cagccgaatc cagtggagca   1740
gcgttacatg gagctcttag ccttacgcga cgaatacata aagcggcttg aggaactgca   1800
gctcgccaac tctgccaagc tttctgatcc cccaacttca ccttccagtc cttcgcaaat   1860
gatgccccat gtgcaaactc acttctgagg ggggaccctg gcaccgcatt agagctcgaa   1920
ataaaggcga tagctgactt tcatttgggg catttgtaaa aagtagatta aaatatttgc   1980
ctccatgtag aacttgaact aacataatct taaactcttg aatatgtgcc ttctagaata   2040
catattacaa gaaaactaca gggtccacac ggcaatcaga agaaaggagc tgagatgagg   2100
ttttggaaaa ccctgacacc tttaaaaagc agtttttgaa agacaaaatt tagatttaat   2160
ttacgtcttg agaaatacta tatatacaat atatattttg tgggcttaat tgaaacaaca   2220
ttattttaaa atcaaagggg atatatgttt gtggaatgga ttttcctgaa gctgcttaac   2280
agttgctttg gattctctaa gatgaatcca aatgtgaaag atgcatgtta ctgccaaaac   2340
```

```
caaattgagc tcagcttcct aggcattacc caaaagcaag gtgtttaagt aattgccagc    2400
ttttatacca tcatgagtgg tgacttaagg agaaatagct gtatagatga gtttttcatt    2460
atttggaaat ttaggggtag aaaatgtttt ccctaattt tccagagaag cctattttta    2520 tattttaaa aaactgacag ggcccagtta aatatgattt gcattttta aatttgccag    2580 ttttattttc taaattcttt catgagcttg cctaaaattc ggaatggttt tcgggttgtg    2640
gcaaacccca agagagcac tgtccaagga tgtcggagc atcctgctgc ttaggggaat    2700
gttttcgcaa atgttgctct agtcagtcca gctcatctgc caaaatgtag ggctaccgtc    2760
ttggatgcat gagctattgc tagagcatca tccttagaaa tcagtgcccc agatgtacat    2820
gtgttgagcg tattcttgaa agtattgtgt ttatgcattt caatttcaat ggtgttggct    2880
tcccctcccc accccacgcg tgcataaaaa ctggttctac aaattttac ttgaagtacc    2940 aggccgtttg cttttcagg ttgttttgtt ttatagtatt aagtgaaatt ttaaatgcac    3000
agttctattt gctatctgaa ctaattcatt tattaagtat atttgtaaaa gctaaggctc    3060
gagttaaaac aatgaagtgt tttacaatga tttgtaaagg actatttata actaatatgg    3120
ttttgttttc aatgaattaa gaaagattaa atatatcttt gtaaattatt ttatgtcata    3180
gtttaattgg tctaccaagt aagacatctc aaatacagta gtataatgta tgaattttgt    3240
aagtataaga aattttatta gacattctct tactttttgt aaatgctgta aatatttcat    3300
aaattaacaa agtgtcactc cataaaaaga aagctaatac taatagccta aaagattttg    3360
tgaaatttca tgaaaacttt ttaatggcaa taatgactaa agacctgctg taataaatgt    3420
attaactgaa acctaaaaaa aaaaaaaaaa aa                                  3452

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
ataagttttg gacataagtt tgc                                             23

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
catttgccat acacaatcaa                                                 20

<210> SEQ ID NO 9
<211> LENGTH: 20
<212> TYPE: DNA
<213> ORGANISM: Artificial Sequence
<220> FEATURE:
<223> OTHER INFORMATION: Probe

<400> SEQUENCE: 9
cgacgctgac cggtctccta                                                 20

<210> SEQ ID NO 10
<211> LENGTH: 20
<212> TYPE: DNA
```

```
<213> ORGANISM: Artificial Sequence
<220> FEATURE:
<223> OTHER INFORMATION: Primer

<400> SEQUENCE: 10
acgctgattg ctcacaccaa                                                      20

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
ccccaggtct gcttcatagt tg                                                   22

<210> SEQ ID NO 12
<211> LENGTH: 21
<212> TYPE: DNA
<213> ORGANISM: Artificial Sequence
<220> FEATURE:
<223> OTHER INFORMATION: Probe

<400> SEQUENCE: 12
cccggcccgt gacctttgtg a                                                    21
```

SYSTEMIC GENE REPLACEMENT THERAPY FOR TREATMENT OF X-LINKED MYOTUBULAR MYOPATHY (XLMTM)

CROSS-REFERENCE TO RELATED APPLICATIONS

The present application is a continuation of U.S. patent application Ser. No. 15/220,139, filed Jul. 26, 2016, which is a continuation of U.S. patent application Ser. No. 14/595, 540, filed Jan. 13, 2015, now U.S. Pat. No. 9,415,120, which is a continuation of U.S. patent application Ser. No. 14/194, 186, filed Feb. 28, 2014, now U.S. Pat. No. 8,957,044, which claims priority under 35 U.S.C. § 119(e) to U.S. Provisional Application No. 61/771,449, filed Mar. 1, 2013, each of which are hereby incorporated by reference in their entirety herein.

STATEMENT REGARDING FEDERALLY SPONSORED RESEARCH OR DEVELOPMENT

This invention was made with government support under P50 NS040828 and RO1 AR044345, awarded by the National Institutes of Health (NIH). The government has certain rights in the invention.

BACKGROUND OF THE INVENTION

Recent progress raises anticipation that in vivo gene replacement will successfully treat many human genetic disorders (Epica, et al., 2002, Anim Genet 33(1):81-2; Guan et al., 2011, PMR 3(6 Suppl 1):S95-9; Forbes et al., 1985, AJR Am J Roentgenol 145(1):149-54). Nonetheless, substantial hurdles must be overcome to achieve regulatory approval for human gene therapies (Kornegay et al., 2011, Methods Mol Biol 709:105-234), such as successful treatment in predictive animal models. X-linked myotubular myopathy (XLMTM; OMIM 310400) is a fatal monogenic disease of skeletal muscle. Affected newborn boys, approximately one per 50,000 births, typically display marked hypotonia and respiratory failure (Jungbluth et al., 2008, Orphanet J Rare Dis 3:26). Survival beyond the postnatal period requires intensive support, often including gastrostomy feeding and mechanical ventilation (Herman et al., 1999, J Pediatr 134(2):206-14). No effective therapy to treat this disease exists.

XLMTM results from loss-of-function mutations in Myotubularin 1 (MTM1) (Laporte et al., 1996, Nat Genet 13(2): 175-82). This gene encodes one of a family of 3-phosphoinositide phosphatases which act on the second messengers phosphatidylinositol 3-monophosphate [PI(3)P] and phosphatidylinositol 3,5-bisphosphate [PI(3,5)P$_2$] (Rosset et al., 2004, J Digit Imaging 17(3):205-16; Yue et al., 2011, Methods Mol Biol 709:313-29; Salgado et al., 2003, JBR-BTR 86(4):215-20; Miyagoe-Suzuki and Takeda, 2010, Exp Cell Res 316(18):3087-92). Although myotubularin is expressed ubiquitously, loss of this enzyme primarily affects skeletal muscle. Myogenesis occurs, but muscle fibers throughout the body are hypotrophic and display structural abnormalities, with associated weakness (Buj-Bello et al., 2002, Proc Natl Acad Sci USA 99(23):15060-5).

The mammalian X-linked myotubularin gene is highly conserved (Laporte et al., 1998, Hum Mol Genet 7(11): 1703-12; Laporte et al., 2000, Hum Mutat 15(5):393-409; Beggs et al., 2010, Proc Natl Acad Sci USA 107(33):14697-702). Genetic disruption of Mtm1 in mice causes profound abnormalities in skeletal muscle mass, structure, and function, regardless whether expression is knocked out constitutively or only in muscle (Buj-Bello et al., 2002, Proc Natl Acad Sci USA 99(23):15060-5; Al-Qusairi et al., 2009, Proc Natl Acad Sci USA 106(44):18763-8). The phenotype resembles human XLMTM, with similar pathology and early mortality.

Thus there is a need in the art for effective and non-invasive compositions and methods for treating myopathy, including XLMTM. The present invention satisfies this unmet need.

BRIEF SUMMARY OF THE INVENTION

The invention includes a method of treating a myopathy in a subject in need thereof, the method comprising systemically administering to the subject a composition that increases the expression of myotubularin in a muscle of the subject.

The invention further includes a method of prolonging the survival of a subject with myopathy, the method comprising systemically administering to the subject a composition that increases the expression of myotubularin in a muscle of the subject.

The invention also includes a composition comprising a nucleic acid sequence comprising MTM1, wherein the composition is suitable for systemic delivery to a subject, further wherein the composition comprises a viral vector.

In certain embodiments, the composition comprises a nucleic acid sequence encoding myotubularin. In other embodiments, the composition comprises the myotubularin gene (MTM1). In yet other embodiments, the composition further comprises an expression vector comprising a viral vector. In yet other embodiments, the composition further comprises a muscle specific promoter.

In certain embodiments, the viral vector is selected from the group consisting of a lentiviral vector, retroviral vector, adenoviral vector, and adeno-associated viral (AAV) vector. In other embodiments, the AAV vector comprises a serotype selected from the group consisting of AAV1, AAV2, AAV3, AAV4, AAV5, AAV6, AAV7, AAV8, and AAV9. In yet other embodiments, the AAV vector is a recombinant AAV vector. In yet other embodiments, the composition comprises myotubularin, or a biologically functional fragment thereof.

In certain embodiments, the myopathy comprises X-linked myotubular myopathy (XLMTM). In other embodiments, the administration route comprises at least one selected from the group consisting of enteral, parenteral, oral, intravenous, intra-arterial, and inhalational. In yet other embodiments, the administration route comprises intravenous.

In certain embodiments, the muscle of the subject exhibits an increase in myotubularin expression for up to 6 months as compared to the muscle of the subject in the absence of administration of the composition. In other embodiments, the muscle of the subject exhibits an increase in myotubularin expression for up to 1 year as compared to the muscle of the subject in the absence of administration of the composition. In yet other embodiments, the muscle of the subject exhibits a sustained increase in strength for up to 6 months as compared to the muscle of the subject in the absence of administration of the composition. In yet other embodiments, the subject has longer survival than a subject who is not administered the composition. In yet other embodiments, the function of the diaphragm of the subject is improved as compared to the diaphragm of the subject in the absence of administration of the composition.

In certain embodiments, a single administration of the composition is performed in the subject within a period of time. In other embodiments, two or more administrations of the composition are performed in the subject within a period of time. In yet other embodiments, the subject is a mammal. In yet other embodiments, the mammal is a human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

(FIG. 1A) Experimental design. (FIG. 1B) Survival and (FIG. 1C) body mass of wild-type mice (WT) and constitutive KO-Mtm1 mice injected at 3 weeks of age with saline (WT+saline, KO+saline, n=10 per genotype). Myotubularin-deficient mice were injected with rAAV-Mtm1 at $3\times10^{13}$ viral genomes per kg (vg/kg) at 3 (KO+AAV, n=12) and 5 weeks of age (KO Late+AAV, n=12) during a 6 months follow-up study. (FIG. 1D) Mass of representative skeletal muscles of KO-Mtm1 mice 2 weeks after injection of saline (KO+saline, n=4) and 6 months (n=10 after injection of rAAV-Mtm1 (KO+AAV, n=7, and KO Late+AAV, n=8). Values were normalized to muscle mass of age-matched, saline-injected WT mice (n=10), taken as 100%. (FIG. 1E) Myotubularin protein quantification by immunoblot compared to endogenous levels (line=1); GAPDH immunodetection was used an internal control. The number of animals was as in FIG. 1D. Muscles: TA=tibialis anterior; EDL=extensor digitorum longus; SOL=soleus; GA=gastrocnemius; QUA=quadriceps; TRI=triceps; BI=biceps brachii; DIA=diaphragm. Statistical significance: $P<0.05$ (one symbol); $P<0.01$ (two symbols); $P<0.001$ (three symbols); Mann-Whitney test, each condition versus WT+saline values.

(FIG. 2A) Cross-sections from tibialis anterior (TA) muscle stained with hematoxylin and eosin (HE) and NADH-TR, and by immunofluorescence with antibodies against DHPR1α and dysferlin. Scale bars=10 μm. (FIG. 2B) Mean diameter of muscle fibers from TA and biceps brachii muscles from mice injected with either saline or rAAV-Mtm1 after 2 weeks (left graph) and 6 months of treatment (right graph). WT+saline, n=10; KO+saline, n=4; KO+AAV, n=7, and KO Late+AAV, n=8. Statistical significance: $P<0.05$ (one symbol, *); $P<0.01$ (two symbols, ); $P<0.001$ (three symbols, *); t test, each condition versus WT+saline values.

FIGS. 3A-3C depict the results of experiments demonstrating that gene replacement therapy with rAAV8-Mtm1 improves strength, activity and long-term survival in myotubularin deficient mice. (FIG. 3A) Whole-body spontaneous mobility of normal (WT+saline), mutant (KO+saline) and AAV-treated mutant (KO+AAV-Mtm1) mice 2 weeks (5 weeks of age) and 6 months after PBS or vector injection. The distance covered over the 90-min test was assessed using an open field actimeter. (FIG. 3B) Escape test measurements in the 5 groups of mice. (FIG. 3C) Specific tetanic force of isolated EDL muscles from KO mice injected at an early and late stage of the disease 6 months after vector delivery compared to saline-injected KO and WT littermates. Drawings of the tests are shown on the left side of each figure section. WT+saline, n=6; KO+saline, n=4 at 5 weeks; WT+saline, n=10; KO+saline, n=4; KO early+AAV, n=8, and KO Late+AAV, n=8 at 6 months. Statistical significance: $P<0.05$ (one symbol, *); $P<0.01$ (two symbols, ); $P<0.001$ (three symbols, *); t test.

(FIG. 4A) Cranial tibialis canine muscles 6 weeks after AAV8-MTM1 intramuscular injection. Immunoblot of myotubularin (MTM1) and GAPDH from cranialtibialis muscle lysates at proximal, middle, or distal sections of the muscle. (FIG. 4B) MTM1 gene replacement therapy increases hindlimb strength in XLMTM dogs. The drawing shows the method used to measure hindlimb flexion strength in dogs. A nerve stimulator delivers electrical frequencies from 1 to 110 Hz to muscles that pull the paw toward the stifle (knee). A transducer captures the torque generated when the paw pulls on the foot pedal. Upper graph: baseline before injection, 10 weeks of age (WT, n=3; XLMTM, n=3); middle graph: 4 weeks after injection, 14 weeks of age (WT, n=3; XLMTM, n=3); bottom graph: 6 weeks after injection, 16 weeks of age (WT, n=2; XLMTM, n=2). $P=0.002$ (4 weeks after injection); $P=0.0161$ (6 weeks after injection; XLMTM+AAV versus WT+saline values), one-way analysis of variance (ANOVA). (FIG. 4C) Local myotubularin gene replacement therapy improves muscle fiber architecture in XLMTM dogs. Cryosections of the cranial tibialis muscle (middle part) were assessed microscopically: Grey boxes in NADH-TR staining show areas magnified below; immunofluorescence staining for DHPR1a and dysferlin shows correction of abnormal organelles with AAV8-MTM1 (large grey arrow). Scale bars, 25 mm. Electron microscopy (EM) shows normal T-tubules (small black arrows) and abnormal L-tubules (small white arrow). Scale bar, 500 nm. Bottom panel: Close-up of WT muscle and schematic showing normal relationship of sarcomere ends (Z-line), and triads of T-tubules and sarcoplasmic reticulum (SR).

(FIG. 5A) Peak hindlimb torque at various times up to 1 year after infusion. (FIG. 5B) Baseline before infusion, 9 weeks of age (WT, n=2; XLMTM+AAV8, n=3; XLMTM+saline, n=1). (FIG. 5C) Six weeks after infusion, 15 weeks of age (WT, n=2; XLMTM+AAV8, n=2; XLMTM+saline, n=2). (FIG. 5D) Eight weeks after infusion, 17 weeks of age (WT, n=3; XLMTM+AAV8, n=3; XLMTM+saline, n=3). (FIG. 5E) Fourteen weeks after infusion, 23 weeks of age (WT, n=3; XLMTM+AAV8, n=3). XLMTM dogs infused only with saline did not survive beyond 18 weeks of age. (FIG. 5F) One year after infusion (WT, n=1; carrier, n=3; XLMTM+AAV8, n=3). (FIG. 5G) Pic inspiratory flow (PIF), a respiratory functional measure reflecting diaphragm muscle strength, taken in anesthetized dogs at baseline and at 8 weeks, 14 weeks, and 1 year after infusion with AAV8. Number of animals per group was the same as in (FIG. 5B) to (FIG. 5F). P<0.001 (three symbols, ***); one-way ANOVA, each condition versus WT+saline values.

(FIG. 6A) Representative micrographs of quadriceps muscle cross sections from muscle biopsies taken 4 weeks after infusion from dog 4 stained with H&E or NADH-TR. (FIG. 6B) H&E-stained cranial tibialis muscle cross sections taken 1 year after AAV infusion. Graphs indicate myofiber diameter frequency distribution of corresponding images for the vastus lateralis muscle (upper graph) and craniotibialis muscle (lower graph). Scale bars, 25 mm.

(FIGS. 7A-7B) Comparison of vector distribution (FIG. 7A) and MTM1 transgene expression (FIG. 7B) among upper and lower limb muscle biopsies collected 4 weeks after infusion in three XLMTM dogs: dogs 4 to 6. Upper limb muscles: triceps (TRI) and biceps brachii (BI bra). Lower limb muscles: biceps femoris (BI fem) and quadriceps (QUA). R, right; L, left; inf, infused limb. (FIG. 7B) Expression of canine MTM1 protein relative to the housekeeping gene GAPDH in whole-muscle lysates probed with anti-myotubularin antibody. (FIGS. 7C-7D) Comparison of vector distribution (FIG. 7C) and MTM1 transgene expression (FIG. 7D) among upper and lower limb muscle necropsy samples collected 1 year after infusion in dog 4, an XLMTM dog. Muscles of the infused leg: VL, vastus lateralis; VM, vastusmedialis; RF, rectus femoris; Ad, adductor magnus; Pec, pectineus; Sar, cranial sartorius; Gra, gracilis; BI fem, biceps femoris; ST, semitendinosus; SM, semimembranosus; CT, cranial tibialis; Gast, gastrocnemius; Per, peroneus longus. Muscles distal to the infused leg: Dia, diaphragm; Interc, intercostals; He, heart.

(FIG. 8A) Left panel: Body mass of wild-type (WT) and KO-Mtm1 mice before injection. Right panel mass of representative skeletal muscles: quadriceps (QUA), tibialis anterior (TA), triceps (TRI) (n=9 for each genotype, both contralateral muscles were analyzed per mouse). Note the significant reduction of TA muscle mass in KO-Mtm1 mice (P<0.01). (FIG. 8B) Hematoxylin and eosin (H&E) and nicotinamide adenine dinucleotide tetrazolium reductase (NADH-TR) staining of TA muscle cross-sections. Note the presence of small myofibers, internalized nuclei and altered mitochondrial oxidative staining distribution in KO-Mtm1 muscle. Scale bars=50 μm.

(FIG. 9A) Distribution of myofiber diameters of tibialis anterior (TA, upper right panels) and biceps brachii (BI, lower right panels) muscles at 6 months post-injection in the two group of Mtm1 KO animals (3 weeks and 5 weeks of age at injection). Left panels show the distribution of fibers from 5 weeks old WT and KO mice (FIG. 9B) Nuclei internalization. The percentage of myofibers with internal nuclei was quantified in tibialis anterior muscle and biceps brachii of mice from the various treatment conditions. (FIG. 9C) Myotubularin protein quantification in heart by immunoblot 6 months after vector administration; GAPDH immunodetection was used as an internal control (WT+saline, n=10 and KO Early+AAV, n=7), Statistical significance: P<0.05 (one symbol, *); P<0.01 (two symbols, ); P<0.001 (three symbols, *); t-test, each condition versus WT+saline. Number of animals: WT+saline, n=6 and KO+saline, n=4 at 5 weeks; WT+saline, n=10, n=4 KO Early+AAV, n=8, and KO Late+AAV, n=8 at 6 months.

(FIG. 10A) Survival and (FIG. 10B) body mass of wild type mice (WT) and constitutive KO-Mtm1 mice during a 3 months follow-up study. Mice received either saline (WT+saline, n=20, KO+saline, n=10) or the AAV8-Mtm1 vector at $3 \times 10^{13}$ vg/mL (KO+AAV, n=10) and $5 \times 10^{12}$ vg/mL (KO+AAV Low, n=10). (FIG. 10C) Mass of representative skeletal muscles of Mtm1 KO mice 3 months after vector injection. Values were normalized to muscle mass of age-matched, saline-injected WT mice, taken as 100%. Muscles: TA=tibialis anterior; EDL=extensor digitorum longus; SOL=soleus; GA=gastrocnemius; QUA=quadriceps; TRI=triceps; BI=biceps brachii. (FIG. 10D) Myotubularin protein quantification by immunoblot compared to endogenous levels (line=1); GAPDH immunodetection was used an internal control. (FIG. 10E) Distance covered in the 90-min actimeter test, global strength in the escape test and specific tetanic force of isolated EDL and soleus muscles of mice 3 months post-injection. In (FIG. 10C) and (FIG. 10D), n=7 for KO+AAV, n=5 for KO+AAV low and n=10 for WT+saline). Statistical significance: P<0.05 (one symbol, *); P<0.01 (two symbols, ); P<0.001 (three symbols, *); each condition versus WT+saline values.

(FIG. 11A) Necropsy photos (top panel) of the injected canine hind limb muscles in comparison to CT reconstruction images (bottom panel). In each pair the left image is from the limb injected with rAAV-MTM1, and the right image is the saline-treated control (see also FIG. 4). (FIG. 11B) Muscle volume of injected hind limbs muscles 1 day prior to necropsy. XLMTM=affected dog; WT=unaffected littermate; +MTM1=injected with rAAV-MTM1 at 10 weeks of age (4 or 6 weeks prior to necropsy). Scale bars: 2 cm.

(FIG. 12A) Anesthetized dogs are positioned to allow the hind foot to rotate around the axis of a force transducer during repeated contractions. (FIGS. 12B-12D) Isometric flexion torque values are shown immediately following each of 30 eccentric contractions. Measurements were obtained (FIG. 12B) at baseline, 10 weeks-of-age, prior to injection (XLMTM n=3); (FIG. 12C) 4 weeks post-injection (XLMTM n=3); (FIG. 12D) 6 weeks post-injection (XLMTM n=2). WT=unaffected littermates (n=3). Two-way ANOVA was used to compare saline-treated XLMTM versus vector-treated XLMTM.

FIGS. 13A-13C depict the results of experiments demonstrating the in vivo strength measured 1 year after regional hindlimb infusion of AAV8-MTM1 in an XLMTM dog. (FIG. 13A) Hindlimb flexion strength in contralateral non-infused versus infused muscles of Dog 4, assessed 1 year after infusion. (FIG. 13B) CT reconstruction and (FIG. 13C) cross section through the thigh demonstrating marked hypertrophy of the infused limb (marked by a symbol *).

(FIGS. 16A-16B) Serum neutralizing factor (NAF), IgM and IgG antibodies against the AAV8 capsid. Sera were analyzed before and after intramuscular (FIG. 16A) or regional limb (FIG. 16B) administration of AAV8-MTM1. (FIGS. 16C-16D) Humoral response specific to MTM1 protein in XLMTM dogs. Sera were analyzed before and after intramuscular (FIG. 16C) or regional limb (FIG. 16D) administration of AAV8-MTM1.

(FIG. 19A) Survival of wild-type C57BL/6 mice (WT) injected at 3 weeks-of-age with saline (WT+saline, n=5) and constitutive KO-Mtm1 mice, of same age, injected with saline (KO+saline, n=10) or with rAAV-Mtm1 at $3.0 \times 10^{13}$ viral genomes per kg (vg/kg) (KO+AAV-Mtm1, n=5) during a 6 months follow-up study. (FIG. 19B) Body mass of saline-injected WT (n=11) and KO-Mtm1 (n=16) and rAAV9-Mtm1-injected KO (n=8) mice. (FIG. 19C) Mass of representative skeletal muscles of KO-Mtm1 mice 2 weeks after injection of saline (KO+saline, n=8) and 2 weeks (n=6) or 6 months (n=10) after injection of rAAV-Mtm1 (KO+AAV-Mtm1). Values were normalized to muscle mass of age-matched, saline-injected WT mice (n=12), taken as 100%. (FIG. 19D and FIG. 19H) Myotubularin protein quantification by immunoblot. Insets show representative blots for myotubularin (MTM1) and glyceraldehyde 3-phosphate dehydrogenase (GAPDH), used for normalization. (FIG. 19E) Survival of WT mice after injection at 4 weeks-of-age with saline (WT+saline, n=8) and of muscle-specific mKO-Mtm1 knockout mice after injection at same age with saline (mKO+saline, n=5) or rAAV Mtm1 at $0.5 \times 10^{13}$ vg/kg (mKO+AAV-Mtm1, n=6) during a 12 months follow-up study. (FIG. 19F) Body weights of mice from panel e. (FIG. 19G) Masses of representative skeletal muscles of mKO-Mtm1 mice at 12 months after treatment with rAAV-Mtm1, normalized to muscle masses of control WT+saline mice, taken as 100%. Muscles: TA=tibialis anterior; EDL=extensor digitorum longus; GA=gastrocnemius; QUA=quadriceps; TRI=triceps; BI=biceps brachii; DIA=diaphragm. Statistical significance: P<0.05 (one symbol, *); P<0.01 (two symbols, **). Symbols: * (WT+saline) versus (KO+saline); Δ (KO+saline) versus (KO+AAV-Mtm1); # (WT+saline) versus (KO+AAV-Mtm1).

(FIG. 20A) Whole muscle cross-sections from tibialis anterior (TA) stained with hematoxylin and eosin (H&E). Histological staining of muscle: (FIG. 20B) H&E, (FIG. 20C) NADH-TR. Immunofluorescence (IF): (FIG. 20D) DHPR1α, (FIG. 20E), dysferlin. Scale bars=10 µm. (FIG. 20F) Size distribution of TA myofibers by morphometry.

(FIG. 21A) Immunoblot of myotubularin (MTM1, green) and GAPDH (red) from cranial tibialis muscle lysates following injection of XLMTM and unaffected (WT) dogs with either saline or rAAV-MTM1 vector. Lanes 2 and 3, 4 and 5, 6 and 7 show results from control (saline) and vector-treated contralateral limbs, respectively, of three XLMTM dogs. Lane 1: (WT+saline). Lanes 2, 4, 6: (XLMTM+saline). Lanes 3, 5, 7: (XLMTM+rAAV-MTM1). (FIG. 21B) Relative levels by quantitative immunoblotting of myotubularin (normalized to GAPDH) in cranial tibialis muscle after saline injection in unaffected dog (WT), and after vector ($4 \times 10^{11}$ vg) injection in XLMTM dogs. Muscles samples obtained at necropsy (6 weeks), n=2. Samples from vector-treated XLMTM dogs were taken from near the injection site at the center of the cranial tibialis muscle (black) or pooled from the distal and proximal ends of that muscle (grey). The myotubularin level was approximately 60% of WT at the muscle center, and approximately 8% of WT at the ends. (FIG. 21C) Computed tomography (CT) reconstruction at 6 weeks post-injection of treated (+AAV-MTM1) and control (saline) hind limbs of an XLMTM dog. (FIG. 21D) Cranial tibialis muscle mass. Symbols for statistical significance: same as in FIGS. 19A-19H.

(FIG. 22A) Mean myofiber diameters of individual skeletal muscles at 2 weeks and 6 months post-injection. Muscles: TA=tibialis anterior; EDL=extensor digitorum longus; SOL=soleus; TRI=triceps; BI=biceps brachii. (FIG. 22B) Distribution of myofiber diameters of BI muscles at 2 weeks and 6 months post-injection. Numbers of animals: at 2 weeks after injection (WT+saline, n=6), (KO+saline, n=4), (KO+Mtm1, n=3); at 6 months after injection (WT+saline, n=5), (KO+Mtm1, n=5). Symbols for statistics as in FIG. 19.

(FIG. 23A) Nuclei internalization. The percentage of myofibers with internal nuclei was quantified in tibialis anterior muscle. (FIG. 23B) Whole-field actimeter determination of distance traveled in 90 minutes, determined at 12 months. The distance covered by treated mutant mice (mKO+AAV-Mtm1) was not significantly different from that of WT littermates. (FIG. 23C) Specific tetanic force of isolated EDL muscles 12 months after vector delivery. $P<0.01$ (two symbols, ##). In all cases n=7 for (WT+saline), n=5 for (mKO+AAV-Mtm1).

(FIG. 25A) AAV8 vector copy number per chromosome expressed in various muscles from infused XLMTM dogs. (FIG. 25B) Immunoblot of myotubularin (MTM1) and GAPDH from muscle biopsy lysates 4 weeks after rAAV8-MTM1 infusion in XLMTM dogs. Lanes 1 and 8 were loaded with normal (WT) muscle lysates, lanes 2 and 6 from untreated XLMTM muscle lysates, and the remaining lanes loaded with lysates from XLMTM dogs infused with rAAV8-MTM1, with the location of the muscle samples taken from areas indicated by the colored arrows. Muscles samples were obtained at biopsy (4 weeks after infusion)

(FIG. 26A) Hematoxylin and eosin (H&E) and (FIG. 26B) nicotinamide adenine dinucleotide tetrazolium reductase (NADH-TR) staining of muscle cross-sections. Size bars=25 µm. (FIG. 26C) Electron microscopy (EM) shows similar numbers and structure of T-tubules (arrows) and triads (arrowheads) Bar=500 nm.

FIG. 27A depicts the abdominal and thoracic bands worn by the subject. FIG. 27B depicts the exemplary output from the bands.

DETAILED DESCRIPTION OF THE INVENTION

Figures 1A, 1B, 1C, 1D, 1E:
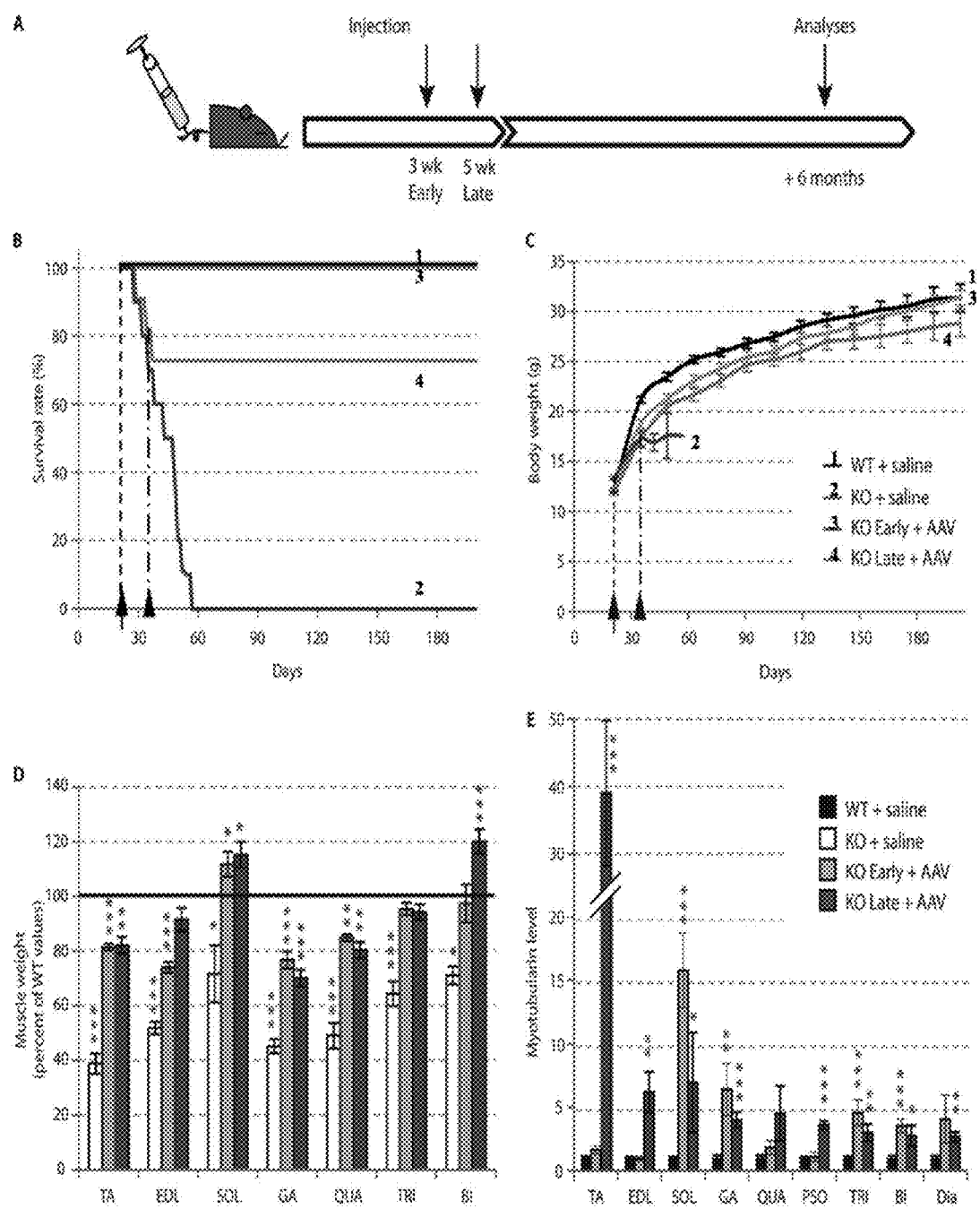
FIGS. 1A-1E depict the results of experiments demonstrating that intravascular delivery of rAAV-Mtm1 in myotubularin-deficient mice improves lifespan and body growth.

The present invention provides compositions and methods for treatment of myopathy in a subject in need thereof. The present invention relates to a strategy of delivering the myotubularin gene (MTM1) to subjects in need of improved muscle function. The compositions and methods of the present invention increase the formation of muscle and improve muscle function in the subject.

In one embodiment, the present invention is useful for treating an individual with a myopathy. In one embodiment, the present invention is useful for treating an individual with X-linked myotubular myopathy (XLMTM). XLMTM is a fatal pediatric disease of skeletal muscle, characterized by a loss of function mutation in MTM1. The present invention improves muscle function and prolongs survival in afflicted subjects. However, the present invention is not limited to subjects having XLMTM. Rather, the present invention is applicable to improving muscle function in any subject in need of improved muscle function.

In one embodiment, the present invention provides a composition that increases the expression of myotubularin in a subject. In one embodiment the composition comprises a nucleic acid comprising a nucleic acid sequence encoding myotubularin. In another embodiment, the composition comprises MTM1. In yet another embodiment, the composition comprises a viral vector comprising a nucleic acid sequence encoding myotubularin. In yet another embodiment, the composition further comprises a mechanism for specific translation of MTM1 within muscle tissue.

The present invention relates to the findings that systemic delivery of an adeno-associated viral vector encoding MTM1 drastically improves muscle function and provides long-term prolonged survival. Thus, the present invention provides non-invasive compositions and methods to treat a myopathy, including XLMTM.

In one embodiment, the present invention provides a method for improving muscle function comprising administering an effective amount of a composition which increases myotubularin expression in a subject. In one embodiment, the method comprises administering to a subject a composition comprising a nucleic acid comprising a nucleic acid sequence encoding myotubularin. In another embodiment, the composition comprises MTM1. In yet another embodiment, the method comprises injection of a composition comprising MTM1 directly into a muscle of a subject in need of improved muscle function. In another embodiment, the method comprises systemic delivery of a composition comprising MTM1 to a subject in need of improved muscle function. In one embodiment, the method provides a sustained elevated level of myotubularin in a subject, which leads to sustained improvements in muscle strength, size, and function.

In another embodiment, the present invention provides a method for prolonging the survival of subjects having a myopathy. The method comprises administering an effective amount of a composition comprising MTM1 to a subject having a myopathy. For example, in one embodiment, the method comprises administering a nucleic acid comprising a nucleic acid sequence encoding myotubularin. In another embodiment, the method comprises injection of a composition comprising MTM1 directly into the muscle of the subject. In another embodiment, the method comprises systemic delivery of a composition comprising MTM1 to the subject. In yet another embodiment, the method provides a sustained elevated level of myotubularin in the subject, which leads to prolonged survival. In a further embodiment, the subject having a myopathy has XLMTM.

In certain embodiments, systemic delivery comprises delivery of the composition to the subject such that composition is accessible throughout the body of the subject. For example, in certain embodiments, systemic delivery comprises enteral, parenteral, oral, intravenous, intra-arterial, and/or inhalational administration. In other embodiments, systemic delivery of the composition comprises administering the composition near a local treatment site (i.e. in a vein or artery nearby a weakened muscle). The present invention relates to the discovery that intravenous administration of a vector comprising MTM1 strengthened muscle regionally and globally. Thus, in certain embodiments, the invention comprises a local delivery of the composition which produces systemic effects. In one aspect, systemic delivery induces improved muscle strength and function in the diaphragm, whose function is critical for quality of life and survival. In certain embodiments, systemic delivery is preferred as local delivery to the diaphragm is invasive and comes with great risk of damaging internal organs.

In certain embodiments, the method comprises a single systemic delivery of a composition comprising MTM1. As described herein, the present invention is partly based upon the discovery that a single systemic delivery of a vector comprising MTM1 produced sustained increases in myotubularin expression and muscle function. In certain embodiments, the method induces increased expression of myotubularin in a subject for a period of time, such as 1 day, 3 days, 1 week, 2 weeks, 1 month, 3 months, 6 months, 1 year, 5 years, or longer. In other embodiments, the method comprises two, three or more systemic deliveries of a composition comprising MTM1, wherein the administrations take place within a period of time, such as 1 day, 3 days, 1 week, 2 weeks, 1 month, 3 months, 6 months, 1 year, 5 years, any fraction or combination of time therein, or longer.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Parenteral" administration of a composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for improving muscle function. In one embodiment, the present invention provides for a treatment of a myopathy. The myopathy may be any form of myopathy, including inherited or acquired myopathies. In one embodiment, the present invention provides compositions and methods for treating X-linked myotubular myopathy (XLMTM). However, the present invention is not limited to treatment of any particular disorder(s). Rather, the invention provides for the ability to improve muscle function in any subject in need of improved muscle function. For example, in one embodiment, the present invention improves muscle function in subjects whose muscles have weakened or atrophied.

The present invention relates to the findings in higher order animal models of XLMTM that systemic delivery of a viral vector comprising the MTM1 gene drastically improves regional and global muscle function and results in prolonged survival. Thus, the compositions and methods described herein are useful in that they provide an easy and efficient treatment of muscular disorders, including XLMTM.

Compositions

The present invention provides a composition that increases the expression of myotubularin, or a biologically fragment thereof, in a muscle. For example, in one embodiment, the composition comprises an isolated nucleic acid sequence comprising MTM1, or a biologically functional fragment thereof. The MTM1 gene encodes myotubularin, a muscle specific protein integral for muscle function. As described herein, delivery of a composition comprising MTM1 improves muscle function. Furthermore, the delivery of a composition comprising MTM1 prolongs survival of a subject having a loss of function mutation in MTM1.

In one embodiment, the composition comprises an isolated nucleic acid comprising a sequence encoding myotubularin, or a biologically functional fragment thereof. In one embodiment, the nucleic acid comprises a sequence comprising at least one of SEQ ID NOs: 1-6. The isolated nucleic acid sequence encoding myotubularin can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned. In one embodiment, the composition In certain embodiments, the composition increases the expression of a biologically functional fragment of myotubularin. For example, in one embodiment, the composition comprises an isolated nucleic acid sequence encoding a biologically functional fragment of myotubularin. In another embodiment, the composition comprises a biologically functional fragment of MTM1. As would be understood in the art, a biologically functional fragment is a portion or portions of a full length sequence that retain the biological function of the full length sequence. Thus, a biologically functional fragment of myotubularin comprises a peptide that retains the function of full length myotubularin. Further, a biologically functional fragment of MTM1 comprises a nucleic acid sequence which encodes myotubularin, or biologically functional fragment thereof.

Further, the invention encompasses an isolated nucleic acid encoding a peptide having substantial homology to the peptides disclosed herein. Preferably, the nucleotide sequence of an isolated nucleic acid encoding a peptide of the invention is "substantially homologous", that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a peptide of the invention.

The present invention also includes a vector in which the isolated nucleic acid of the present invention is inserted. The art is replete with suitable vectors that are useful in the present invention.

In brief summary, the expression of natural or synthetic nucleic acids encoding myotubularin is typically achieved by operably linking a nucleic acid encoding the myotubularin or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In a preferred embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In one embodiment, the myotubularin encoding sequence is contained within an AAV vector. More than 30 naturally occurring serotypes of AAV are available. Many natural variants in the AAV capsid exist, allowing identification and use of an AAV with properties specifically suited for skeletal muscle. AAV viruses may be engineered using conventional molecular biology techniques, making it possible to optimize these particles for cell specific delivery of myotubularin nucleic acid sequences, for minimizing immunogenicity, for tuning stability and particle lifetime, for efficient degradation, for accurate delivery to the nucleus, etc.

Thus, myotubularin overexpression can be achieved in the skeletal muscle by delivering a recombinantly engineered AAV or artificial AAV that contains sequences encoding myotubularin. The use of AAVs is a common mode of exogenous delivery of DNA as it is relatively non-toxic, provides efficient gene transfer, and can be easily optimized for specific purposes. Among the serotypes of AAVs isolated from human or non-human primates (NHP) and well characterized, human serotype 2 is the first AAV that was developed as a gene transfer vector; it has been widely used for efficient gene transfer experiments in different target tissues and animal models. Clinical trials of the experimental application of AAV2 based vectors to some human disease models are in progress, and include therapies for diseases such as for example, cystic fibrosis and hemophilia B. Other useful AAV serotypes include AAV1, AAV3, AAV4, AAV5, AAV6, AAV7, AAV8 and AAV9.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. Thus exemplary AAVs, or artificial AAVs, suitable for expression of myotubularin, include AAV2/8 (see U.S. Pat. No. 7,282,199), AAV2/5 (available from the National Institutes of Health), AAV2/9 (International Patent Publication No. WO2005/033321), AAV2/6 (U.S. Pat. No. 6,156,303), and AAVrh8 (International Patent Publication No. WO2003/042397), among others.

In one embodiment, the vectors useful in the compositions and methods described herein contain, at a minimum, sequences encoding a selected AAV serotype capsid, e.g., an AAV8 capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV8 origin. Alternatively, vectors may be used in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199.

The AAV vectors of the invention further contain a minigene comprising a myotubularin nucleic acid sequence as described above which is flanked by AAV 5' (inverted terminal repeat) ITR and AAV 3' ITR.

A suitable recombinant adeno-associated virus (AAV) is generated by culturing a host cell which contains a nucleic acid sequence encoding an adeno-associated virus (AAV) serotype capsid protein, or fragment thereof, as defined herein; a functional rep gene; a minigene composed of, at a minimum, AAV inverted terminal repeats (ITRs) and a myotubularin nucleic acid sequence, or biologically functional fragment thereof; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

In specific embodiments, such a stable host cell will contain the required component(s) under the control of a constitutive promoter. In other embodiments, the required component(s) may be under the control of an inducible promoter. Examples of suitable inducible and constitutive promoters are provided elsewhere herein, and are well known in the art. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfers the sequences carried thereon. The selected genetic element may be delivered using any suitable method, including those described herein and any others available in the art. The methods used to construct any embodiment of this invention are known to those with skill in nucleic acid manipulation and include genetic engineering, recombinant engineering, and synthetic techniques (see, e.g., Sambrook et al, Molecular Cloning: A Laboratory Manual, Cold Spring Harbor Press, Cold Spring Harbor, N.Y.). Similarly, methods of generating rAAV virions are well known and the selection of a suitable method is not a limitation on the present invention (see, e.g., K. Fisher et al, 1993 J. Virol., 70:520-532 and U.S. Pat. No. 5,478,745, among others).

Unless otherwise specified, the AAV ITRs, and other selected AAV components described herein, may be readily selected from among any AAV serotype, including, without limitation, AAV1, AAV2, AAV3, AAV4, AAV5, AAV6, AAV7, AAV8, AAV9 or other known or as yet unknown AAV serotypes. These ITRs or other AAV components may be readily isolated from an AAV serotype using techniques available to those of skill in the art. Such an AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

The minigene is composed of, at a minimum, a myotubularin encoding nucleic acid sequence (the transgene) and its regulatory sequences, and 5' and 3' AAV inverted terminal repeats (ITRs). In one desirable embodiment, the ITRs of AAV serotype 2 are used. However, ITRs from other suitable serotypes may be selected. It is this minigene which is packaged into a capsid protein and delivered to a selected host cell. The myotubularin encoding nucleic acid coding sequence is operatively linked to regulatory components in a manner which permits transgene transcription, translation, and/or expression in a host cell.

In addition to the major elements identified above for the minigene, the AAV vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In one embodiment, the vector of the invention comprises a tissue-specific promoter to drive expression of myotubularin in one or more specific types of cells. In one embodiment, the vector of the invention comprises a tissue-specific promoter to drive expression of myotubularin specifically in muscle. Tissue-specific promoters, which can be included in the vector of the invention to drive expression specifically in muscle are known in the art, and include, but are not limited to a desmin promoter, myoglobin promoter, muscle creatine kinase promoter, mammalian troponin 1 promoter, and skeletal alpha-action promoter. For example, in one embodiment, the vector comprises the desmin promoter to provide expression of myotubularin specifically in muscle cells.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector. For example, in one embodiment, the vector of the invention comprises a muscle-specific enhancer to enhance myotubularin expression specifically in muscle. Tissue-specific enhancers, which can be included in the vector of the invention to drive expression specifically in muscle are known in the art, and include, but are not limited to a desmin enhancer, muscle creatine kinase enhancer, myosin light-chain enhancer, myoglobin enhancer, and mammalian troponin 1 internal regulatory element.

In order to assess the expression of myotubularin, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially.

In general, the construct with the minimal 5' flanking region showing the highest level of expression of reporter gene is identified as the promoter. Such promoter regions may be linked to a reporter gene and used to evaluate agents for the ability to modulate promoter-driven transcription.

In one embodiment, the composition comprises a naked isolated nucleic acid encoding myotubularin, or a biologically functional fragment thereof, wherein the isolated nucleic acid is essentially free from transfection-facilitating proteins, viral particles, liposomal formulations and the like (see, for example U.S. Pat. No. 5,580,859). It is well known in the art that the use of naked isolated nucleic acid structures, including for example naked DNA, works well with inducing expression in muscle. As such, the present invention encompasses the use of such compositions for local delivery to the muscle and for systemic administration (Wu et al., 2005, Gene Ther, 12(6): 477-486).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol.

"Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the composition of the present invention comprises a peptide comprising myotubularin protein, or biologically functional fragment thereof. The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The invention should also be construed to include any form of a peptide having substantial homology to the peptides disclosed herein. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the peptides disclosed herein.

The peptide may alternatively be made by recombinant means or by cleavage from a longer polypeptide. The composition of a peptide may be confirmed by amino acid analysis or sequencing.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation.

The term "functionally equivalent" as used herein refers to a polypeptide according to the invention that preferably retains at least one biological function or activity of the specific amino acid sequence of myotubularin.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of the myotubularin comprising peptide.

A peptide or protein of the invention may be phosphorylated using conventional methods such as the method described in Reedijk et al. (The EMBO Journal 11(4):1365, 1992). Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

(a) Tags: In a particular embodiment of the invention, the polypeptide of the invention further comprises the amino acid sequence of a tag. The tag includes but is not limited to: polyhistidine tags (His-tags) (for example H6 and H10, etc.) or other tags for use in IMAC systems, for example, $Ni^{2+}$ affinity columns, etc., GST fusions, MBP fusions, streptavidine-tags, the BSP biotinylation target sequence of the bacterial enzyme BIRA and tag epitopes that are directed by antibodies (for example c-myc tags, FLAG-tags, among others). As will be observed by a person skilled in the art, the tag peptide can be used for purification, inspection, selection and/or visualization of the fusion protein of the invention. In a particular embodiment of the invention, the tag is a detection tag and/or a purification tag. It will be appreciated that the tag sequence will not interfere in the function of the protein of the invention.

(b) Leader and secretory sequences: Accordingly, the polypeptides of the invention can be fused to another polypeptide or tag, such as a leader or secretory sequence or a sequence which is employed for purification or for detection. In a particular embodiment, the polypeptide of the invention comprises the glutathione-S-transferase protein tag which provides the basis for rapid high-affinity purification of the polypeptide of the invention. Indeed, this GST-fusion protein can then be purified from cells via its high affinity for glutathione. Agarose beads can be coupled to glutathione, and such glutathione-agarose beads bind GST-proteins. Thus, in a particular embodiment of the invention, the polypeptide of the invention is bound to a solid support. In a preferred embodiment, if the polypeptide of the invention comprises a GST moiety, the polypeptide is coupled to a glutathione-modified support. In a particular case, the glutathione modified support is a glutathione-agarose bead. Additionally, a sequence encoding a protease cleavage site can be included between the affinity tag and the polypeptide sequence, thus permitting the removal of the binding tag after incubation with this specific enzyme and thus facilitating the purification of the corresponding protein of interest.

(c) Targeting sequences: The invention also relates to peptides comprising myotubularin fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e. are heterologous).

A target protein is a protein that is selected for degradation and for example may be a protein that is mutated or over expressed in a disease or condition. In another embodiment of the invention, a target protein is a protein that is abnormally degraded and for example may be a protein that is mutated or underexpressed in a disease or condition. The targeting domain can be a membrane spanning domain, a membrane binding domain, or a sequence directing the protein to associate with for example vesicles or with the nucleus. The targeting domain can target a peptide to a particular cell type or tissue. For example, the targeting domain can be a cell surface ligand or an antibody against cell surface antigens of a target tissue (e.g. muscle tissue). A targeting domain may target the peptide of the invention to a cellular component.

(d) Intracellular targeting: Combined with certain formulations, such peptides can be effective intracellular agents. However, in order to increase the efficacy of such peptides, the peptide of the invention can be provided a fusion peptide along with a second peptide which promotes "transcytosis", e.g., uptake of the peptide by epithelial cells. To illustrate, the peptide of the present invention can be provided as part of a fusion polypeptide with all or a fragment of the N-terminal domain of the HIV protein Tat, e.g., residues 1-72 of Tat or a smaller fragment thereof which can promote transcytosis. In other embodiments, the RLP can be provided a fusion polypeptide with all or a portion of the antenopedia III protein.

To further illustrate, the peptide of the invention can be provided as a chimeric peptide which includes a heterologous peptide sequence ("internalizing peptide") which drives the translocation of an extracellular form of the peptide across a cell membrane in order to facilitate intracellular localization of the peptide. In this regard, the peptide is one which is active intracellularly. The internalizing peptide, by itself, is capable of crossing a cellular membrane by, e.g., transcytosis, at a relatively high rate. The internalizing peptide is conjugated, e.g., as a fusion protein, to a peptide comprising myotubularin. The resulting chimeric peptide is transported into cells at a higher rate relative to the peptide alone to thereby provide a means for enhancing its introduction into cells to which it is applied.

(e) Peptide Mimetics:

In other embodiments, the subject compositions are peptidomimetics of the peptide of the invention. Peptidomimetics are compounds based on, or derived from, peptides and proteins. The peptidomimetics of the present invention typically can be obtained by structural modification of a known sequence using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into non-peptide compounds with the activity of the parent peptides.

Moreover, as is apparent from the present disclosure, mimetopes of the subject peptides can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p123), C-7 mimics (Huffman et al. in Peptides: Chemistry and Biologyy, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), β-aminoalcohols (Gordon et al. (1985) Biochem Biophys Res Commun 126:419; and Dann et al. (1986) Biochem Biophys Res Commun 134:71), diaminoketones (Nataraj an et al. (1984) Biochem Biophys Res Commun 124:141), and methyleneamino-modifed (Roark et al. in Peptides: Chemistry and Biology, G. R. Marshall ed., ESCOM Publisher: Leiden, Netherlands, 1988, p134). Also, see generally, Session III: Analytic and synthetic methods, in Peptides: Chemistry and Biology, G. R. Marshall ed., ESCOM Publisher: Leiden, Netherlands, 1988)

In addition to a variety of side chain replacements which can be carried out to generate the peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of binding to the peptide of the invention. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling, the predicted mimetope structures can then be produced by, for example, chemical synthesis, recombinant DNA technology, or by isolating a mimetope from a natural source (e.g., plants, animals, bacteria and fungi).

A peptide of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, 2$^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.) By way of example, a RLP or chimeric protein may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain the myotubularin comprising peptide or chimeric protein fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Dosage and Formulation (Pharmaceutical Compositions)

The present invention envisions treating a disease, for example, myopathy and the like, in a subject by the administration of therapeutic agent, e.g. a composition comprising MTM1.

Administration of the therapeutic agent or modified cell in accordance with the present invention may be continuous or intermittent, depending, for example, upon the recipient's physiological condition, whether the purpose of the administration is therapeutic or prophylactic, and other factors known to skilled practitioners. The administration of the agents or modified cell of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent or modified cell may be directly injected into the muscle.

The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampoules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyl-dioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in an mammal body to achieve a particular effect (see, e.g., Rosenfeld et al., 1991; Rosenfeld et al., 1991 a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

Gene Therapy Administration

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein the vector is complexed to another entity, such as a liposome, aggregated protein or transporter molecule.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

Cells containing the therapeutic agent may also contain a suicide gene i.e., a gene which encodes a product that can be used to destroy the cell. In many gene therapy situations, it is desirable to be able to express a gene for therapeutic purposes in a host, cell but also to have the capacity to destroy the host cell at will. The therapeutic agent can be linked to a suicide gene, whose expression is not activated in the absence of an activator compound. When death of the cell in which both the agent and the suicide gene have been introduced is desired, the activator compound is administered to the cell thereby activating expression of the suicide gene and killing the cell. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

Therapeutic

The present invention encompasses a method to treat myopathy in a subject diagnosed with a myopathy or in a subject at risk for developing a myopathy. The method improves muscle strength and muscle function in those in need thereof. Further, the method improves quality of life and prolongs survival in a patient with a myopathy. In one embodiment, the method of the present invention comprises administering to a subject a composition comprising the MTM1 gene or functional fragment thereof. In another embodiment, the method of the present invention comprises administering to a subject a composition comprising a nucleic acid sequence encoding myotubularin. In another embodiment, the method comprises inducing the expression of myotubularin specifically in the muscle of the subject. In one embodiment, the subject is a mammal. Preferably the mammal is a human.

The method of the present invention is used to treat any type of myopathy in a subject. A myopathy is a muscular disease wherein the muscle fibers of an afflicted subject are not functioning normally. Non-functional, partially-functional, or sub-optimally-functional muscle fibers lead to overall muscle weakness, which may result in loss of motor function and respiratory control. In one embodiment, the method of the present invention is used to treat acute myopathies that may occur, for example, as a symptom in systemic disease processes. In another embodiment, the method of the present invention is used to treat chronic myopathy, including inherited myopathies or dystrophies.

Muscular dystrophies are a subgroup of myopathy characterized, generally, by progressive weakening of muscle tissue through increased muscle degeneration and reduced muscle regeneration. Muscular dystrophies are generally inherited, with specific forms of muscular dystrophy following specific patterns of inheritance. Forms of muscular dystrophy include Duchenne muscular dystrophy, Becker's muscular dystrophy, congenital muscular dystrophy, distal muscular dystrophy, distal muscular dystrophy, Miyoshi myopathy, Limb Girdle Muscular Dystrophy, Emery-Dreifuss muscular dystrophy, Facioscapulohumeral muscular dystrophy, myotonic muscular dystrophy, and oculopharyngeal muscular dystrophy.

Congenital myopathies are another subgroup of inherited myopathies that do not include progressive muscle death, as seen in dystrophies, but rather is associated with reduced contraction of the muscle tissue. Forms of congenital myopathy include namaline myopathy, multi/minicore myopathy, and myotubular myopathy. Myotubular myopathy is a rare disorder that in many cases presents in infants, with afflicted subjects having low muscle tone, severe weakness, delayed development, and pulmonary complications. Inheritance of myotubular myopathy includes forms that are X-linked, autosomal recessive, and autosomal dominant. The X-linked form (XLMTM) is the most common form of myotubular myopathy, and has a life expectancy of only a few years. XLMTM is caused by genetic mutations in the MTM1 gene, with the severity of the disease dependent on the particular type of mutation. The present invention is based upon the delivery of functional MTM1, which thereby restores proper muscle function. As described elsewhere herein, administration of MTM1 improves muscle function and prolongs survival in afflicted subjects.

The present method is not limited to treatment of any particular myopathy, as it is contemplated herein that enhanced expression of myotubularin improves muscle function of a wide variety of disorders. Further, the present method is not limited to treatment of a subject who is clinically diagnosed with any particular disorder. For example, in one embodiment, the method comprises administering a composition comprising MTM1 to a subject in need of improved muscle function. This can include subjects who have been bedridden or otherwise immobile, causing their muscles to atrophy.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials. When "an effective amount" or "therapeutic amount" is indicated, the precise amount of the compositions of the present invention to be administered can be determined by a physician with consideration of individual differences in age, weight, disease progression, and condition of the patient (subject). The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the method of the invention comprises a systemic administration of a composition comprising MTM1. In certain embodiments, systemic delivery comprises administration at or near weakened or afflicted muscle. For example, in one embodiment, systemic delivery comprises intravenous delivery near a weakened tissue. However, it is demonstrated herein that this delivery produces regional increases in muscle function, at or near the site of delivery, as well as global increases in muscle functions in other parts of the body. Thus, in certain embodiments, the invention comprises a local delivery of the composition which produces systemic effects. In other embodiments, systemic delivery comprises administration at a distance from any weakened or afflicted muscle. In certain instances, a systemic delivery is preferred as it is demonstrated herein that systemic delivery of MTM1 effectively improves regional and global muscle function throughout the subject. Thus, systemic delivery eliminates the need for a multitude of local deliveries, and allows for efficient induction of myotubularin expression in muscle tissue that may be difficult to reach using local delivery methods (e.g. diaphragm). As demonstrated herein, systemic delivery improves muscle function in the affected diaphragm. Thus, systemic delivery of the composition described herein improves respiratory function without the need for direct injection into the diaphragm. This thereby provides an easy, non-invasive and effective treatment method that can vastly improve survival and quality of life of an afflicted subject.

In certain embodiments of the present invention, the composition, as described herein, are administered to a subject in conjunction with (e.g. before, simultaneously, or following) any number of relevant treatment modalities, including but not limited to immunosuppressive agents, supportive therapy, respiratory support, nutritional support, orthopedic support, and the like.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Gene Replacement Therapy Prolongs Survival and Restores Muscle Function in Murine and Canine Models of X-Linked Myotubular Myopathy Loss-of-function mutations in the myotubularin gene (MTM1) cause X-linked myotubular myopathy (XLMTM), a fatal pediatric disease of skeletal muscle with no effective treatment. Described herein is examination of gene therapy in mouse and dog models of XLMTM. Systemic delivery of a single dose of a recombinant adeno-associated virus (rAAV) vector expressing murine myotubularin in Mtm1-deficient knockout mice resulted in robust improvement in motor activity and contractile force, attenuated pathology and prolonged survival from under two months to at least one year. Intramuscular and intravascular rAAV-mediated delivery of canine MTM1 in affected XLMTM dogs resulted in similar robust improvement in muscle contractile force, attenuated pathology and prolonged survival. The results presented herein demonstrate that myotubularin gene delivery rescues severe muscle pathology in mutant animals, providing proof-of-concept for future clinical trials in XLMTM patients.

It was examined whether restoration of functional myotubularin would ameliorate the severe muscular weakness. Described herein is the long-term impact of systemic delivery of a rAAV-Mtm1 vector in myotubularin-deficient mice.

To bridge the translational gap between mice and men, a canine breeding colony was established from a female Labrador Retriever carrying an X-linked MTM1 missense mutation (Beggs et al., 2010, Proc Natl Acad Sci USA 107(33):14697-702). Muscles from affected males exhibit profound quantitative reduction and altered localization of myotubularin, likely due to sequestration and degradation of misfolded protein. The physiological defects closely resemble those of humans with comparably severe mutations. Reported herein are the results of rAAV-mediated myotubularin transduction in limb muscles of six XLMTM dogs as the first large animal predictive model of gene therapy for this disease.

The materials and methods employed in these experiments are now described.

Animals

The constitutive (whole-body) knockout of the myotubularin gene (KO-Mtm1, also named BS53d4-129pas) and the muscle-specific knockout (mKO-Mtm1) on the C57BL/6 background were described previously (Buj-Bello et al., 2002, Proc Natl Acad Sci USA 99(23):15060-5; Al-Qusairi et al., 2009, Proc Natl Acad Sci USA 106(44):18763-8). Wild-type littermate males were used as controls.

XLMTM dogs were described previously (Beggs et al., 2010, Proc Natl Acad Sci USA 107(33):14697-702). Affected males were identified by polymerase chain reaction-based genotyping, as described.

Preparation and Intravascular Delivery rAAV-Mtm1 in Mice

The recombinant adeno-associated virus vectors rAAV2/8-pDesmin-Mtm1$^{murine}$ and rAAV2/9-pDesmin-Mtm1$^{murine}$ were constructed as follows. Murine Mtm1 cDNA (AF073996, NCBI) was cloned downstream of the human desmin promoter (Wang et al., Mol Ther 15(6):1160-6) in the AAV2 expression plasmid pAAV2-pDes by PCR amplification. All clones were verified by DNA sequencing. Pseudo-typed recombinant rAAV2/8 and rAAV2/9 viral preparations were generated by packaging AAV2-inverted terminal repeat (ITR) recombinant genomes into AAV8 or AAV9 capsids. Briefly, the cis-acting plasmid encoding the transgene pAAV-pDesmin-Mtm1, the trans-complementing rep-cap9 plasmid encoding the proteins necessary for the replication and the structure of vector and the adenovirus helper plasmid cells were transfected together into HEK293 cells. After three days, both the culture supernatant and the monolayer cells were harvested and cells were broken by repetitive freeze-and-thaw cycles. Vector particles were purified through two sequential rounds of CsCl gradient ultra-centrifugation and dialyzed against sterile PBS. Viral titers were quantified by a TAQMAN® real-time PCR assay (Applied Biosystem) with primers and probes specific for the ITR2 regions (Qiao et al., 2009, Hum Gene Ther 20(1):1-10) and expressed as viral genomes per ml (vg/ml).

rAAV-Mtm1 at $3 \times 10^{13}$ viral genomes per kg body mass [(vg/kg)] was injected into the tail vein of 3- and 5-week-old KO-Mtm1 mice. An equivalent volume of saline was administrated to either KO-Mtm1 or wild-type (WT) animals as controls. The same vector ($0.5 \times 10^{13}$ vg/kg) or an equivalent volume of saline was injected into the tail vein of 4 week-old mKO-Mtm1 or WT littermate mice.

Preparation and Administration of rAAV8-MTM1 in Dogs

The recombinant adeno-associated virus vector containing a canine myotubularin cDNA regulated by the desmin promoter, rAAV2/8-pDesmin-MTM1$^{canine}$ (designated rAAV8-MTM1), was produced in a baculovirus/Sf9 system. Two baculovirus batches were generated, one expressing rep and cap AAV genes and the second bearing the canine MTM1 cDNA (XM850116, NCBI) downstream from the human desmin promoter (pDesmin). The rAAV-MTM1 vector particles were produced after baculoviral double infection of insect Sf9 cells and purified from total cell culture using AVB affinity chromatography column (GE Healthcare, AVB SEPHAROSE® high performance). The concentration in vg/mL was determined from DNase-resistant particles, as described above. Other routine quality control assays for rAAV vectors were performed, including sterility and purity tests (Yuasa et al., 2007, Gene Ther 14(17):1249-60).

Intramuscular Injections.

rAAV8-MTM1 ($4 \times 10^{11}$ vg) diluted in 1 ml lactated Ringer's solution was injected under ultrasound guidance into the midbelly of the cranial tibialis muscle of one hind limb of unvaccinated 10 weeks-of-age affected male XLMTM dogs under anesthesia. The cranial tibialis muscle of the contralateral limb was injected with an equal volume of Ringer's solution alone. Unaffected male littermates (WT) received 1 ml of Ringer's solution in each hind limb.

Intravenous Regional Limb Infusions.

In anesthetized XLMTM dogs rAAV8-MTM1 ($2.5 \times 10^{13}$ vg/kg) diluted in phosphate buffered saline (PBS) was infused into the distal saphenous vein under pressure (300 torr) against a tourniquet as described (Petrov et al., 2011, Methods Mol Biol 709:277-86; Arruda et al., 2010, Blood 115(23):4678-88). Briefly, a tourniquet was positioned at the level of the groin and adjusted until the femoral pulse was no longer detectable by ultrasound to transiently block blood inflow to the target limb. A tight extensible wrap applied in a distal to proximal direction exsanguinated the limb before the tourniquet was tightened. Vector was suspended in PBS at 20% of the total hind limb volume (determined by water volume displacement) and administered via a 14 gauge catheter placed into a distal branch of the peripheral saphenous vein on the dorsum of the paw. The tourniquet was tightened for a total of 15 minutes (10 minutes prior to and 5 minutes during the infusion). In each dog, one hind limb was infused with vector whereas the contralateral hind limb was not infused.

Mtm1 Nucleic Acid Sequences

Mtm1 nucleic acid sequences are as follows: mouse Mtm: SEQ ID NOs 1-2; canine MTM1: SEQ ID NOs 3-4; and human MTM1: SEQ ID NOs 5-6.

Vector Copy Number (VCN) Analysis

The number of vector genomes per diploid genome was quantified from 80 ng of total DNA by TAQMAN® real-time PCR with a 7900 HT thermocycler (Applied Biosystems). The canine β glucuronidase gene was used for standardization. The primers and probe used for vector genome (MTM1) amplification were as follows: 5'-ATAAGTTTTGGACATAAGTTTGC-3' (forward, SEQ ID NO: 7), 5'-CATTTGCCATACACAATCAA-3' (reverse, SEQ ID NO:8), and 5'-CGACGCTGACCGGTCTCCTA-3' (probe, SEQ ID NO:9). The primers (Applied Biosystems) and probe used for β glucuronidase amplification were as follows: 5'-ACGCTGATTGCTCACACCAA-3' (forward, SEQ ID NO:10), 5'-CCCCAGGTCTGCTTCATAGTTG-3' (reverse, SEQ ID NO:11), and 5'-CCCGGCCCGTGAC-CTTTGTGA-3' (probe, SEQ ID NO:12).

Quantitative Immunoblot Analysis

Several muscle cryo-sections of thirty μm each (300 μm to 1 mm in total) were sliced and proteins were extracted using a lysis buffer containing 10 mM Tris-HCl pH 7,4, 150 mM NaCl, 1 mM EDTA, 1 mM EGTA, 2 mM Na orthovanadate, 100 mM NaF, 4 mM sodium pyrophosphate, 1% Triton X-100, 0.5% IGEPAL, and Protease Inhibitor Cocktail used according to the manufacturer's instruction (Roche Applied Science). Samples were incubated on ice with occasional mixing during 30 min. After centrifugation at 10,000 g for 10 min at 4° C., the supernatants were recovered for Western Blot analysis. Total protein concentration was determined by the Bradford methodology according to the manufacturer's instruction (BioRad). Thirty to sixty μg of total proteins were denatured for 5 min at 95° C. in a buffer containing 125 mM Tris.HCl pH 6.8, 4% SDS, 0.2M DTT, 50% glycerol and bromophenol blue. Protein samples were submitted to sodium dodecyl sulfate-polyacrylamide gel electrophoresis in 10% acrylamide gels and transferred onto 0.2 μm nitrocellulose membranes (GE Healthcare) by the application of an electric field (100 V, 1 hour) at 4° C. The membranes were first incubated for 60 min at room temperature in a blocking solution composed of Tris-buffered-saline (TBS), 0.1% Tween 20 and 5% milk. For mouse studies, membranes were probed successively with a rabbit polyclonal antibody raised against the C-terminal extremity of murine myotubularin (R2348 (Buj-Bello et al., 2008, Hum Mol Genet 17(14):2132-43)) and a mouse monoclonal antibody specific for GAPDH (Millipore, MAB374). For dog studies, membranes were probed with a rabbit polyclonal antibody raised against the C-terminus of canine myotubularin (R1040, Généthon). Antibody incubations were carried out overnight at 4° C. in TBS, 0.1% Tween 20 and 5% milk. Detection was performed with a secondary antibody coupled to IRDye 680 (LI-COR) and the membranes were exposed to the ODYSSEY® infrared imaging system (LI-COR Biotechnology Inc.) for detection and quantification of the fluorescence signal (ODYSSEY® software). All gel electrophoresis, transfer and blotting procedures were repeated to produce three independent immunoblots for each sample. ImageJ densitometry software (Version 1.4, National Institute of Health, Bethesda, Md.) was also used to measure density of immunoblot bands (Maulik and Thirunavukkarasu, 2008, J Mol Cell Cardioln 44(2):219-27; Tsunoda et al., 2008, Am J Physiol Endocrinol Metab 294(5):E833-40; Fukushima et al., 2007, BMC Musculoskelet Disord 8:54). Optical density for each band was measured three times and values were averaged.

Histology, Morphometry, Immunofluorescence, Electron Microscopy

For mouse studies, serial 7 μm thick transverse cryosections were prepared from frozen muscles and processed for hematoxylin and eosin (HE) staining using standard procedures. The proportion of internalized nuclei was quantified from HE-stained sections using the Histolab software (Microvision). For NADH-TR coloration muscle cryo-sections were incubated for 10 min at 57° C. in a solution composed of 50 mM Tris HCl, pH 7.3, 1.2 mM Nitroblue Tetrazolium (sigma) and 0.6 mM β-NADH (Sigma), washed, and mounted in EUKITT® (Fluka). For determination of the number and minimal diameter of myofibers, laminin immuno-staining was performed to delineate each fiber. Briefly, endogenous peroxidases were neutralized by incubation in $H_2O_2$ for 30 min. Sections were incubated for 30 minutes with PBS/10% goat serum in order to block unspecific sites and then overnight in a 1:1,000 dilution of anti-laminin rabbit polyclonal antibody (DAKO, Z0097) at room temperature. Sections were then processed according to manufacturer's guidelines (Kit En Vision™ Rabbit HRP, DAKO). Myofibers minor diameters were automatically measured on digital images of the sections by the Ellix software (Microvision).

For immunofluorescence staining of mouse and dog muscle tissue, transverse sections were fixed for 10 min by incubation in PBS at 100° C. Non-specific antigens were blocked with PBS, 0.2% Tween, 3% BSA at RT. Sections were then incubated at 4° C. overnight with mouse primary antibodies directed against DHPR1α (Thermo Scientific Pierce, MA3-920) or Dysferlin (Novocastra, NCL-HAM-LET). After extensive PBS washes, sections were incubated with biotinylated goat anti mouse antibodies (SouthernBiotech) and, after additional washes, with streptavidin conjugated with ALEXA FLUOR® 488 (Invitrogen). Glass slides were mounted with FLUORSAVE™ reagent (Calbiochem®, Merck) and visualized with a Leica confocal microscope TCS-SP2. Digital images of a slice corresponding to the muscle midsection were acquired with a CCD camera (Sony) and a motorized stage.

For histological studies of canine tissue following intramuscular injection, serial 8 μm thick transverse cryo-sections were prepared from frozen mid tibialis anterior muscles and processed for hematoxylin and eosin (HE) and NADH-TR staining, as described above. The number of centrally nucleated fibers, and fibers with mislocalization of organelles (including mitochondrial aggregates and necklace fibers) were quantified manually from photographs taken at 200× magnification. The number of fibers assessed ranged from 200-861. For fiber size quantification, muscles were immunostained as described above with rabbit anti-dystrophin antibodies (Abcam PLC, ab 15277) and ALEXA FLUOR®-conjugated anti-rabbit IgG (Molecular Probes). Staining was evaluated and MinFeret diameters of fibers were quantified using a Nikon Eclipse 90i microscope using NIS-Elements AR software (Nikon Instruments Inc.). Immunofluorescence staining was performed as described above for mouse muscle samples. For histological studies of canine tissue following intravascular infusion of rAAV-MTM1, biopsies of the quadriceps muscles from the infused and non-infused limb were taken at 14 and 27 weeks of life from 3 normal dogs and 3 treated XLMTM dogs. Sectioning and staining was using HE and NADH were performed as described above. Fiber size, internal nucleation, and organellar localization were measured and quantified manually using an BX53 microscope and CellSens Standard software (Olympus). The number of fibers assessed ranged from 256 to 695.

For ultrastructural studies, a small portion of the mid-tibialis anterior muscle from 2 normal dogs and 2 XLMTM dogs was fixed in 5% glutaraldehyde, 2.5% paraformaldehyde in 0.2 mmol/L of cacodylate buffer, pH 7.4. Fixed tissue was then subjected to osmication, stained using uranyl acetate, dehydrated in alcohol, and embedded in TAAB Epon (Merivac Ltd.). Subsequently, 1 μm scout sections were evaluated and areas of interest were cut at 95 nm thickness using an ultracut microtome (Leica Camera AG), picked up on 100 m formvar-coated copper grids, stained with 0.2% lead citrate, and post-stained with uranyl acetate to improve resolution of the transverse (T) and (L) longitudinal tubules of the sarcotubular system. Tissue was viewed and imaged using a TECNAI™ BioTwin Spirit Electron Microscope (FEI Co.). The number of T and L tubules was quantified manually by evaluation of one representative 6800× image from each myofiber within 1 or 2 well-oriented specimens. The number of myofibers quantified ranged from 6-11 fibers per specimen for WT animals and 7-12 myofibers per specimen for XLMTM dogs.

Computerized Tomography (CT) Analysis of Canine Muscle

Digital data from anesthetized affected male XLMTM dogs (n=3) and normal male littermates (n=3) were obtained from 0.5 mm serial whole-body CT images (General Electric 8800) taken at the end of the study, just prior to necropsy. An investigator blinded to the experimental intervention traced the area of interest in each image using a digital pen (Cintiq, Wacom). Image settings were kept consistent to minimize variance among tracings. Digital area and volume measurements (Li et al., 2008, Vet Parasitol 157(1-2):50-8) of muscles were obtained as described (Wang et al., 2008, Gene Ther 15(15):1099-106) using OsiriX, an open-source software (Bretag, 2007, Nature 450(7173):E23; discussion E23-5).

Immune Response Profile of Canines Following rAAV8-MTM1

Humoral Immune Response to Vector:

Enzyme-linked immunosorbent assay (ELISA) was used to detect the IgG and IgM antibodies specific to AAV8 vector in sera of dogs, as previously described for humans (Boutin et al., 2010, Hum Gene Ther 21(6):704-12; Monteilhet et al., 2011, Mol Ther 19(11):2084-91). These ELISA were revealed by a colorimetric amplification system based on alkaline phosphatase and results expressed as titer. A neutralizing assay was employed to detect neutralizing factors (NAF) specific to AAV8 in dog sera, as previously described for human sera (Boutin et al., 2010, Hum Gene Ther 21(6):704-12; Monteilhet et al., 2011, Mol Ther 19(11):2084-91). Briefly, vectors and serum were mixed under appropriate conditions and inoculated into cell culture susceptible to the vector. The loss of infectivity was brought about by interference by the bound antibody with any one of the steps leading to the release of the viral genome into the host cells. The values are presented as percentage of transgene activity compared to transduction of an equal amount of vectors without serum pre-incubation. The neutralizing titer was determined as the serum dilution at which 50% or higher inhibition occurred.

Humoral Immune Response to MTM1 Transgene:

Customized ELISA assays were developed to detect the IgG and IgM antibodies specific of MTM1 protein in sera of animals. For that, purified canine MTM1 protein was used. These ELISA were revealed by a colorimetric amplification system based on alkaline phosphatase and results were expressed as titer.

Cellular Immune Response to AAV Vectors:

Cellular response specific to AAV in dog was by IFNγ ELIspot assays, as previously described for humans (Herson et al., 2012, Brain 135(Pt 2):483-92). Briefly, frozen peripheral blood mononuclear cells (PBMC) were plated into an IFNγ precoated 96-well ELIspot plate, and incubated in the presence of lentiviral vectors coding for VP1, VP2 and VP3 capsid proteins of AAV (LV-Cap8). Results were expressed as spot-forming units/$10^6$ cells. Samples were considered positive for AAV if the number of spots was greater than 1.8 times the corresponding control with LV-empty.

Cellular Immune Response to MTM1 Transgene:

Cellular response specific to MTM1 was measured by ELIspot assays in dogs. Frozen PBMCs were plated into an IFNγ precoated 96-well ELIspot plate, and incubated in the presence of lentiviral vectors coding for the whole MTM1 protein (LV-MTM1). Results were expressed as spot-forming units/$10^6$ cells. Samples were considered positive for MTM1 if the number of spots was greater than 1.8 times the corresponding control with LV-empty.

Inflammatory Immune Response:

Quantification for IL2, IL6, IL8, IL10, IL15, IFNγ and TNFα was performed at various time points pre- and post-vector administration, by Luminex technology as described (Skogstrand, 2012, Methods 56(2):204-12; Malekzadeh et al., 2012, Methods 56(4):508-13).

Muscle Function

Actimeter Test

Spontaneous locomotor activity in mice was assessed using the LE 8811 IR motor activity monitor (Bioseb). Briefly, mice were placed in an open field bounded with 16 horizontal photoelectric Infra Red beams to measure three-dimensional movements of the animals. The distance crossed was recorded and analyzed for 90 minutes.

Escape Test

Global strength of mice was evaluated by the "escape test" (Carlson and Makiejus, 1990, Muscle Nerve 13(6): 480-4). Briefly, mice were placed on a platform facing the entrance of a 30 cm tube. A cuff wrapped around the tail was connected to a fixed force transducer and the mice were induced to escape within the tube in the direction opposite from the force transducer by a gentle pinching of the tail. The mouse's forward flight induces a short peak of force. The average of the five highest force peaks, normalized to body mass, was reported.

EDL Contractile Force in Mice

Measurements of isometric contractile properties of murine EDL muscles were performed in vitro as described (Buj-Bello et al., 2008, Hum Mol Genet 17(14):2132-43). Animals were anesthetized by intra-peritoneal injection of pentobarbital (50 mg/kg). The muscles were surgically excised and soaked in an oxygenated Krebs solution maintained at 20° C. Muscles were connected at one end to an electromagnetic puller and at the other end to a force transducer, and stimulation was delivered through electrodes running parallel to the muscle. Twitch and tetanic (125 HZ, 300 ms) isometric contractions were recorded at $L_0$ (the length at which maximal tetanic isometric force is observed). For comparative purposes, normalized isometric force was assessed. Isometric specific force (tension) was calculated by dividing the force by the estimated cross-sectional area of the muscle (Dubey et al., 2007, Vet Parasitol 149(3-4):158-66).

Hind Limb Contraction in Dogs

Figures 25A, 25B:
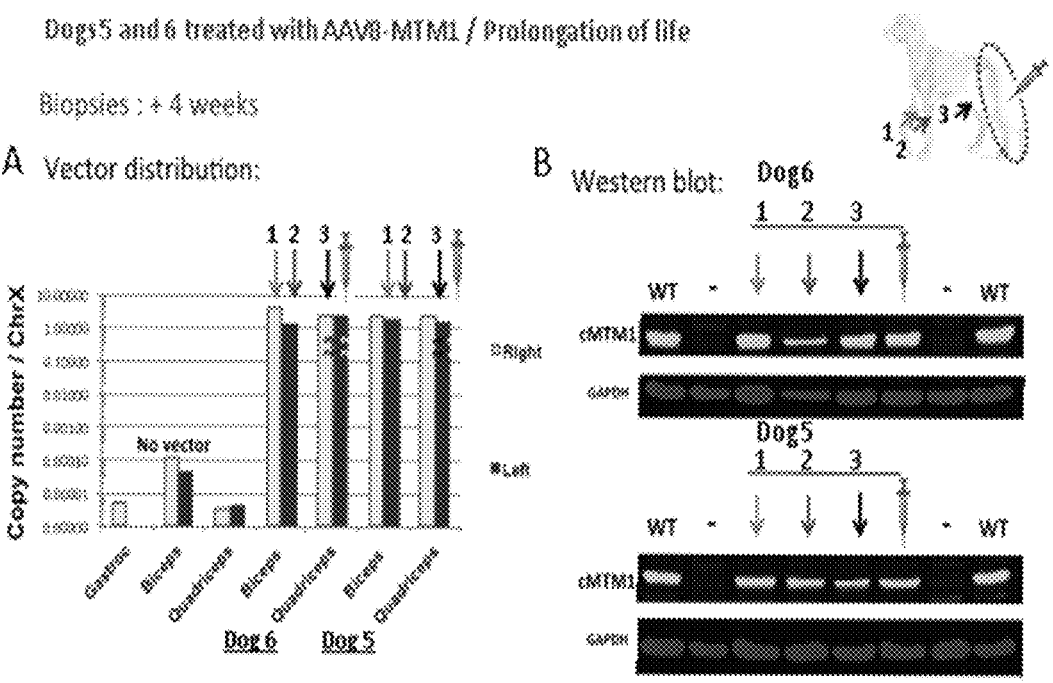
FIGS. 25A-25B depict the results of experiments demonstrating that Myotubularin is expressed following intravenous limb infusion of rAAV8-MTM1 in XLMTM dogs.

Contractile properties in canine muscles in vivo were assessed as described (Tegeler et al., 2010, Muscle Nerve. 42(1):130-2; Childers et al., 2011, J Vis Exp. 2011 Apr. 5; (50). pii: 2623). Briefly, the hind limbs of anesthetized dogs were immobilized in a frame to align the tibia at a right angle to the femur. Hind limb torque was measured by wrapping the foot to a pedal mounted on the shaft of a servomotor that also functioned as a force transducer. Percutaneous stimulation of the peroneal nerve activated hind limb muscles to pull the foot up toward the body to generate torque. Computer software controlled the servomotor, stimulation timing, and capture of torque responses. Isometric contractions were performed over a range of stimulation frequencies to determine torque-frequency relationships (FIG. 4B). This procedure was followed by a series of repeated contractions, first induced by an initial short isometric contraction followed by a forced stretch (eccentric contraction) lasting less than 1 sec. Contractions were repeated every 5 sec. for a total of 30 activations (FIGS. 25A-25B). Contractile data were analyzed as described (Tegeler et al., 2010, Muscle Nerve. 42(1):130-2) by investigators blinded to the experimental treatment.

Statistical Analysis

Statistical analyses were performed using SAS software (Version 6; SAS Institute Inc, Cary, N.C.). Individual means were compared using non-parametric tests (Mann-Whitney, or Wilcoxin rank-sum tests). Differences were considered to be statistically significant at either P<0.05 (1 symbol, *), or P<0.01 (2 symbols, ), or P<0.001 (3 symbols, *). All data are presented as means±Standard Error of the Mean (SEM).

The results of the experiments are now described

Figure 8A:
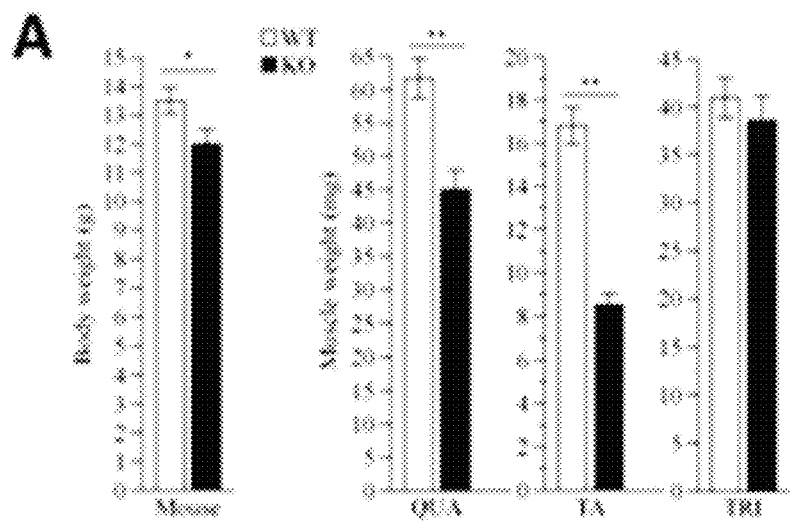
FIGS. 8A-8B depict the results of experiments demonstrating the pathology of muscles from 3 weeks-of-age myotubularin deficient (KO-Mtm1) mice.
Figure 8B:
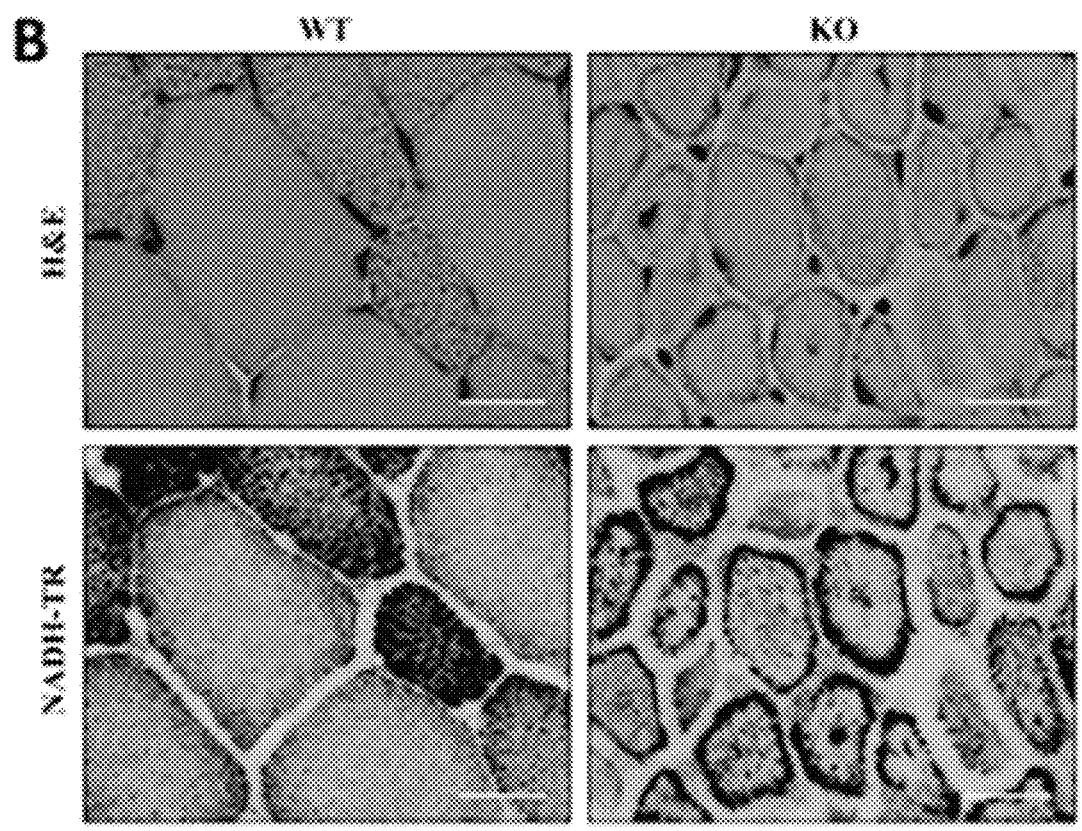

Systemic Mtm1 Delivery Improves Growth and Survival of Myotubularin-Knockout Mice Untreated myotubularin-knockout mice, whether constitutive (whole-body; KO-Mtm1)or muscle-specific (mKO-Mtm1), display muscle pathology by 3 weeks-of-age (FIGS. 8A-8B) and survive, on average, less than 2 months (Buj-Bello et al., 2002, Proc Natl Acad Sci USA 99(23):15060-5).

To correct the MTM1 deficiency, two muscle-tropic AAV vectors serotype 8 (AAV8) and serotype 9 (AAV9) were tested herein.

Figures 9A, 9B, 9C:
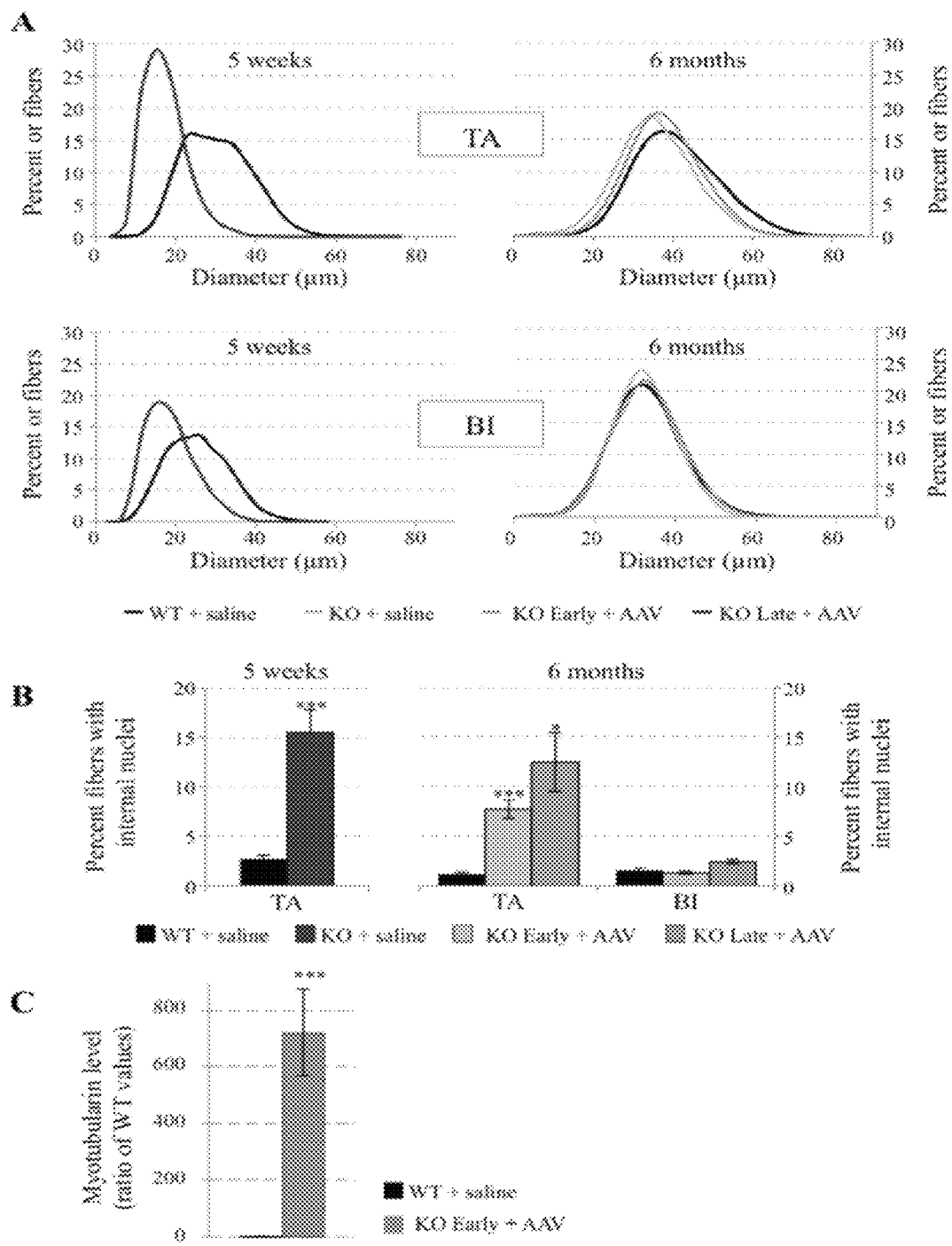
FIGS. 9A-9C depict the results of experiments demonstrating that systemic gene replacement therapy ameliorates pathological hallmarks of myotubular myopathy in skeletal muscles. Constitutive Mtm1 knockout mice (KO-Mtm1) at 3 weeks of age received a single intravenous injection of rAAV-Mtm1 as described elsewhere herein (see FIG. 1). Saline injected KO-Mtm1 and WT mice served as controls.

1) Use of Muscle-Tropic rAAV8 Vector in Mice:

For systemic delivery of Mtm1, the muscle-tropic serotype 8 AAV vector was developed expressing the Mtm1 complementary DNA (cDNA) under the control of a muscle-specific desmin promoter (AAV2/8-pDesmin-Mtm1, abbreviated AAV8 Mtm1 or more generally rAAV-Mtm1). The vector was produced in human embryonic kidney (HEK) 293 cells by a tritransfection-based system, formulated for in vivo injection, and used to treat two groups of KO mice at different stages of disease evolution, at the early onset of the pathology (3 weeks of age) or at the late stage of the disease when mortality occurs (5 weeks of age) (FIG. 1A). A single tail vein injection of AAV8-Mtm1 at a dose of $3\times10^{13}$ vg/kg in Mtm1 KO mice at 3 weeks (KO Early; n=8) conferred long-term survival and nearly normal growth on 100% of the treated animals (FIG. 1B and Movie 1 described below). The same dose was administered to severely affected mice at 5 weeks (KO Late; n=11), when 20% of the animals had already died. All treated mice remained viable and gained body mass over a 6-month observation period, except for a single 5-week-old mouse that died 1 day after injection (FIG. 1B and FIG. 1C). Consistent with their robust appearance, skeletal muscles grew to normal size in vector-injected Mtm1 KO mice. In both the early- and late-treated cohorts, each of the seven individual muscles analyzed gained mass, reaching >70% of the mass of wild-type muscle at 6 months (FIG. 1D). Analysis of myotubularin expression by Western blotting in individual muscles at sacrifice demonstrated that intravenous delivery of AAV8-Mtm1 reconstituted efficient myotubularin synthesis in skeletal muscles throughout the body. Myotubularin levels ranged between one and fivefold greater than wild-type values in most skeletal muscles. There was no major difference between the early and late treatment cohorts, except for two peaks of >15-fold expression in the soleus muscle of early-treated KO mice and >40-fold expression in the tibialis anterior of late-treated KO mice (FIG. 1E). Myotubularin was highly overexpressed in the heart (720±153 times the endogenous level 6 months after treatment) (FIG. 9C). The AAV8-Mtm1 average vector copy number (VCN; corresponding to viral genomes per diploid genome) in early and late-treatedmice was 0.72±0.1 and 0.87±0.1 in the tibialis anterior muscle and 1.67±0.4 and 3.33±2.1 in the biceps brachii muscle, respectively. VCN in the heart and liver ranged between 1.17 to 5.14 and 80 to 223 viral genomes/diploid genome, respectively, consistent with the known tropism of AAV8. At necropsy, the heart of AAV-treated KO mice showed the presence of some focal lesions with scar tissue and a modest cellular infiltrate, although these lesions did not affect survival in any of the treated Mtm1 KO animals.

Movie 1, available at www dot sciencetranslationalmedicine dot org/cgi/content/full/6/220/220ra10/DC1 in a mp4 format, shows in the same cage a wild-type mouse (red tail and tag) injected with PBS and a myotubularin-deficient mouse (blue tail and tag) treated with AAV8-Mtm1 (3×10$^{13}$ vg/ml) at 6 months after injection. One can clearly note the robust appearance, normal size, and activity of the treated Mtm1 KO mouse which is very similar to the wild-type mouse.

Figures 19A, 19B, 19C, 19D, 19E, 19F, 19G, 19H:
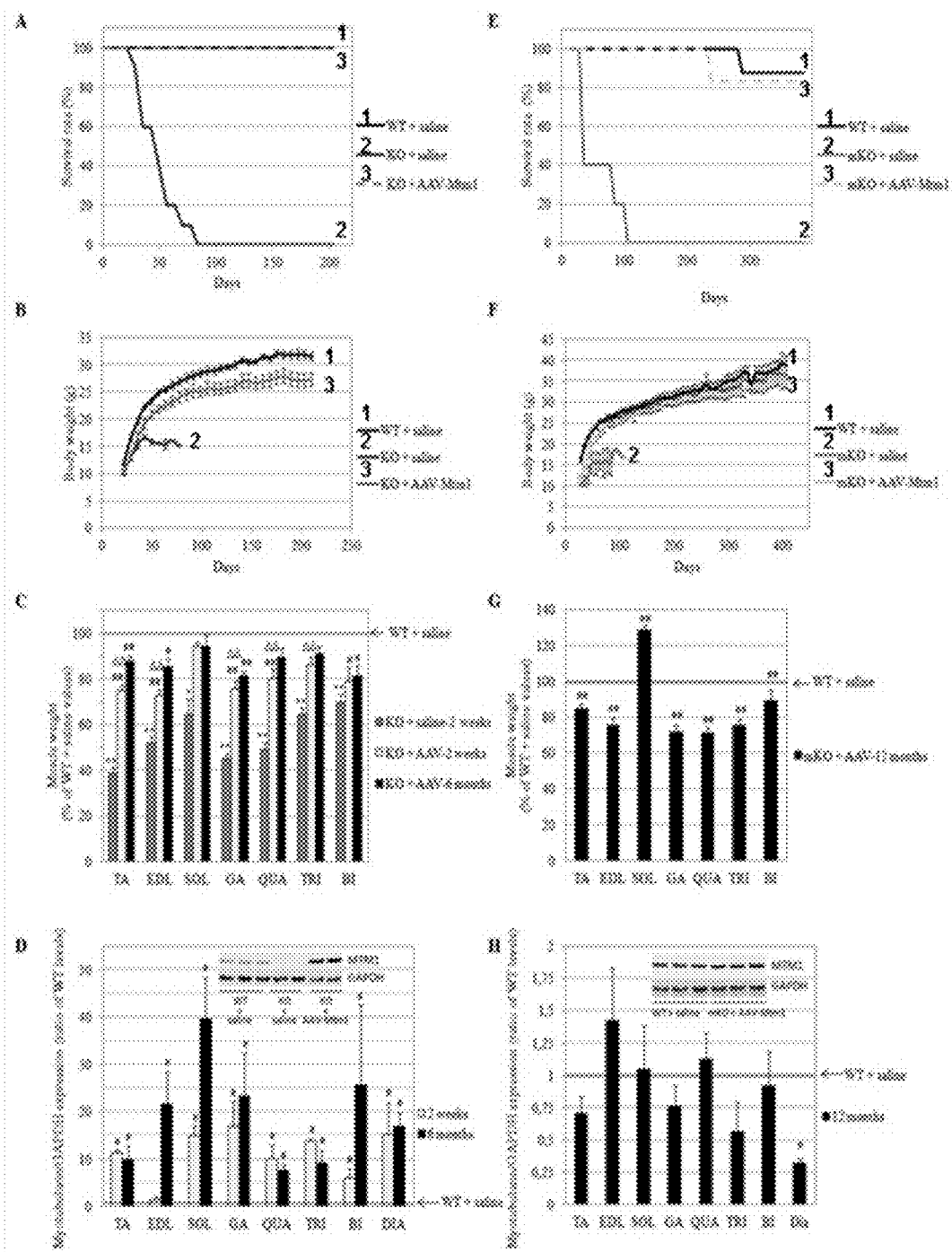
FIGS. 19A-19H depict the results of experiments demonstrating that intravascular delivery of rAAV-Mtm1 in myotubularin-deficient mice improves lifespan and body growth.

2) Use of Muscle-Tropic rAAV9 Vector in Mice:

For systemic delivery of Mtm1, a muscle-tropic rAAV9 vector was used and the desmin promoter was employed to restrict expression to muscle (rAAV2/9-pDesmin-Mtm1$^{murine}$, abbreviated AAV9-Mtm1 or more generally rAAV-Mtm1). It was observed that in both strains a single intravenous injection of vector conferred long-term survival and nearly normal growth (FIGS. 19A-19H). When 5 symptomatic KO-Mtm1 mice received rAAV-Mtm1 (3.0×10$^{13}$ vg/kg), all remained viable and gained body mass over a 6-month observation period (FIG. 19A and FIG. 19B). The study was replicated in 6 mKO-Mtm1 mice using a lower vector dose (0.5×10$^{13}$ vg/kg). In this case, 5 treated animals survived and grew normally during a 12-month follow-up, and the sixth died well beyond the usual survival limit (FIG. 19E and FIG. 19F). Consistent with their robust appearance and activity, the vector-injected Mtm1-defective mice achieved gross normalization of their skeletal muscles. In the treated KO-Mtm1 cohort, every individual muscle assessed gained mass by the second week post-injection, and muscle masses reached >80% of WT at 6 months (FIG. 19C). Similarly, the muscle masses of vector-treated mKO-Mtm1 mice exceeded 75% of WT at 12 months (FIG. 19G).

Immunoblotting demonstrated that intravenous delivery of rAAV-Mtm1 enabled efficient, sustained production of myotubularin in skeletal muscles throughout the body. In the KO-Mtm1 mice at 2 weeks post-injection, the relative level of myotubularin in most individual muscles exceeded WT muscles by at least 5-fold (FIG. 19D). At 6 months, myotubularin expression ranged between 7- to 40-fold greater than WT. The muscles of treated mKO-Mtm1 mice, which received one-sixth the vector dose, were also uniformly positive for myotubularin protein. At 12 months post-injection, the levels were near normal—approximately 30% of WT in the diaphragm, and 60% to 140% in various other muscles (FIG. 19H).

Mtm1 Gene Therapy Corrects the Pathology of Myotubularin-Deficient Mouse Muscles The muscles of myotubularin-knockout mice that received a muscle-tropic AAV vector expressing Mtm1 gene underwent rapid and sustained amelioration of pathological features.

Figures 2A, 2B:
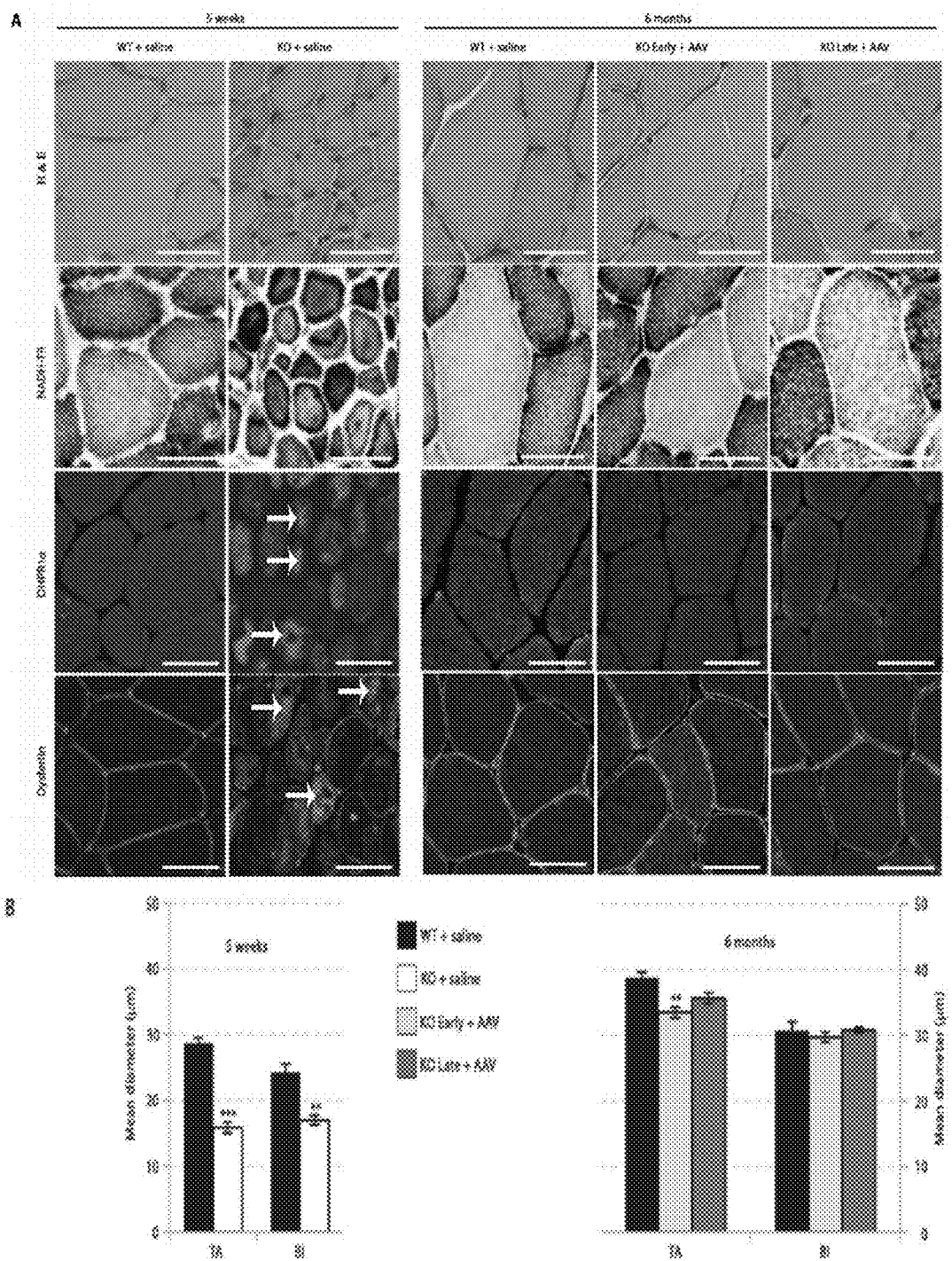
FIGS. 2A-2B depict the results of experiments demonstrating that Mtm1 gene replacement therapy corrects the internal architecture and hypotrophy of skeletal muscle fibers in myotubularin-knockout mice. Treatment groups were as described in FIG. 1B. Mice were injected with either saline (+saline) or rAAV-Mtm1 vector (+AAV). Sections were obtained after 2 weeks (5 weeks of age) and 6 months of treatment.

FIGS. 2A-2B show representative histology from the tibialis anterior and biceps brachii limb muscles of untreated, 5-week-old Mtm1 KO mice and AAV-treated, 6-month-old KO mice, demonstrating normalized cross-sectional fiber size and intracellular architecture, as revealed by hematoxylin and eosin (H&E) and NADH (reduced form of nicotinamide adenine dinucleotide) tetrazolium reductase (NADH-TR) staining (see FIGS. 9A-9C for additional information). Morphometry of tibialis anterior and biceps brachii myofibers from 5-week-old Mtm1 KO mice gave a mean diameter of 15.9±0.8 mm and 17±0.7 mm, respectively, with many fibers below 20 mm, compared to 28.7±0.8 mm and 24.3±1.2 mm for wild-type mice (FIG. 2B and FIG. 9A). Six months after treatment with AAV8-Mtm1, the abundance of extremely small-diameter myofibers was eliminated, and the size distribution approached that of wild-type muscles in both cohorts. In addition, myofibers of treated mice displayed a reduced frequency of centrally localized nuclei, a diagnostic feature of centronuclear myopathies like XLMTM (FIG. 9B). Distinctive features of myotubularin-deficient myofibers include aberrant accumulations of mitochondria and a marked deficiency of transverse tubules (T-tubules), invaginations of the plasma membrane perpendicular to the length of the myofiber that are critical for excitation contraction coupling and muscle function. Untreated Mtm1 KO mice showed abnormal localization of proteins associated with the T-tubule system, including the dihydropyridine 1a receptor (DHPR1a), a voltage-gated Ca$^{2+}$ channel, and dysferlin, a transmembrane protein involved in Ca$^{2+}$-dependent membrane repair (FIG. 2A, arrows). Treatment with AAV8-Mtm1 corrected abnormal mitochondria distribution and cellular mislocalization of DHPR1a and dysferlin in all mice from both early- and late-treated cohorts, indicating that XLMTM-associated pathology can be reversed well after the onset of the disease.

Figures 20A, 20B, 20C, 20D, 20E, 20F:
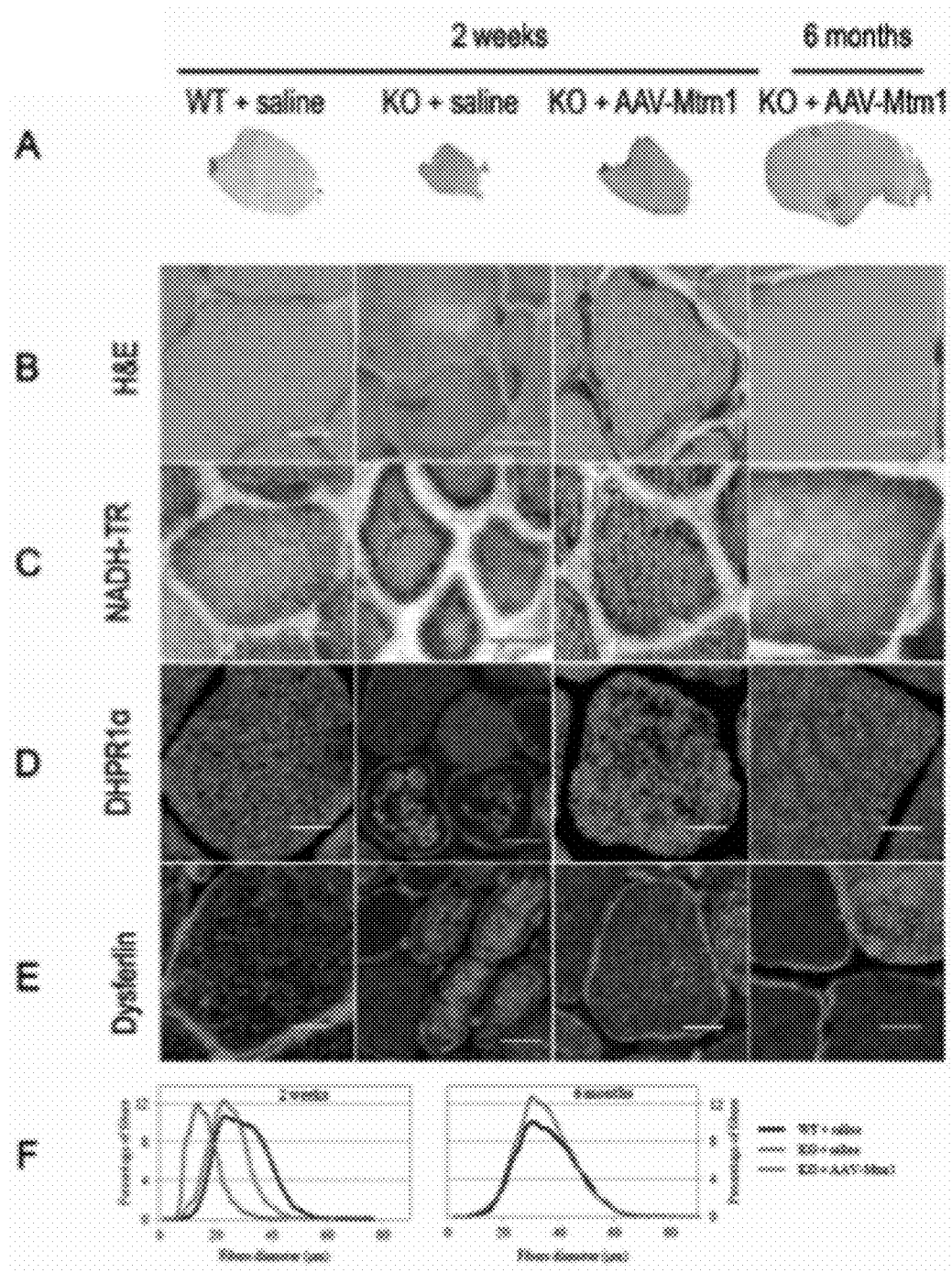
FIGS. 20A-20F depict the results of experiments demonstrating that Mtm1 gene replacement therapy corrects the internal architecture and hypotrophy of skeletal muscle fibers in myotubularin-knockout mice. Treatment groups were as described in FIGS. 1A-1B. WT=C57BL/6 mice; KO=constitutive KO-Mtm1 mice. Mice were injected with either saline (+saline) or rAAV vector (+Mtm1). Sections were obtained at 2 weeks and 6 months.
Figures 23A, 23B, 23C:
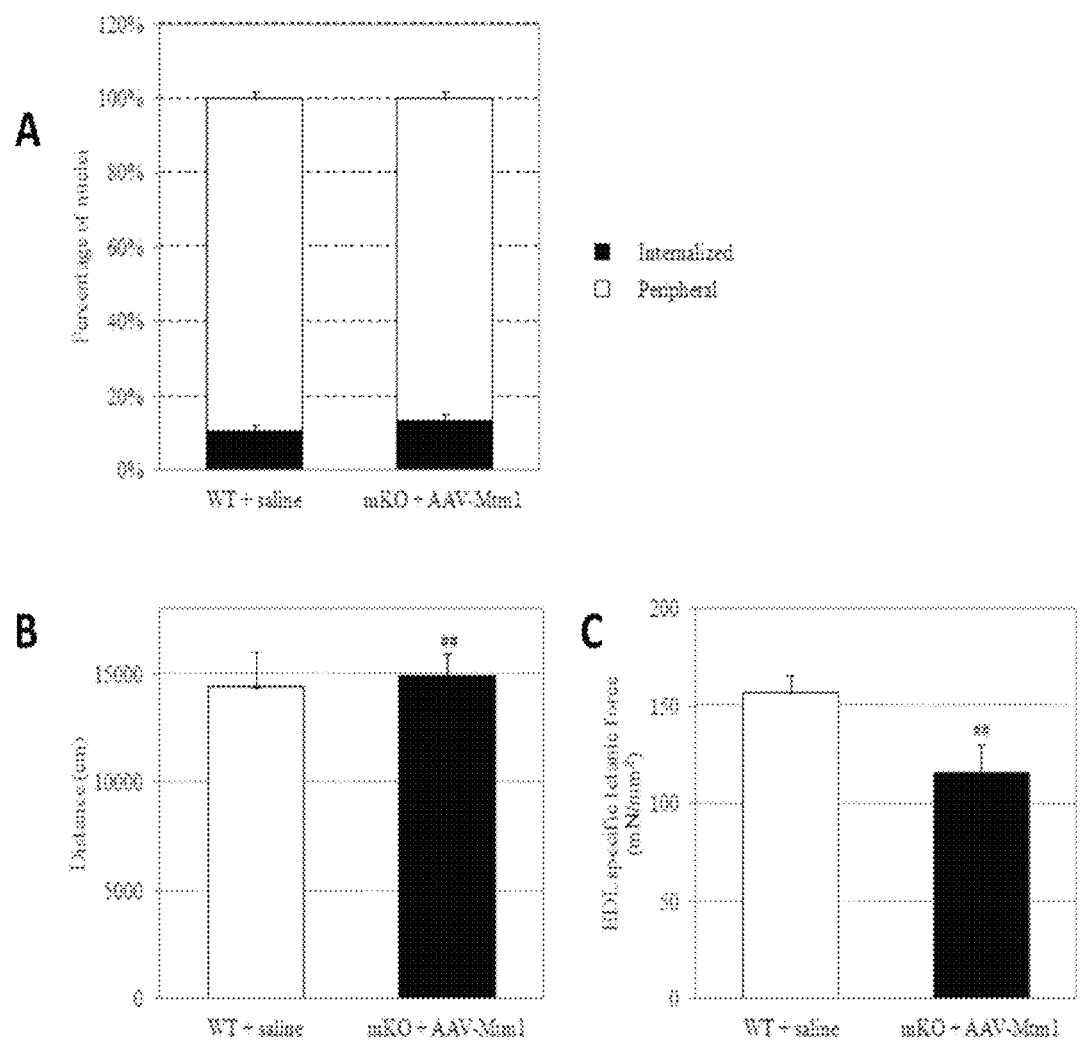
FIGS. 23A-23C depict the results of experiments demonstrating the correction of structural and functional muscle defects by Mtm1 gene replacement therapy in muscle-specific myotubularin deficient mice. A single intravenous injection of rAAV-Mtm1 ($0.5 \times 10^{13}$ vg/kg) was administered to mKO-Mtm1 mice at 4 weeks-of-age, as described in Methods. Age-matched, saline-injected mKO-Mtm1 and wild-type C57BL/6 (WT) mice served as controls.

FIG. 20A-20F show representative data from the tibialis anterior (TA) muscle of KO-Mtm1 animals at 2 weeks and at 6 months after the single systemic vector treatment. (See FIGS. 22A-22B for additional muscles). The cross-sectional area of limb muscles enlarged (FIG. 20A) and muscle fibers increased in size (FIG. 20B, FIG. 20F FIG. 22A and FIG. 22B). Morphometry of untreated mutant TA myofibers at 5 weeks-of-age gave a mean diameter of 15.9±1.7 μm, with many below 20 μm, compared to 28.7±2.1 μm for WT (FIG. 20F). By 2 weeks post-treatment with rAAV-Mtm1, the skew towards extremely small diameter myofibers was eliminated, and at 6 months the size distribution approached that of WT. In addition, myofibers of treated KO-Mtm1 and mKO-Mtm1 mice displayed a reduced frequency of internalized nuclei, a diagnostic feature of centronuclear myopathies such as XLMTM (FIG. 23A).

Figure 24:
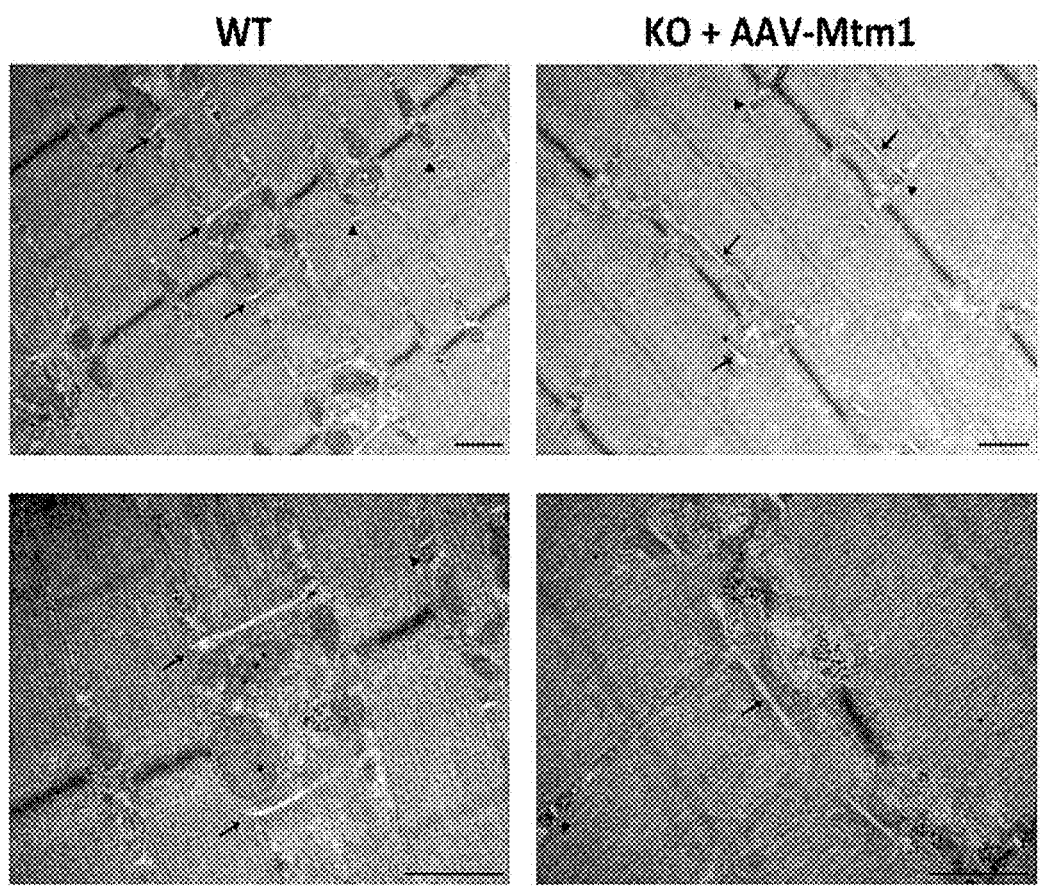
FIG. 24 depicts the results of experiments demonstrating that Myotubularin gene therapy restores normal muscle ultrastructure in myotubularin-deficient mice. Electron micrographs of TA muscles at 6 months after injection of WT mice with saline and of KO-Mtm1 mice with rAAV-Mtm1. Both groups show similar numbers and structure of T-tubules (arrows) and triads (arrowheads). Scale bars: 1 µm (upper panels); 500 nm (lower panels).

Mtm1 gene delivery also corrected the intracellular muscle architecture of the mutant mice, as revealed by hematoxylin-eosin and NADH-tetrazolium reductase (NADH-TR) staining (FIG. 20B and FIG. 20C). Distinctive features of myotubularin-deficient myofibers include aberrant accumulations of glycogen and mitochondria, and a marked deficiency of transverse tubules (T-tubules)—invaginations of the plasma membrane perpendicular to the length of the myofiber critical for excitation-contraction coupling and, thereby, muscular function. Immunofluorescent staining of muscle from KO-Mtm1 mice showed abnormal localization of proteins associated with the T-tubule system, including dihydropyridine 1α receptors (DHPR1α; voltage-gated calcium channels) and dysferlin, a transmembrane protein involved in calcium-dependent membrane repair (FIG. 20D and FIG. 20E). Consistent with the previous observations after intramuscular vector delivery (Buj-Bello et al., 2008, Hum Mol Genet 17(14):2132-43), systemic myotubularin gene therapy rapidly restored normal myofiber morphology, in particular the cellular localization of DHPR1α and dysferlin. This restoration was maintained through the 6-month assessment. Myofiber ultrastructure in rAAV-Mtm1-treated mutants appeared normal by electron microscopy, with properly distributed T-tubules and triads (FIG. 24).

Structural abnormalities of muscle in Mtm1-defective mice are mirrored by functional deficits. Whole-body and muscle-specific knockouts display equivalent phenotypes, implying that myotubularin deficiency in skeletal muscle is necessary and sufficient to account for the dysfunction.

Structural muscle abnormalities are mirrored by severe functional deficits in Mtm1 KO mice. To measure the effect of gene therapy on muscle function, the open-field actimeter, global muscle strength, and isolated limb strength assays were used. Open-field actimeter measurements showed that mutant mice covered less than half the distance explored by wild-type mice at 5 weeks of age (FIG. 3A). Mice treated with AAV8-F3 Mtm1 at both early and late stages of the disease showed significant functional improvement, and at 6 months after AAV injection, their motor activity was indistinguishable from that of wild-type animals. A noninvasive test of global muscle strength that measures forward pulling tension in an escape paradigm revealed that untreated Mtm1-deficient mice were half as strong as wild-type mice (whole-body tension, 0.07±0.01 versus 0.15±0.01 N/g; P<0.01) (FIG. 3B). Early- and late-treated mice showed 82% (0.15±0.01N/g) and 76%(0.13±0.01N/g) recovery of whole-body tension, respectively (FIG. 3B). In a functional assay of an isolated hindlimb muscle, the extensor digitorum longus, the isometric force of untreated Mtm1 KO mice was only 13% of the wild-type level, whereas it almost normalized 6 months after AAV8-Mtm1 delivery in both cohorts (P=0.0016 and P<0.001 for the early and late-treated groups of mice, respectively; FIG. 3C). Together, these data indicate that muscle impairment associated with myotubularin deficiency can be rescued by gene therapy even after the onset of pathology.

Multiple tests demonstrated long-term restoration of muscle function by systemic myotubularin gene therapy in KO-Mtm1 (FIG. 3) and mKO-Mtm1 mice (FIG. 23B and FIG. 23C). Open-field actimeter measurements demonstrated mutants at 5 weeks-of-age displayed fewer than half the episodes of spontaneous motor activity, and covered less than half the distance explored by WT mice (FIG. 20A). However, KO-Mtm1 mice that received systemic rAAV-Mtm1 2 weeks prior to the test showed significant improvements. At 6 months post-therapy (or 12 months in the mKO-Mtm1 study, FIG. 23B) their behavior was indistinguishable from WT. Another noninvasive test of motor activity and global strength, initially validated in a mouse muscular dystrophy model, measured forward pulling tension in an escape paradigm (FIG. 20B). By this assay, 5 week-old KO-Mtm1 mice were approximately half as strong as WT (whole body tension 0.07±0.01 versus 0.15±0.01 mN/g). The improvement in mutants given gene therapy 2 weeks earlier was pronounced; their whole body tension was 87% of normal (0.13±0.01 mN/g). After 6 months, the treated mutants still performed similarly to WT.

Finally, the function of an isolated hind limb muscle, the extensor digitorum longus (EDL) was assessed in an isometric force assay (FIG. 3C and FIG. 23C). EDL muscle strength of untreated KO-Mtm1 mice was only 13% of WT. Two weeks after rAAV-Mtm1 delivery, the strength of mutant muscles increased nearly 4-fold over saline-injected controls. By 6 months, the strength of EDL muscles from vector-treated mutants equaled that of WT.

Correction of Muscle Pathology in Myotubularin-Deficient Mice is Dose-Dependent

Figures 10A, 10B, 10C, 10D, 10E:
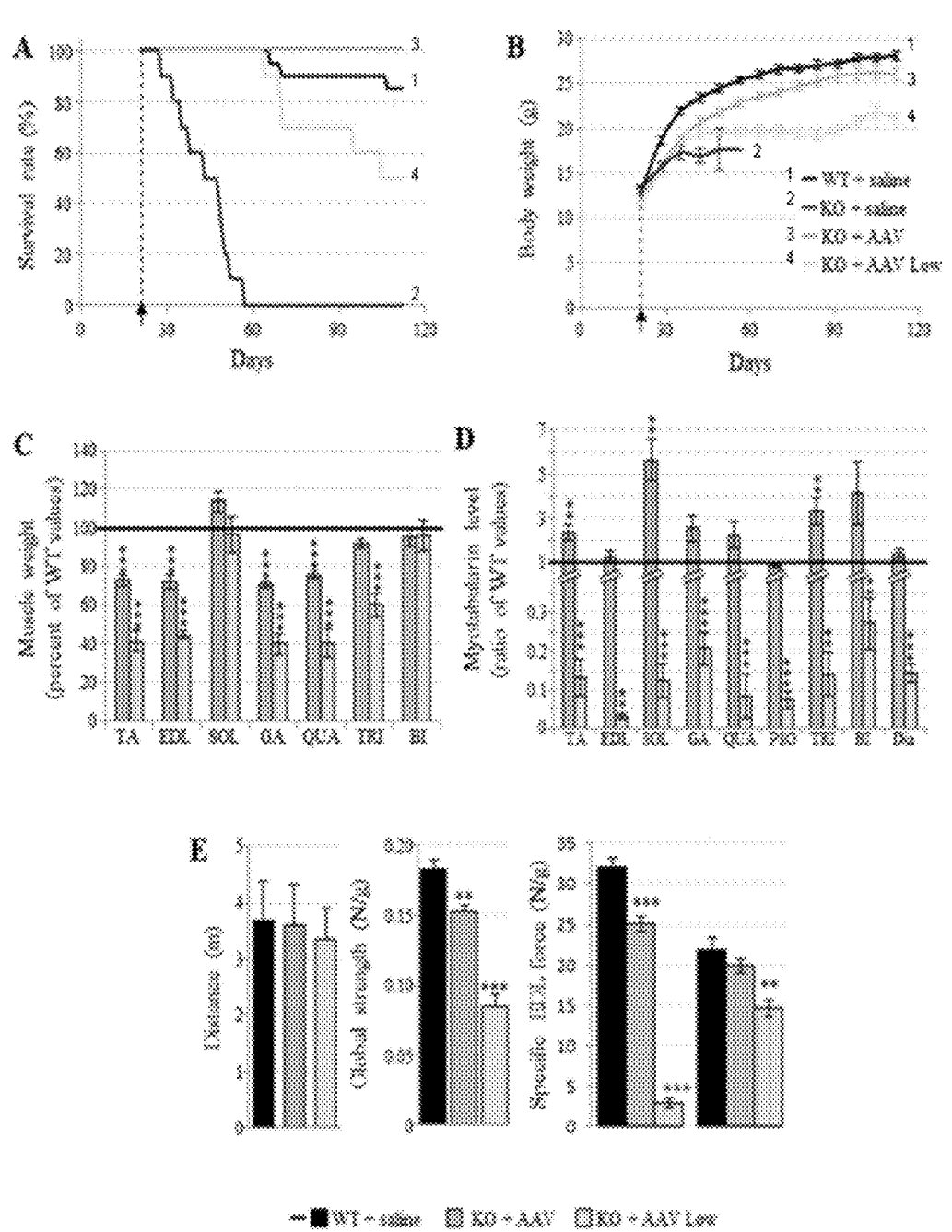
FIGS. 10A-10E depict the results of experiments demonstrating that intravascular delivery of a lower dose of AAV8-Mtm1 in myotubularin-deficient mice improves partially life span and body growth.

To assess the effect of a lower vector dose on phenotype correction, AAV8-Mtm1 ($5 \times 10^{12}$ vg/kg) was injected into the tail vein of Mtm1 KO mice at 3 weeks of age (n=10). This dose prolonged the survival of 50% of the mice over 3 months, with the first death occurring 6 weeks after injection (FIG. 10A). Body weight increased during the first 3 weeks of treatment and remained unchanged after this period (FIG. 10B). This partial recovery of body mass was reflected at the level of individual skeletal muscles: two of the seven analyzed muscles (soleus and biceps brachii) grew normally, whereas the other five reached 40 to 60% of wild-type mass at 3 months (FIG. 10C). Themotor activity of mice treated with the low vector dose appeared indistinguishable from that of wild type (WT) mice and KO mice treated with the high dose in an open-field actimeter assay 3 months after injection (FIG. 10E). However, their global muscle strength was reduced by 55% in the more sensitive escape test, and their isolated soleus and extensor digitorum longus muscles generated 60 and 9% of the wild-type force, respectively, indicating that muscle function recovery was not complete in the low-dose cohort. In the extensor digitorum longus muscle, only 3% of the myotubularin endogenous level was reached (FIG. 10D), ranging from 7 to 27% in the other analyzed muscles (mean=13%), indicating that low levels of MTM1 are sufficient to prolong the survival of mutant mice.

rAAV8-MTM1 Administration Rescues Pathology of XLMTM Canine Muscles

To evaluate myotubularin gene replacement therapy in a large animal XLMTM model, affected male Labrador/beagle F1 offspring, which display the same pathology and clinical features as previously reported for affected purebred Labradors, were studied The mutant dogs become symptomatic by 9 to 10 weeks-of-age. Muscular weakness progresses for approximately 6-8 more weeks to ~18 weeks-of-age, when animals can no longer ambulate and experiments are terminated.

Effects of Intramuscular Delivery of rAAV8-MTM1.

Figures 21A, 21B, 21C, 21D:
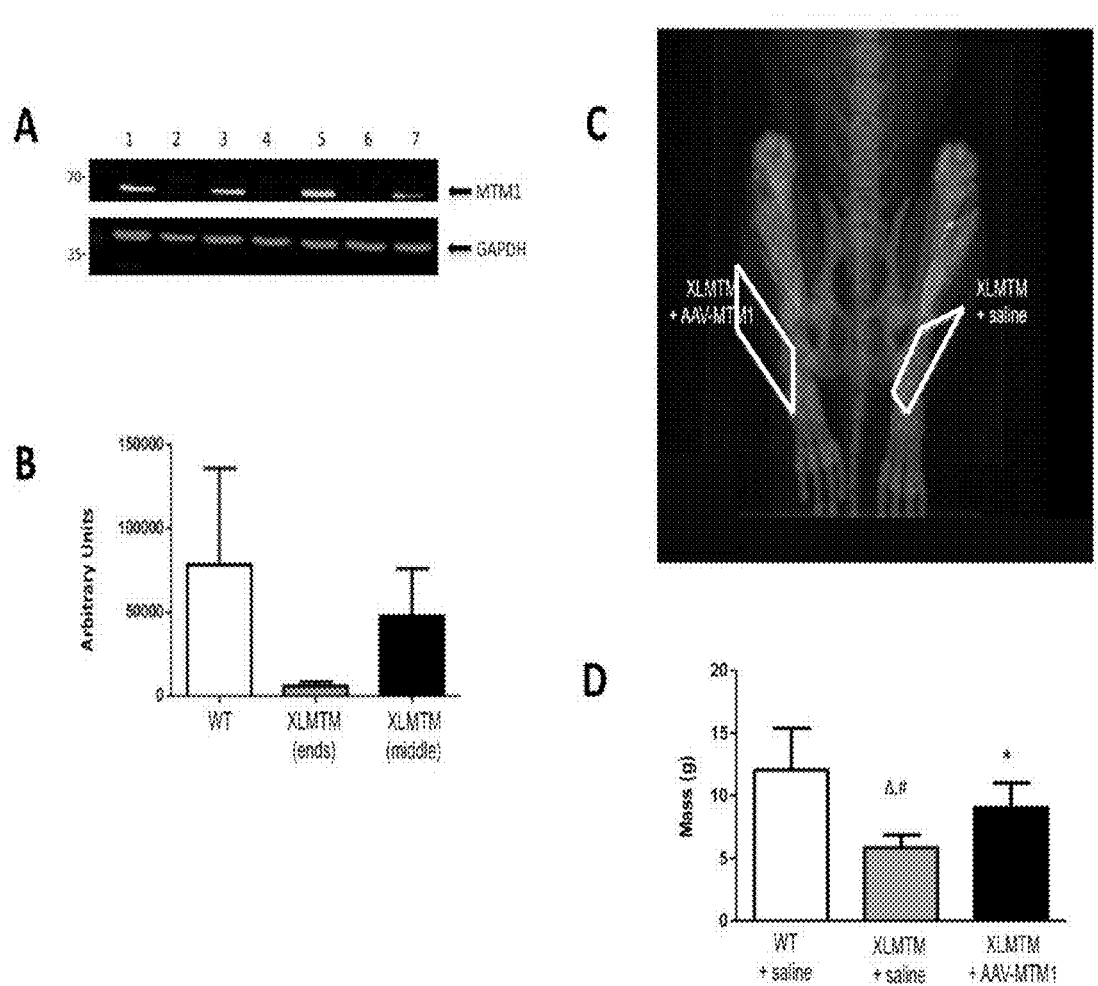
FIGS. 21A-21D depict the results of experiments demonstrating that Myotubularin is expressed and increases muscle mass and volume after local gene therapy in XLMTM dogs.
Figures 22A, 22B:
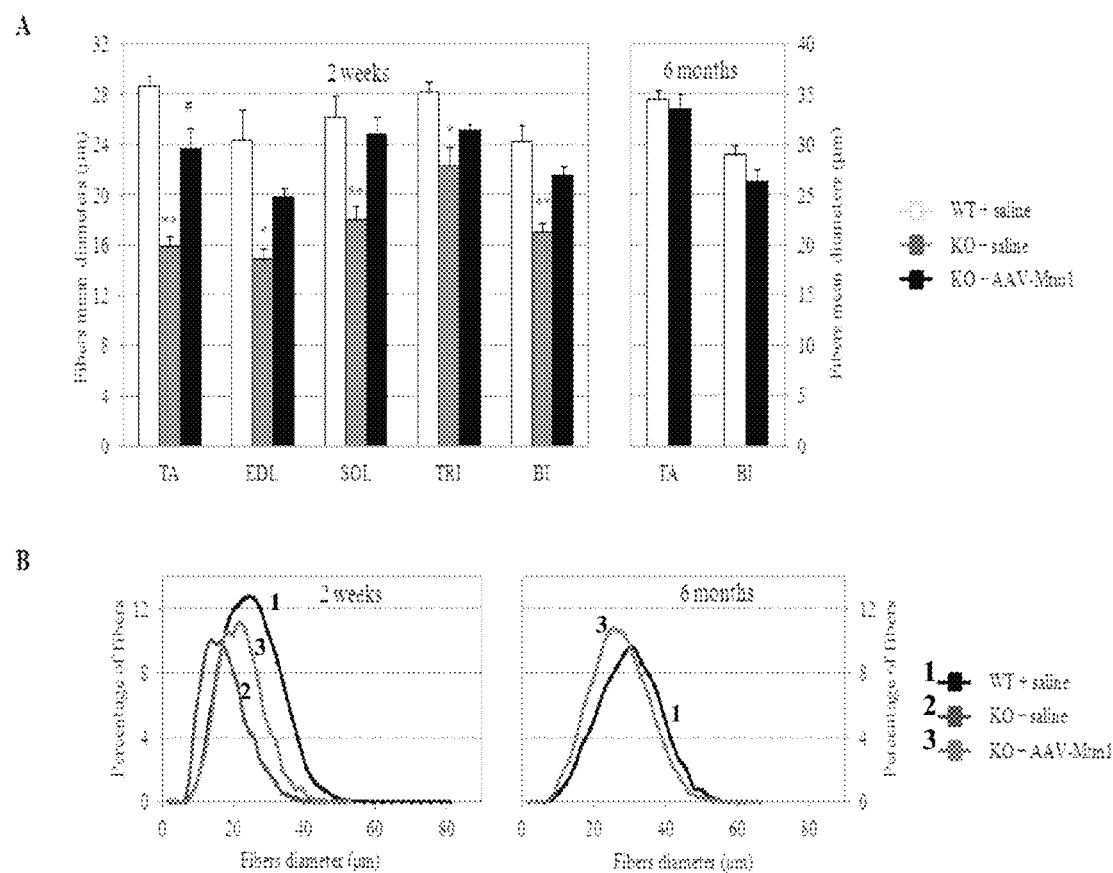
FIGS. 22A-22B depict the results of experiments demonstrating that systemic gene replacement therapy ameliorates hypotrophy of skeletal muscles throughout the body of myotubularin-deficient mice. Constitutive Mtm1 knockout mice (KO-Mtm1) at 3 weeks-of-age received a single intravenous injection of rAAV-Mtm1. Saline injected KO-Mtm1 and WT mice served as controls.

The first goal was to confirm transgene expression in skeletal muscle, using the muscle-tropic serotype 8 AAV vector to deliver canine MTM1 cDNA driven by the desmin promoter. A single intramuscular injection ($4 \times 10^{11}$ vg/kg) of rAAV8-pDesmin-MTM1$^{canine}$ (rAAV-MTM1) was administered into a hind limb, at the middle of the cranial tibialis muscle, of each of three XLMTM dogs at 10 weeks-of-age. The contralateral limb received only saline. Saline-injected unaffected male littermates served as WT controls. Immunoblotting confirmed substantial amounts of myotubularin protein in rAAV-MTM1-injected muscles of all 3 XLMTM dogs (FIG. 21A). After 4 to 6 weeks, the level relative to WT was approximately 60% near the center of the cranial tibialis and about 8% at its ends (FIG. 21B). Some transgene-encoded protein was also observed in the contiguous EDL muscle. However, neither the contralateral limb muscles, nor distant skeletal muscles such as diaphragm, nor heart muscles contained detectable myotubularin.

Figure 4A:
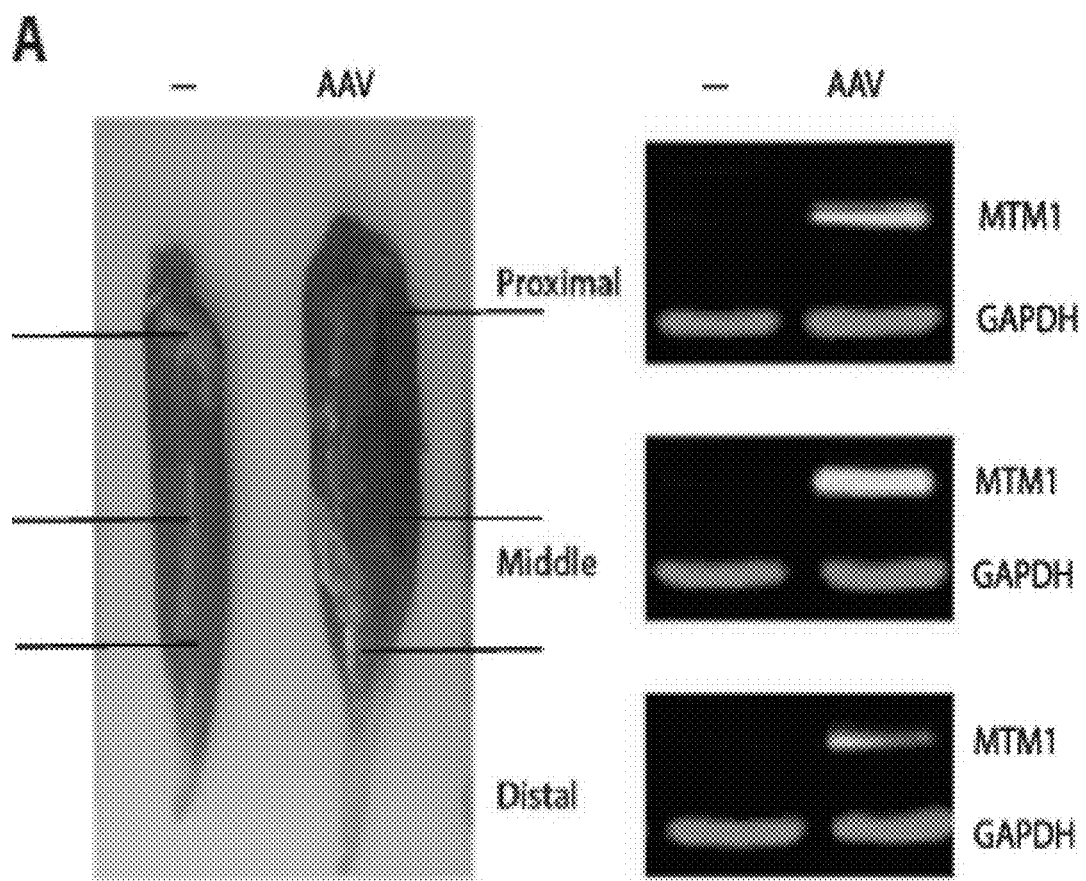
FIGS. 4A-4C depict the results of experiments demonstrating that myotubularin is expressed and increases muscle mass and volume after local gene therapy in XLMTM dogs.
Figure 4B:
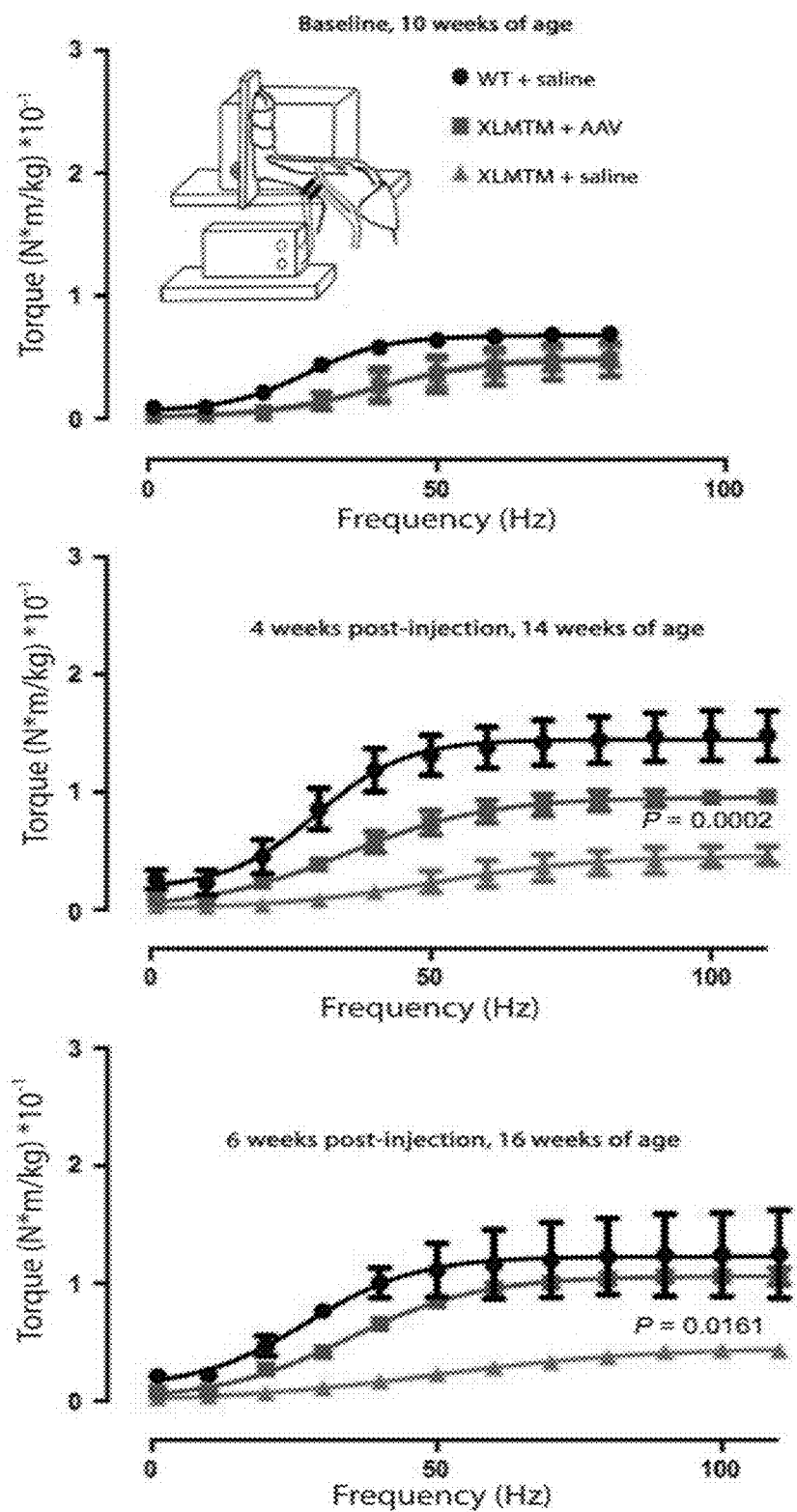
Figure 11A:
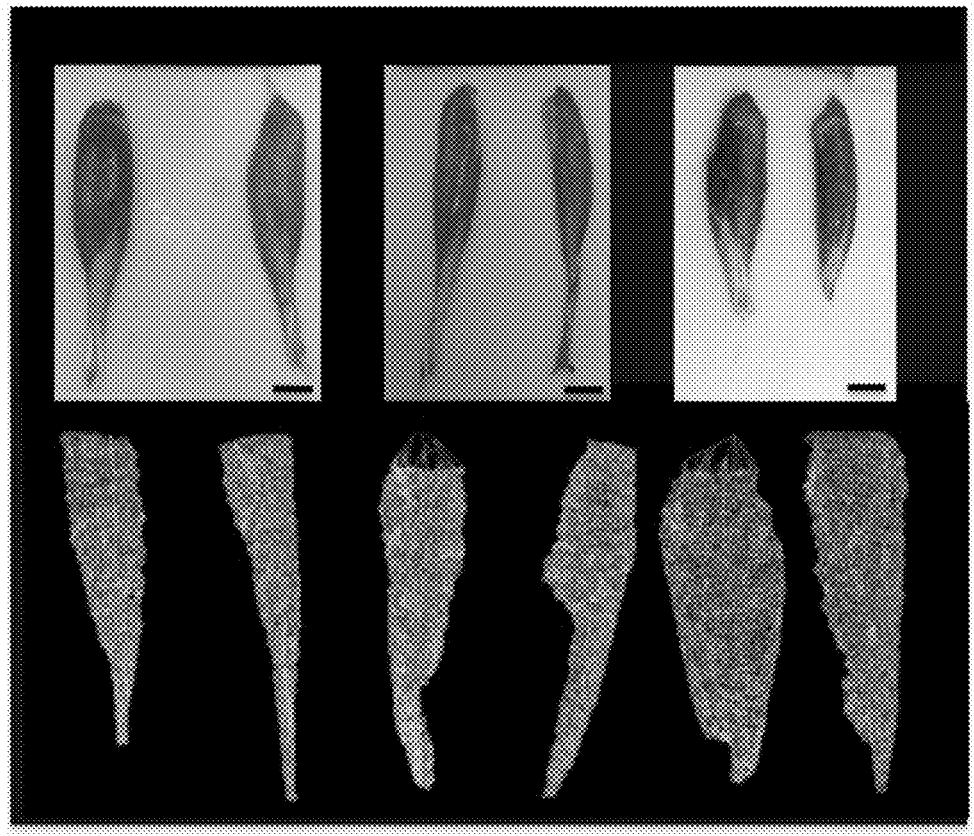
FIGS. 11A-11B depict the results of experiments demonstrating that targeted myotubularin gene replacement therapy in XLMTM dogs increases the overall size of injected muscles.
Figure 11B:
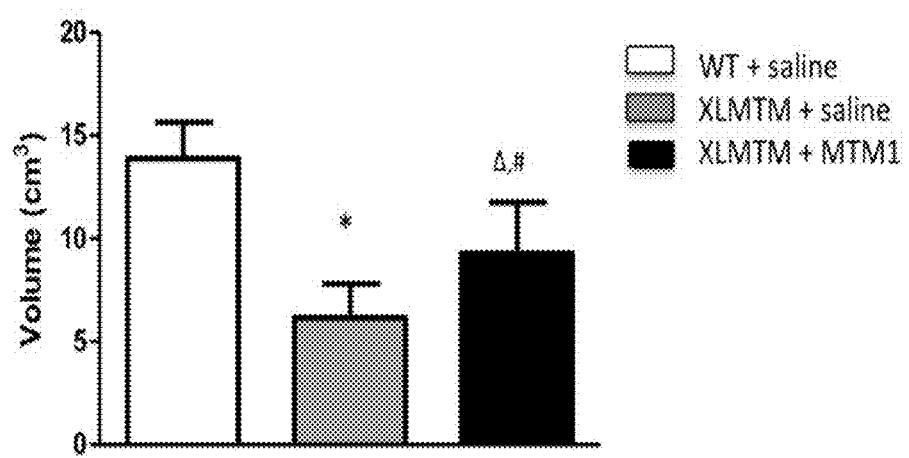

In every case, the mutant muscle injected with rAAV8-MTM1 grew significantly larger than the contralateral control muscle (FIG. 4A and FIGS. 11A-11B). Weight measurements and computed tomography (CT) scans showed that myotubularin gene therapy increased muscle mass (FIG. 21C and FIG. 21D) and volume by about 50% in 4 to 6 weeks (P=0.079) (FIGS. 11A-11B), respectively.

Figure 4C:
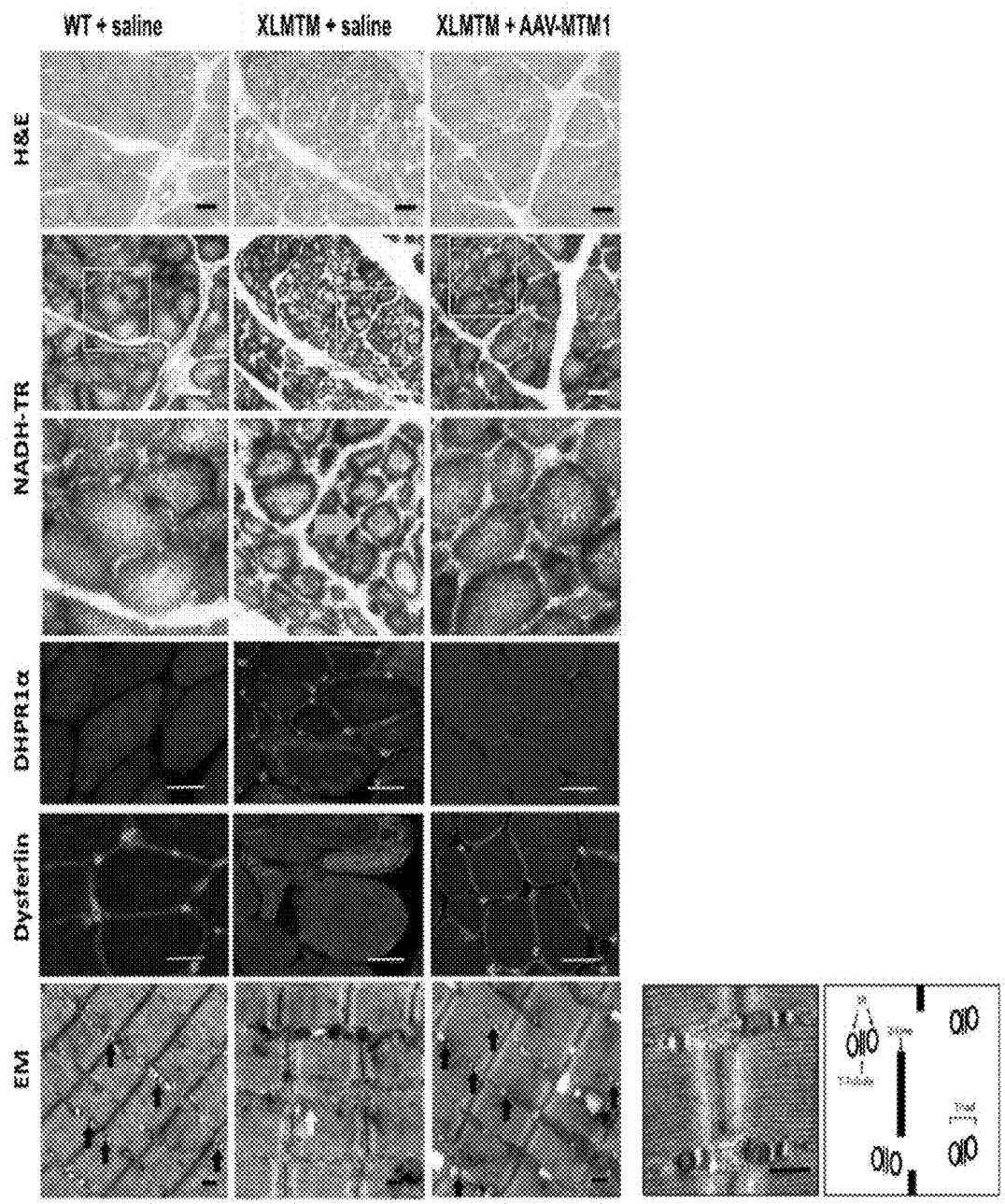

Skeletal muscles from myotubularin-deficient dogs, similar to those from myotubularin-knockout mice, display histological aberrations typical of XLMTM. Muscles of rAAV-MTM1-injected mutant canine limbs consistently showed improved architecture, increased myofiber size, and less mislocalization of organelles (including mitochondrial aggregates and "necklace" fibers) (FIG. 4C; Table 1). Myotubularin gene therapy also corrected the localization of DHPR1α and dysferlin as observed by immunofluorescent staining (FIGS. 4A-4C). Electron microscopy confirmed that, by comparison with WT muscle, XLMTM muscle contained few characteristic T-tubules but showed atypical longitudinal structures (L-tubules). By contrast, rAAV-MTM1-injected mutant muscles closely resembled WT, with abundant T-tubules (FIG. 4C; Table 1 listed below).

TABLE 1

Quantified Histological Findings in Dogs Following Intramuscular Injection

| | WT + saline | XLMTM + saline | XLMTM + AAV | p Value |
|---|---|---|---|---|
| Histological Findings | | | | |
| Mean MinFeret Fiber Diameter (μm) | 32.0 ± 8.0 | 17.3 ± 4.1 | 30.2 ± 3.7 | 0.06 |
| % Fibers with Central Nuclei | 0 | 7.5 ± 5.1 | 5.4 ± 4.0 | 0.42 |
| % Fibers with Central Organelle Aggregates | 0 | 17.1 ± 4.0 | 4.3 ± 6.6 | 0.14 |
| % Necklace Fibers | 0 | 31.9 ± 16.8 | 4 ± 6.7 | 0.17 |
| Ultrastructural Findings | | | | |
| T Tubules/Fiber | 10.6 ± 1.5 | 3.9 ± 2.0 | 10.2 ± 3.0 | 0.04 |
| L Tubules/Fiber | 0.18 ± 0.01 | 1.56 ± 0.20 | 0.18 ± 0.25 | 0.15 |

Effects of Intravascular Delivery of rAAV8-MTM1.

Figure 6A:
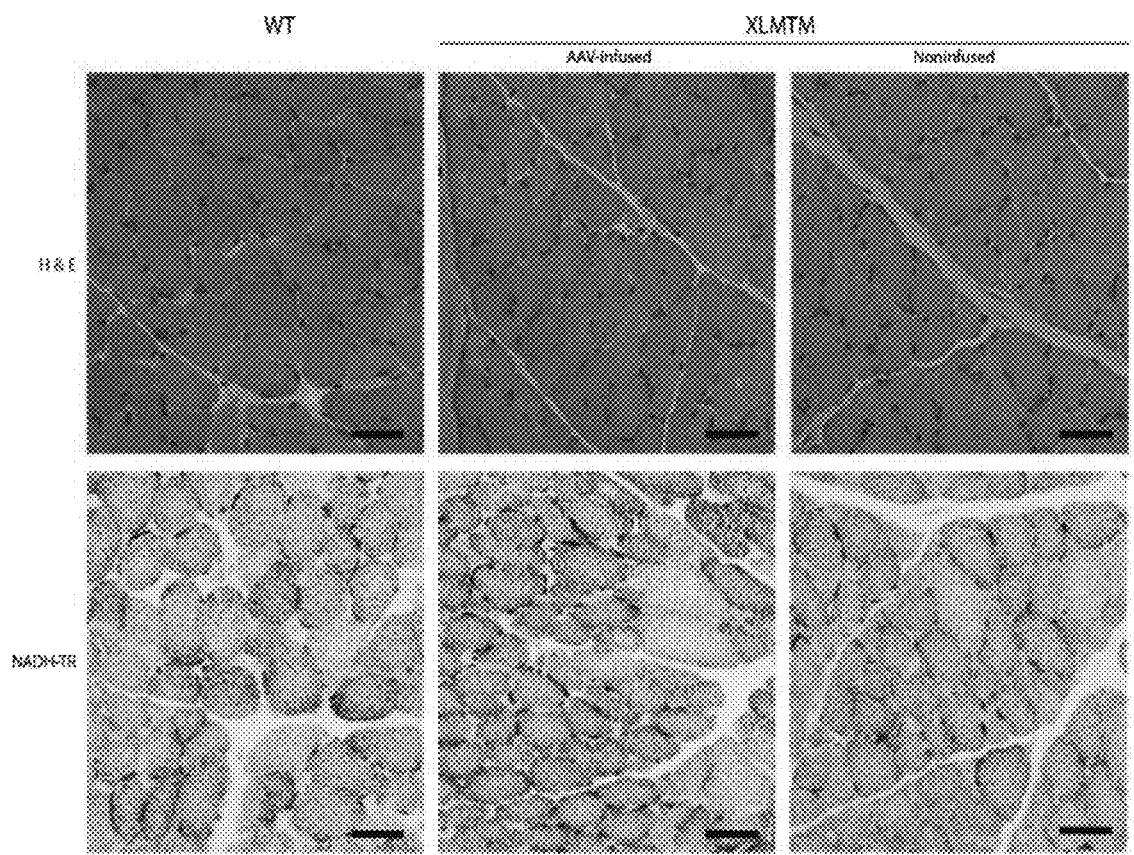
FIGS. 6A-6B depict the results of experiments demonstrating that MTM1 gene therapy corrects the internal architecture and hypotrophy of skeletal muscle fibers in myotubularin-mutant dogs. Muscle cryosections from age-matched WT or AAV8-MTM1-infused XLMTM dogs were assessed microscopically. Comparison is shown between the left (infused) hindlimb and the right (contralateral noninfused) limb.
Figure 6B:
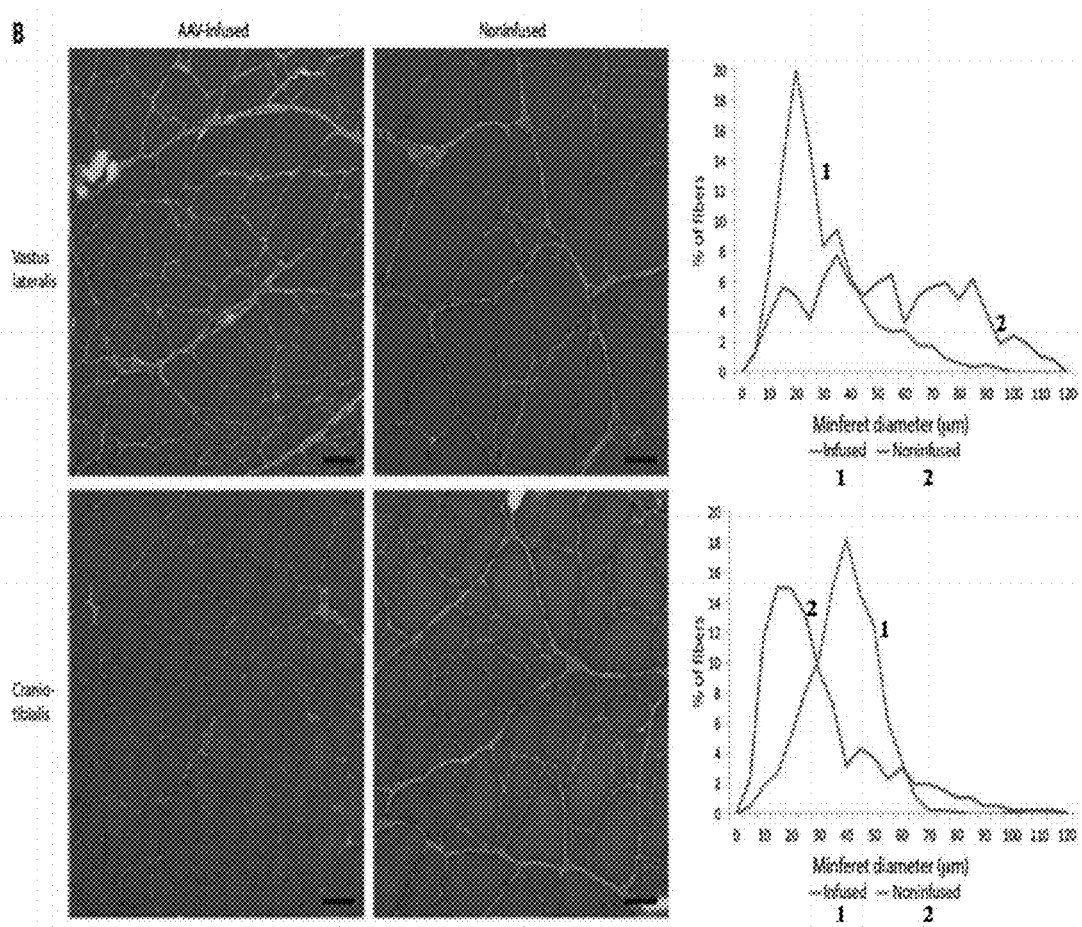
Figures 26A, 26B, 26C:
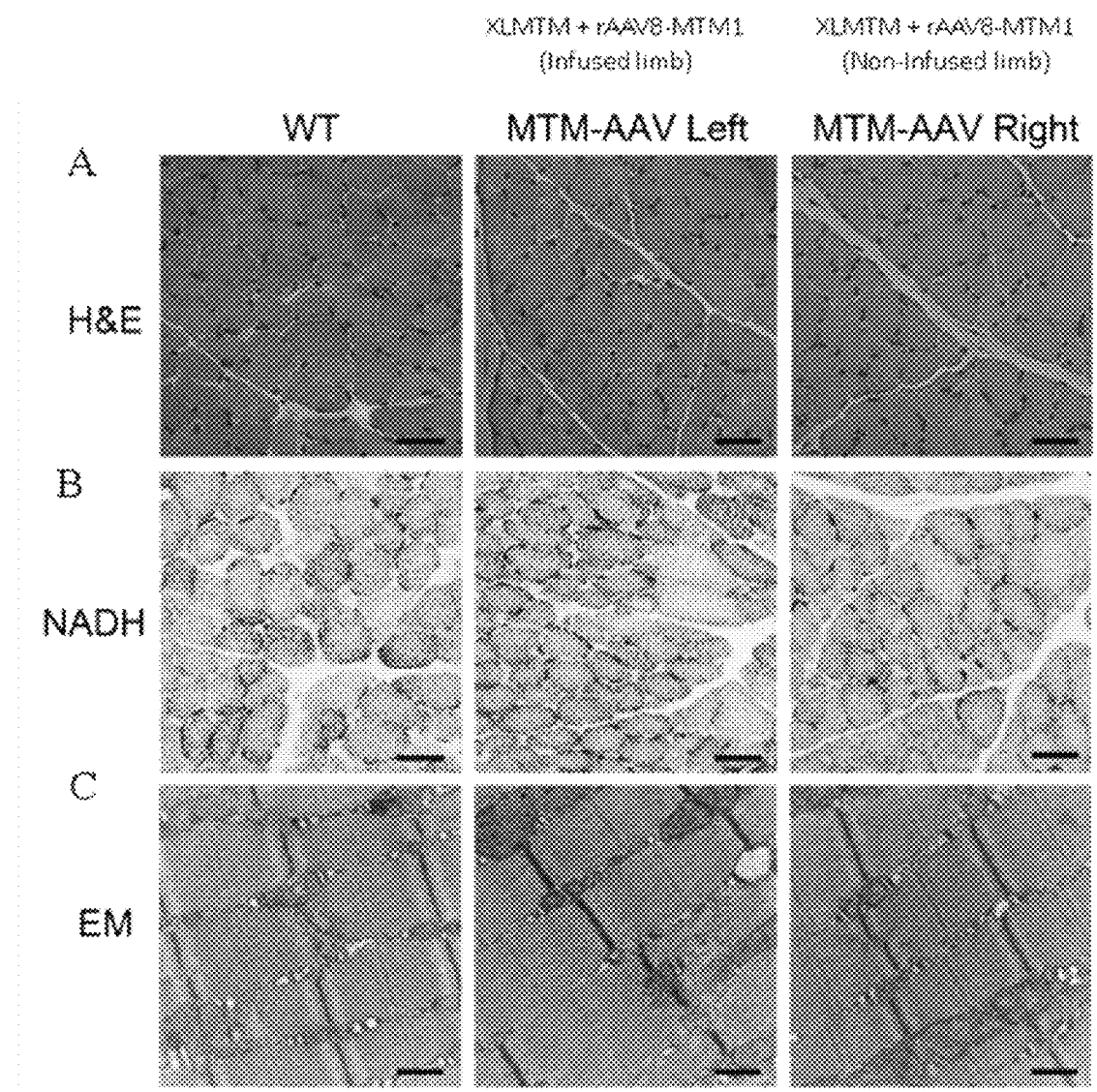
FIGS. 26A-26C depict the results of experiments demonstrating that intravenous myotubularin gene replacement therapy improves muscle fiber architecture in XLMTM dogs. Muscle cryosections from age-matched wild-type (WT) or rAAV8-MTM1 infused XLMTM dogs were assessed microscopically. Comparison is shown between the left (infused) hindlimb and the right (contralateral non-infused) limb.

In other experiments, a single intravascular infusion of rAAV8-MTM1 (2.5×10$^{12}$ vg/kg) was administered into the hindlimb saphenous vein under high pressure as described in each of three XLMTM dogs at 9 weeks-of-age. The contralateral limb was not infused. At 13 and 17 weeks-of-age muscle biopsies were obtained from hind and forelimbs, and muscle lysates probed with anti-myotubularin antibodies. Immunoblots demonstrated myotubularin transgene expression in all muscle samples taken from XLMTM dogs (FIGS. 25A-25B): four weeks after rAAV8-MTM1 infusions, the level of myotubularin expression in treated dogs (relative to WT expression) was increased. Infusion with rAAV8-MTM1 also showed improved myofiber architecture and increased myofiber size (FIGS. 26A-26C). Specimens taken from the infused limb showed a consistent fiber size and appearance, with a smaller average fiber size than is seen in WT muscle. In contrast, the non-infused limb displayed marked variation in fiber size with populations of very small and very large fibers, and two of the three animals displayed a larger average fiber size than was seen in the WT animals. The single biopsy from a non-infused limb that showed smaller fiber size than WT animals was taken adjacent to a myotendinous insertion site, which is known to locally affect fiber size and may not be characteristic of the majority of this muscle. Mislocalization of organelles was only seen in one of the three rAAV8-MTM1-infused dogs and was higher in the non-infused limb (FIGS. 6A-6B). Electron microscopy performed on quadriceps muscle samples from infused and non-infused limbs at 4 and 8 weeks post-treatment displayed appropriate sarcotubular organization, similar to what was seen following intramuscular injection. Electron microscopy of the biceps femoris muscle at the terminal time point revealed a decrease in sarcotubular organization in both the infused and non-infused hindlimb, with only approximately 1 triad seen per field in each muscle.

MTM1 Replacement Improves Strength of XLMTM Canine Muscle

Figures 5A, 5B, 5C, 5D, 5E, 5F, 5G:
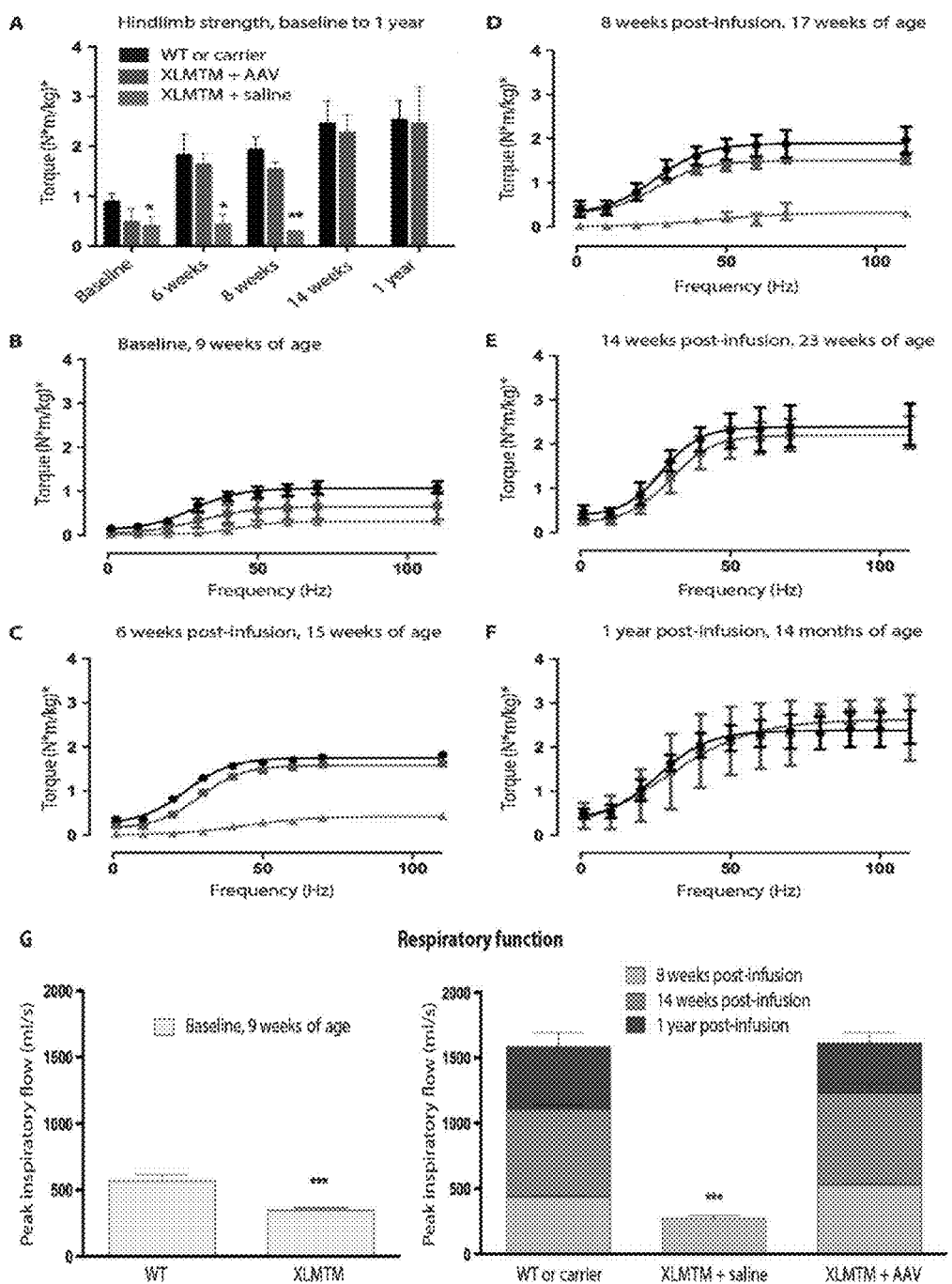
FIGS. 5A-5G the results of experiments demonstrating increase in hindlimb strength of XLMTM dogs after intravascular administration of AAV8-MTM1. Data are presented as means±standard deviation (SD) combined values of both limbs.

To measure function of the treated limbs, force transduction assays, originally developed to study canine muscular dystrophy, were used. FIG. 4B depicts an isometric contraction assay. Briefly, non-invasive electrical nerve stimulation, of differing frequencies, at the stifle joint (knee) of an anesthetized dog stimulates muscle contraction and foot flexion analogous to lifting off the ground during walking. The hind foot is affixed to a pedal mounted on the shaft of a force transducer so that measured torque reflects the strength of the lower limb muscles. Immediately prior to gene therapy at 10 weeks-of-age (baseline), XLMTM dogs were mildly weaker than unaffected WT littermates, and the two hind limbs of each dog performed equally (FIG. 4B). Measurements 4 and 6 weeks later showed that the limb strength of WT dogs more than doubled, consistent with normal muscular maturation (FIG. 4B and FIG. 5B). However, in XLMTM dogs, limbs injected with saline intramuscularly did not improve, so that the strength deficit relative to WT became worse.

Strength Improved after Intramuscular Administration of rAAV8-MTM1.

Each mutant limb injected with rAAV8-MTM1 strengthened significantly by 14 weeks-of-age (FIG. 4B). In the 2 dogs maintained until 16 weeks-of-age, the treated limbs continued to improve, reaching 80% of WT torque versus 30% for untreated limbs (FIG. 5B).

Figure 12A:
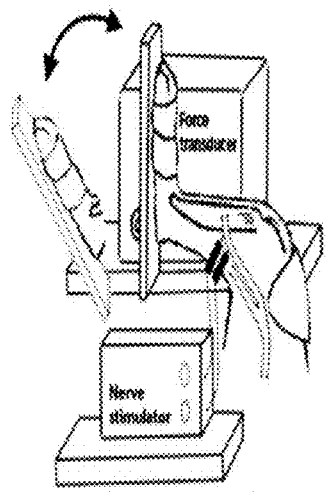
FIGS. 12A-12D depict the results of experiments demonstrating that targeted gene therapy with rAAV-MTM1 injected into the cranial tibialis muscle improves in vivo contractile response to repeated lengthening (eccentric) contractions in XLMTM dogs.
Figure 12B:
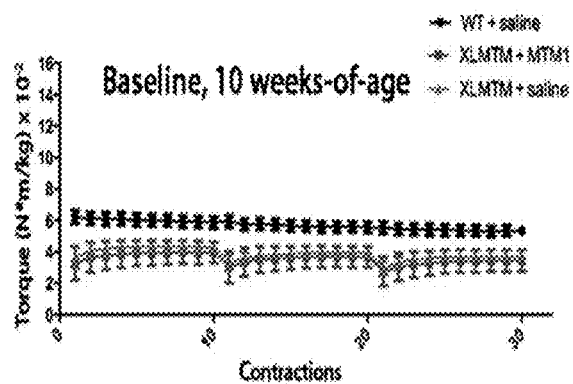
Figure 12C:
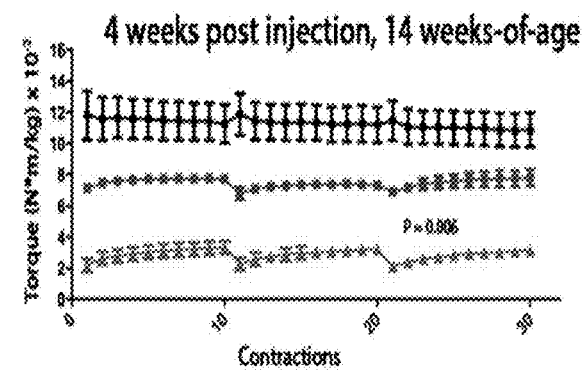
Figure 12D:
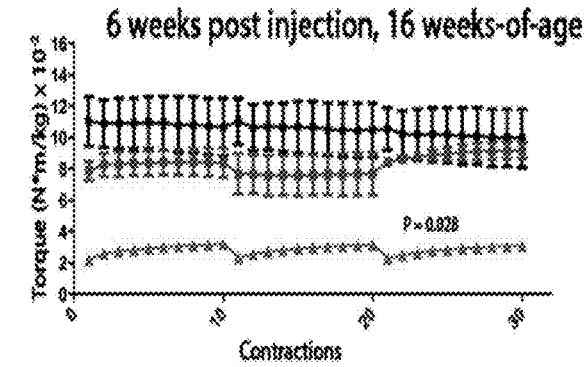

A dynamic eccentric contraction assay was also used to measure muscular performance during repetitive exercise. (FIG. 12A). When assessed by this test over time (i.e. age), the hind limbs of young WT dogs strengthened, while intramuscular saline-injected limbs of the three XLMTM dogs declined to about 20% relative to WT. Again, local rAAV8-MTM1 therapy greatly improved exercise performance; at 14 and 16 weeks-of-age, treated limbs achieved >70% of WT strength (FIG. 12B through FIG. 12D).

These results showed that a single injection of AAV8-MTM1 is efficacious in rescuing the function of an entire myotubularin-deficient muscle, prompting the assessment of an intravascular delivery approach.

Intravascular Administration of AAV8-MTM1 Rescues Muscle Pathology and Prolongs Survival of XLMTM Dogs.

Figures 7A, 7B, 7C, 7D:
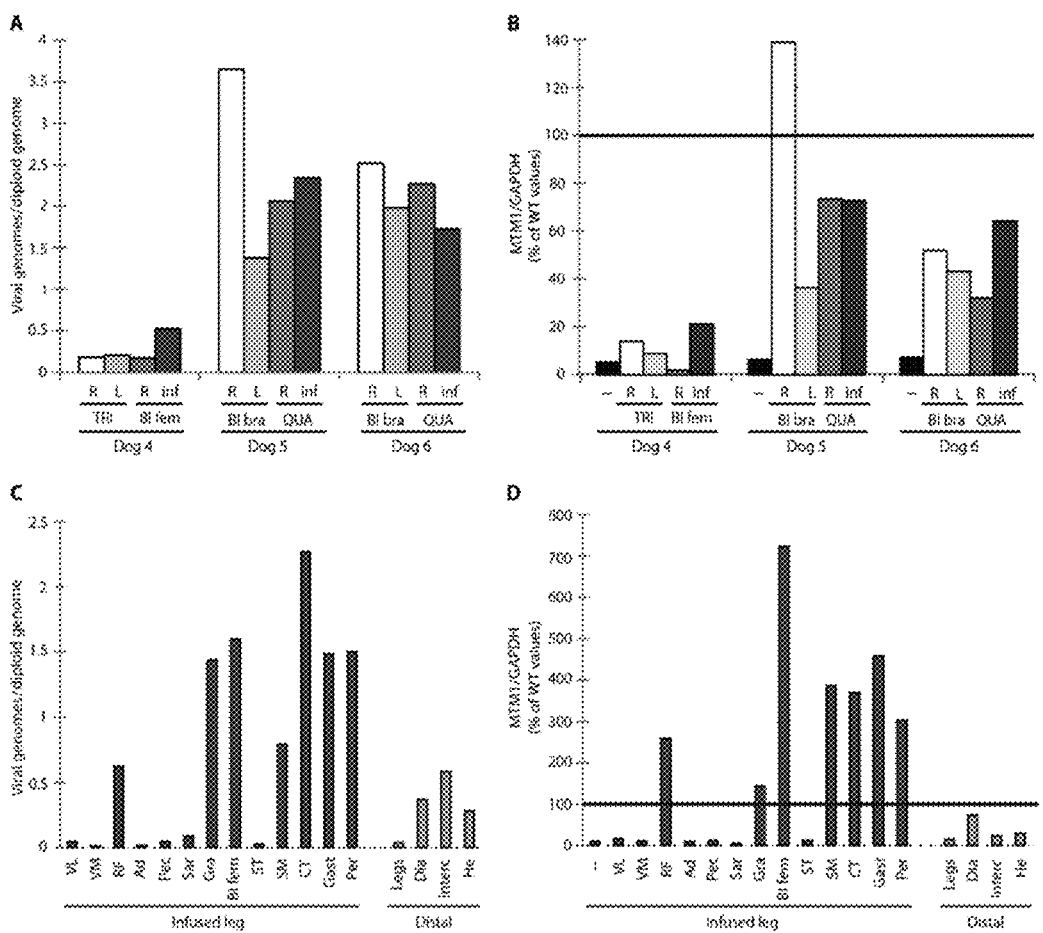
FIGS. 7A-7D depict the results of experiments demonstrating the biodistribution of AAV8 vector and the myotubularin transgene expression in XLMTM dogs infused with AAV8-MTM1.
Figure 14:
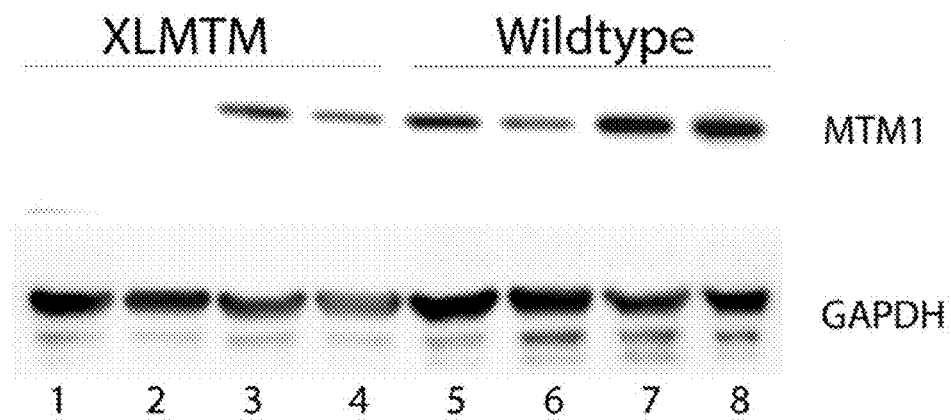
FIG. 14 represents the results of a western blot of myotubularin transgene expression in XLMTM dogs infused with AAV8-MTM1. The expression of canine MTM1 protein is shown relative to the housekeeping gene, GAPDH in whole muscle lysates probed with an anti-myotubularin antibody (see FIGS. 7A-D for expression levels in various muscles one year post-infusion). XLMTM muscle infused with saline only: lanes 1-2; XLMTM infused with AAV8-MTM1: lanes 3-4; and wild type muscles without infusion: lanes 5-8.
Figure 15:
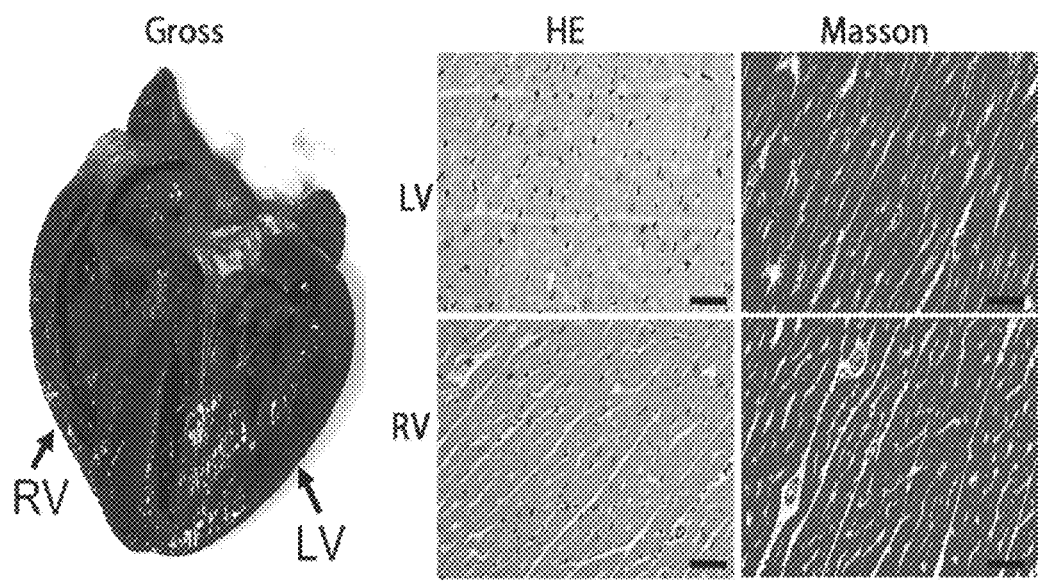
FIG. 15 displays the necropsy findings in the heart of an XLMTM dog 1 year following AAV8-MTM1 infusion. Pathological assessment of the heart of D4 at the gross (left panel) and microscopic (right panel) levels did not reveal histopathological or structural abnormalities. Legend: RV=right ventricle; LV=left ventricle; Mason=mason's trichrome stain. Size bars=40 µm.

AAV delivery by isolated limb perfusion allows widespread transduction of muscle groups in dogs and nonhuman primates. To test whether regional administration is sufficient to ameliorate muscle pathology in an entire limb, a single dose of AAV8-MTM1 ($2.5 \times 10^{13}$ vg/kg) was injected under high pressure into the saphenous vein of three 9-week-old XLMTM dogs, after applying a tourniquet around the hindlimb distal to the injection site to limit blood circulation during infusion. The tourniquet was released 5 min after injection. Treated dogs improved in strength rapidly after vector administration. In contrast to dogs injected intramuscularly, where only the muscles of the injected limb gained strength, high-pressure intravascular limb delivery of AAV8-MTM1 resulted in improved strength of both the infused and contralateral hindlimbs, which reached on average almost normal values 6 weeks after infusion (FIG. 5A and FIGS. 13A-13C). Similarly, peak inspiratory flow (PIF) (the fastest flow rate measured during inhalation) was strongly reduced in XLMTM dogs at 16 weeks of age, but was normal in treated dogs (FIG. 5B), indicating that the AAV8-MTM1 vector transduced respiratory muscles and improved their function. Most importantly, all treated dogs showed a marked improvement in survival, which extended far beyond the critical 18-week time point, when all untreated XLMTM dogs could no longer ambulate and needed to be euthanized. The first infused XLMTM dog (dog 4) survived in relatively good condition beyond 1 year and was sacrificed for analysis at 14 months of age. The other two dogs (dogs 5 and 6) remained ambulant and clinically robust beyond the age of 1 year, and were alive and healthy at the time of disclosure preparation (Movie 2, described below). Muscle biopsies were taken from the injected and contralateral hindlimbs (quadriceps and biceps femoris) and from the forelimbs (triceps and biceps brachii) of all treated dogs 4 weeks after infusion to analyze vector distribution, transgene expression, and histology. Intravenous administration of AAV8-MTM1 improved myofiber appearance and architecture in the treated limbs, which consistently showed an average fiber size only slightly reduced compared to wild-type muscles measured 4 weeks after infusion (FIG. 6A). In contrast, at 1 year after infusion, noninfused limbs displayed heterogeneity in muscle fiber size, with coexistence of small and large fibers (FIG. 6B). Electron microscopy performed on quadriceps muscle samples obtained from all infused limbs showed normalized sarcotubular organization, similar to what was observed after intramuscular injection (Table 2, listed below). The biceps femoris muscles of dog 4, analyzed at sacrifice, revealed a partially defective sarcotubular organization in both the infused and non infused hindlimb, with only about one triad per field in each muscle (Table 3, listed below). Real-time polymerase chain reaction (PCR) and Western blot analysis demonstrated both AAV8 vector (FIG. 7A) and myotubularin (FIG. 7B and FIG. 14) expression in all muscle samples obtained from all three treated dogs: 4 weeks after infusions, the level of myotubularin expression reached 21 to 72% of the wild-type control levels in the biceps femoris and quadriceps muscles in the injected limbs and 9 to 138% in the muscles (quadriceps, biceps femoris, triceps, and biceps brachii) of the non injected limbs. Expression levels were paralleled by VCN levels, which ranged from 0.52 to 2.35 in the biceps femoris and quadriceps muscles of the infused limbs and from 0.17 to 3.65 in the muscles of the non injected limbs (FIG. 7A). The biodistribution of AAV8-MTM1 was analyzed in dog 4 at necropsy. The VCN was, in general, higher in infused muscles (range, 0.01 to 2.27) than in distal muscles (range, 0.007 to 0.13; n=18), with the exception of the diaphragm, intercostal muscles, and heart, where it was detected a VCN of 0.37, 0.59, and 0.28, respectively (FIG. 7C). MTM1 protein levels were above the endogenous level in 7 of 13 muscles from the infused hindlimb and barely detectable in the contralateral and forelimb muscles (FIG. 7D), mirroring the VCN values and suggesting that very low amounts of myotubularin are sufficient to rescue muscle function. In the diaphragm and heart, myotubularin reached 64 and 13% of the wild-type values, respectively. The heart of dog 4 showed no signs of toxicity at histological examination (FIG. 15) and at the functional level, as assessed by electrocardiogram and echocardiography before necropsy. The histology of the liver (VCN: 0.63) was also normal, and myotubularin protein was undetectable. These data show that isolated limb perfusion was effective in delivering the AAV vector to the infused muscle groups but did not limit vector diffusion to other organs, including the rest of the skeletal musculature and the heart.

Movie 2, available at www dot sciencetranslationalmedicine dot org/cgi/content/full/6/220/220ra10/DC1 in a m4v format, comprises eight sections that illustrate a normal healthy control dog, two untreated XLMTM dogs and three XLMTM dogs (Dog 4, Dog 5 and Dog 6) treated with AAV8-MTM at different ages.

Section 1: A normal healthy dog is shown along with a XLMTM affected dog. The normal dog is moving very actively and trying to get a treat from the trainer's hand. The affected dog is lying on the floor with difficulties to ambulate and to stand for reaching toward the treat in the trainer's hand. After few trials, the healthy dog successfully gets the treat while the affected dog was clearly too weak to compete against him.

Section 2: An untreated dog, at 4 months of age, is lying on the floor having clear difficulties to ambulate.

Section 3: Another untreated dog, at 4 months of age, is shown a can of food by a trainer. The dog smells the can several times but does not seem interested in eating it.

Section 4: Dog 4, at 4 months of age, is seen very active and playing with a towel.

Section 5: Dogs 5 and 6, both at 6 months of age, are seen very active playing and jumping on each other.

Section 6: Dog 4 is seen again at 1 year of age, on a leash walking actively back and forth with his trainer then standing up to reach toward a piece of meat shown to him by the trainer.

Section 7: Dogs 5 and 6, both at 1 year of age post infusion, are seen playing very actively with a towel and chasing each others through a gymnastic lap that includes a tunnel and a step.

Section 8: Dogs 5 and 6, both at 1 year of age post infusion, are seen playing very actively and trying to steal a towel from each other's muzzle.

TABLE 2

Quantified Histological Findings in Dogs after Intravenous AAV.

| | Mean MinFeret Fiber Diameter (μm) | % Fibers with Internal Nuclei | % Fibers with Mislocalized Organelles |
|---|---|---|---|
| Control (WT) Animals | | | |
| Dog C1 | 31.0 (8.7-54.9) | 0 | 0 |
| Dog C2 | 31.1 (4.9-68.8) | 0.5 | 0 |
| Dog C3 | 26.2 (6.2-44.9) | 0.2 | 0 |
| Experimental Animals | | | |
| Dog 4 | | | |
| Infused Leg | 24.8 (3.6-65.0) | 1.7 | 5.6 |
| Non-infused Leg | 32.7 (6.0-65.8) | 6.3 | 34.1 |
| Dog 5 | | | |
| Infused Leg | 26.2 (5.5-61.4) | 0.6 | 0 |
| Non-infused Leg | 37.7 (6.3-73.8) | 0.8 | 0 |
| Dog 6 | | | |
| Infused Leg | 22.7 (2.9-53.1) | 0.9 | 0 |
| Non-infused Leg | 21.7 (3.1-71.2) | 2.0 | 0 |

TABLE 3

Quantified Histological Findings in Autopsy Tissue at 1 year after infusion.

| Muscle | Mean MinFeret Fiber Diameter (μm) | % Fibers with Internal Nuclei | % Fibers with Mislocalized Organelles |
|---|---|---|---|
| Dog 4 | | | |
| Infused Craniotibialis | 38.7 (6.2-97.8) | 1.3 | 0.3 |
| Non-infused Crantiotibialis | 30.8 (4.7-137) | 9.2 | 17.3 |
| Infused Vastus Lateralis | 30.0 (3.2-96.1) | 7.3 | 11.3 |
| Non-infused Vastus Lateralis | 54.1 (4.7-147.1) | 4.0 | 3.3 |

Immune Response Profile in XLMTM Dogs Following rAAV8-MTM1

Humoral Immune Response to Vector.

NAF, IgG and IgM titers measured from the sera before and after intramuscular (FIG. 16A) or intravenous regional limb (FIG. 16B) administration of rAAV8-MTM1 demonstrate that NAF and IgG titers increased one week following injections and remained elevated for up to 10 months. IgM titers decreased to pre-infusion baseline levels in XLMTM dogs given rAAV8-MTM1 by regional infusion.

Humoral Immune Response to MTM1 Transgene.

Figures 16A, 16B, 16C, 16D:
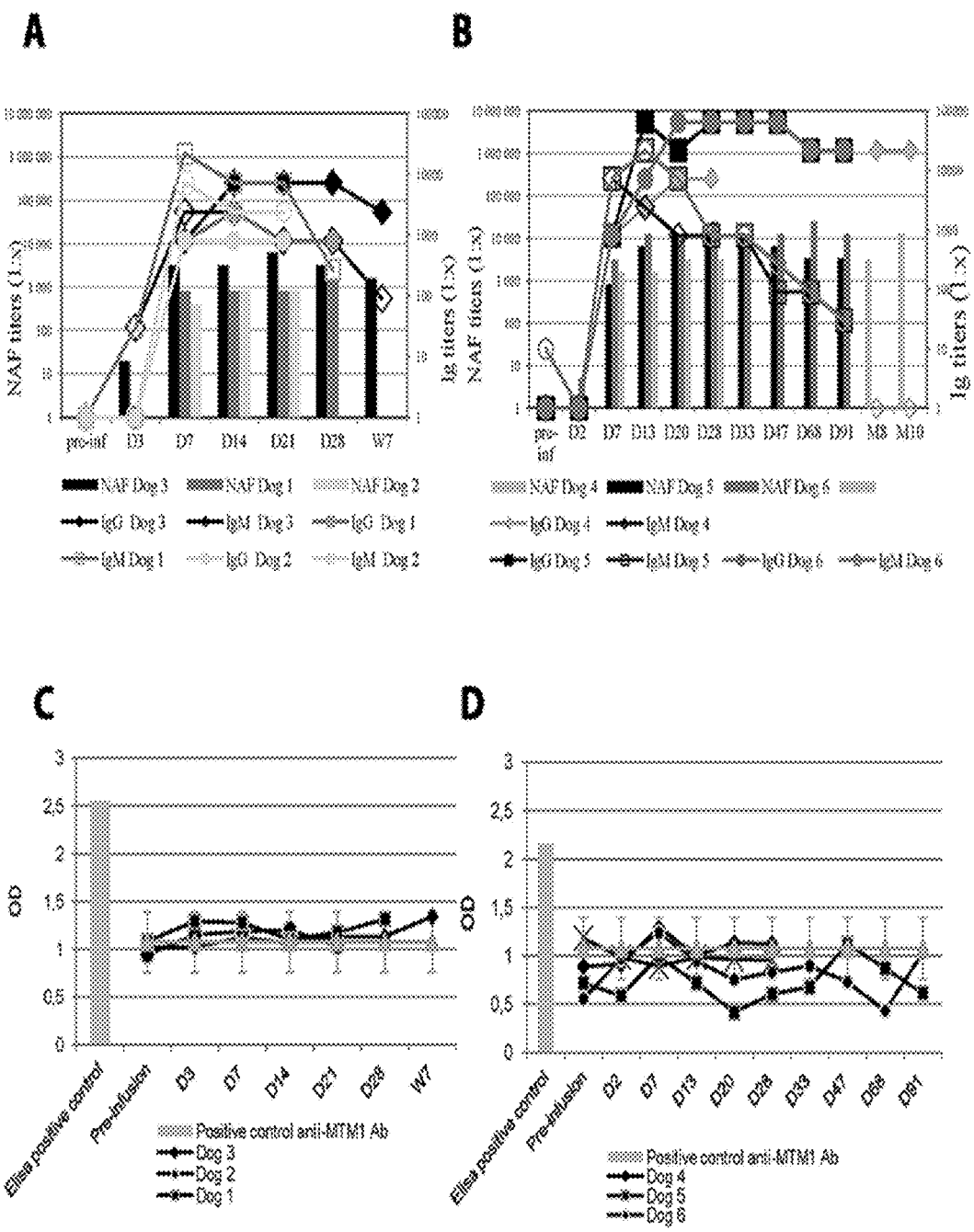
FIGS. 16A-16D depict the results of experiments demonstrating the humoral response specific to AAV8 and myotubularin in XLMTM dogs.

Compared to pre-infusion levels, elevations in IgG and IgM antibodies specific of MTM1 protein in sera were not observed in any XLMTM dogs given either intramuscular or intravenous infusions of rAAV8-MTM1 (FIG. 16C and FIG. 16D).

Cellular Immune Response to AAV Vectors or MTM1 Transgene.

Figure 17A:
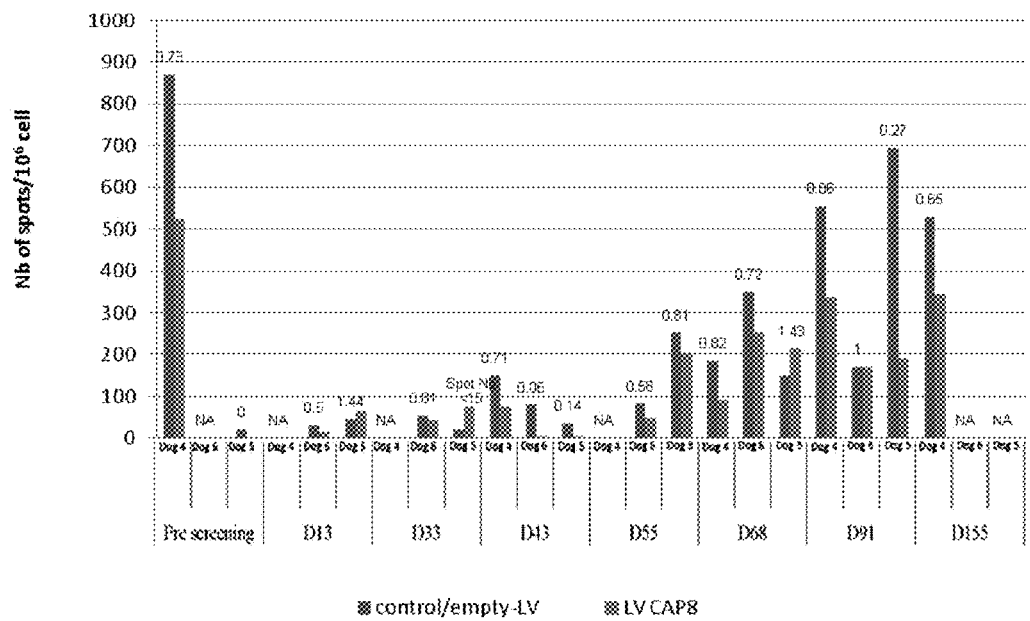
FIGS. 17A-17B depict the results of experiments demonstrating the cellular response to rAAV8 (FIG. 17A) or MTM1 protein (FIG. 17B) in XLMTM dogs. Values indicate the LV-VP1:LV-empty ratios. Results are expressed as spot-forming units/$10^6$ cells. Samples were considered positive for the antigen if the number of spots was greater than 1.5 times the corresponding control with LV-empty. Assays were scored if the number of spots under stimulation>15 spots per $2 \times 10^5$ PBMC. NA=Not applicable
Figure 17B:
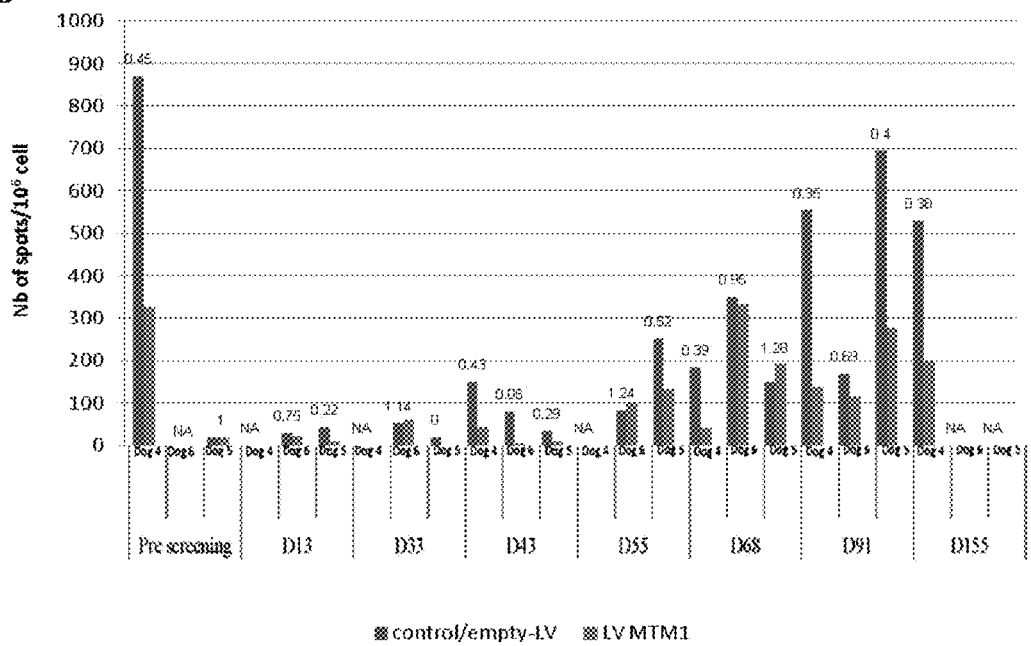
Figure 18:
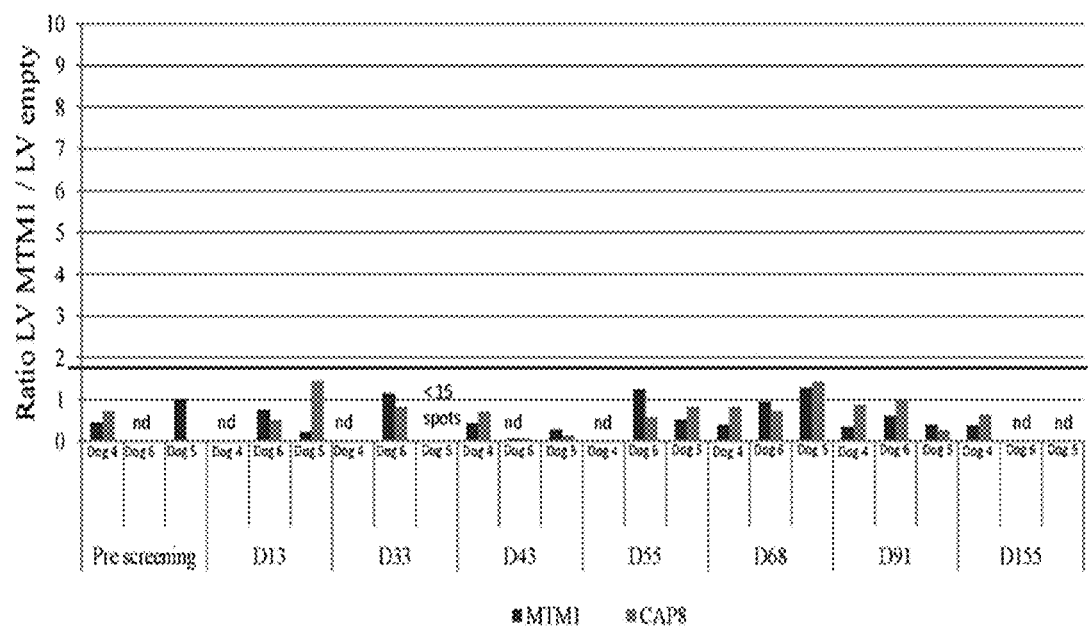
FIG. 18 depicts the results of experiments demonstrating the cellular response to AAV8 or MTM1 protein in XLMTM dogs. Results are expressed as ratio of number of spot-forming units secreting IFN-γ per $10^6$ PBMC after stimulation with LV-Cap8 or LV-MTM1 to number of spot-forming units secreting IFN-γ per $10^6$ PBMC after stimulation with LV-empty, for each dogs. Nd indicates not done. Samples were considered positive for the antigen if the number of spots was greater than 1.8 times thecorresponding control with LV-empty. Assays were scored if the number of spots under stimulation>15 spots per $2 \times 10^5$ PBMC. NA=Not analyzed.

Cell-mediated immune responses against the vector or the transgene product were tested by an interferon-g (IFN-g) enzyme-linked immunospot assay on peripheral blood mononuclear cells over a period of 155 days after vector administration. We were unable to detect any T cells specific to the vector capsid or the MTM1 protein in XLMTM dogs given intramuscular or intravenous AAV8-MTM1 (FIG. 17 and FIG. 18).

Inflammatory Immune Response.

Innate immune response profiles of cytokines IL2, IL6, IL8, IL10, IL15, TNF-α and IFN-γ before and after intramuscular or regional limb infusion with rAAV8-MTM1 are presented in Table 4 below. Of the three dogs, dog 1, dog 2 and dog 3, given intramuscular rAAV8-MTM1, dog 3 displayed elevated TNF-α levels (42.5-80.8 pg/ml) between Day 3 to Day 28 post-infusion. Notable elevated levels of innate responses were not observed in other animals, including dog C, an untreated XLMTM control dog. Following regional rAAV8-MTM1 infusion, transient elevations in IL2 and IL15 (743.5 and 119 pg/ml, respectively) were observed in one dog, dog 6, 6 hrs after infusion.

TABLE 4

Innate immune responses after intramuscular or regional limb administration of AAV8-MTM1 in XLMTM dogs (dogs 1 to 6) and an untreated XLMTM dog (dog C).

| | Dog | Timing | IL2 (pg/ml) | IL6 (pg/ml) | IL8 (pg/ml) | IL10 (pg/ml) | IL15 (pg/ml) | TNF-α (pg/ml) | IFN-γ (pg/ml) |
|---|---|---|---|---|---|---|---|---|---|
| I.M. injection | Dog C | Pre-infusion | 110.5 | 103.8 | 1587 | 29 | 63.5 | 86.8 | 9.5 |
| | | D3 | 97 | 91 | 819.3 | 28 | 60.8 | 74.8 | 9.5 |
| | | D14 | 84.6 | 74 | 1797 | 29 | 57.8 | 68.5 | 9.5 |
| | | D21 | 81.5 | 80 | 886.8 | 29.5 | 52.8 | 60 | 9.5 |
| | | D28 | 91.5 | 98.3 | 664.8 | 22 | 89 | 73.3 | 9 |
| | Dog 1 | Pre-infusion | 19 | 23 | 255 | 26.3 | 30.5 | 33.5 | 7 |
| | | D1 | 18.6 | 21.8 | 4417.5 | 33 | 20.8 | 28 | 7 |
| | | D3 | 20.3 | 23 | 4257.9 | 35 | 27 | 36.5 | 6.5 |
| | | D7 | 19.3 | 23 | 3393 | 33.5 | 27.5 | 37 | 6.5 |
| | | D14 | 19.5 | 23.5 | 2616.9 | 33 | 26.5 | 36 | 6 |
| | | D21 | 16 | 19.5 | 4076.4 | 36 | 22.5 | 29.5 | 7.3 |
| | | D28 | 17.8 | 19.3 | 3375.9 | 35 | 21 | 28.5 | 7.5 |
| | Dog 2 | Pre-infusion | 16.5 | 21.5 | 3255.9 | 33 | 21 | 28 | 6.8 |
| | | D1 | 13 | 17.5 | 3907.5 | 29 | 18.5 | 23 | 6.3 |
| | | D3 | 13.6 | 18 | 2709 | 33.5 | 18 | 25.8 | 7.5 |
| | | D7 | 15.8 | 22.3 | 4977 | 27.5 | 26 | 29 | 6.5 |
| | | D14 | 13.5 | 15 | 3115.5 | 32.5 | 19 | 23 | 6.5 |
| | | D21 | 20 | 24 | 2376 | 32.5 | 33 | 34.5 | 8.3 |
| | Dog 3 | Pre-infusion | 12.8 | 13 | 2472.9 | 27.5 | 15.5 | 19.5 | 7.3 |
| | | D1 | 13 | 16 | 4586.4 | 32.8 | 16 | 21 | 7.5 |
| | | D3 | 21.8 | 28 | 405 | 35.5 | 26.5 | 42.5 | 5.5 |
| | | D7 | 20 | 27.5 | 803.4 | 31.5 | 23.5 | 44.3 | 5.8 |
| | | D14 | 21.8 | 27.5 | 832.5 | 33.3 | 25.8 | 55.8 | 5 |
| | | D21 | 22.3 | 31 | 283.5 | 34 | 28.5 | 80.8 | 6 |

TABLE 4-continued

Innate immune responses after intramuscular or regional limb administration of AAV8-
MTM1 in XLMTM dogs (dogs 1 to 6) and an untreated XLMTM dog (dog C).

|  | Dog | Timing | IL2 (pg/ml) | IL6 (pg/ml) | IL8 (pg/ml) | IL10 (pg/ml) | IL15 (pg/ml) | TNF-α (pg/ml) | IFN-γ (pg/ml) |
|---|---|---|---|---|---|---|---|---|---|
| | | D28 | 18.5 | 24.5 | 565.5 | 33.8 | 21.3 | 54.5 | 6 |
| | | W7 | 12.5 | 17.5 | 2070 | 23.3 | 18.5 | 22.3 | 6.3 |
| Regional infusion | Dog C | Pre-infusion | 110.5 | 103.8 | 1587 | 29 | 63.5 | 86.8 | 9.5 |
| | | D3 | 97 | 91 | 819.3 | 28 | 60.8 | 74.8 | 9.5 |
| | | D14 | 84.6 | 74 | 1797 | 29 | 57.8 | 68.5 | 9.5 |
| | | D21 | 81.6 | 80 | 886.8 | 29.5 | 52.8 | 60 | 9.5 |
| | | D28 | 91.5 | 98.3 | 664.8 | 22 | 89 | 73.3 | 9 |
| | Dog 4 | Pre-infusion | 18 | 23.8 | 4865.3 | 46 | 32.8 | 32.5 | 10.3 |
| | | D0 + 6 h | na | na | na | na | na | na | na |
| | | D1 | 16 | 21.5 | 3415.6 | 40 | 31 | 31.5 | 10.5 |
| | | D3 | 18.3 | 23.3 | 4747.5 | 41 | 32 | 35.5 | 10.5 |
| | | D7 | 23.5 | 32.5 | 2157.3 | 43.3 | 34.5 | 45.8 | 10 |
| | | D14 | 15 | 18 | 566.5 | 46.5 | 28 | 28 | 10 |
| | Dog 5 | Pre-infusion | 68 | 113.5 | 180.3 | 27 | 83.8 | 143 | 11 |
| | | D0 + 6 h | 81 | 143.5 | 744.5 | 33.5 | 103 | 202 | 10 |
| | | D1 | 117.5 | 125.8 | 304 | 34 | 93.3 | 197 | 10 |
| | | D2 | 65.8 | 112 | 1310.3 | 34 | 84 | 148.5 | 10.3 |
| | | D7 | 68.5 | 113.5 | 689.3 | 34.5 | 72.5 | 139.5 | 11.3 |
| | | D13 | 49.3 | 34 | 1665 | 29.5 | 45.8 | 20.5 | 8.5 |
| | Dog 6 | Pre-infusion | 23.5 | 22.5 | 255.5 | 29.5 | 23.5 | 30.5 | 12.5 |
| | | D0 + 6 h | 743.5 | 20.5 | 445 | 31 | 119 | 46.8 | 13 |
| | | D1 | 14.8 | 15.5 | 303.5 | 34 | 13.5 | 19.8 | 12 |
| | | D2 | 15 | 19 | 993.5 | 36 | 14.5 | 20.8 | 12.5 |
| | | D7 | 12.8 | 15 | 170 | 35 | 13.5 | 20.8 | 11 |
| | | D13 | 14 | 20.8 | 988 | 34.5 | 16 | 20.5 | 16.5 | na: not applicable

Systemic Mtm1 Delivery Improves Growth and Survival of Myotubularin-Knockout Mice FIGS. 1A-1E demonstrate that intravascular delivery of rAAV-Mtm1 in myotubularin-deficient mice improves lifespan and body growth. Myotubularin-deficient mice were injected with rAAV-Mtm1 at $3 \times 10^{13}$ viral genomes per kg (vg/kg) at 3 (KO+AAV, n=12) and 5 weeks of age (KO Late+AAV, n=12) during a 6 months follow-up study. Both survival (FIG. 1A) and body weight (FIG. 1B) is improved by treatment. FIG. 1C depicts the mass of representative skeletal muscles of KO-Mtm1 mice 2 weeks after injection of saline (KO+saline, n=4) and 6 months (n=10 after injection of rAAV-Mtm1 (KO+AAV, n=7, and KO Late+AAV, n=8). Values were normalized to muscle mass of age-matched, saline-injected WT mice (n=10), taken as 100%. This data again demonstrates that treatment increases muscle size. Similarly, myotubularin protein quantification by immunoblot compared to endogenous levels (line=1), demonstrates that treatment increased myotubularin content.

FIGS. 2A-2B demonstrate that Mtm1 gene replacement therapy corrects the internal architecture and hypotrophy of skeletal muscle fibers in myotubularin-knockout mice. Mice were injected with either saline (+saline) or rAAV-Mtm1 vector (+AAV). Sections were obtained after 2 weeks (5 weeks of age) and 6 months of treatment. FIG. 19A shows the cross-sections from tibialis anterior (TA) muscle stained with hematoxylin and eosin (HE) and NADH-TR, and by immunofluorescence with antibodies against DHPR1α and dysferlin. The data in FIG. 2B depicts the mean diameter of muscle fibers from TA and biceps brachii muscles from mice injected with either saline or rAAV-Mtm1 after 2 weeks (left graph) and 6 months of treatment (right graph).

FIG. 3A-3C demonstrate that gene replacement therapy with rAAV8-Mtm1 improves strength, activity and long-term survival in myotubularin deficient mice. Whole-body spontaneous mobility of normal (WT+saline), mutant (KO+saline) and AAV-treated mutant (KO+AAV-Mtm1) mice 2 weeks (5 weeks of age) and 6 months after PBS or vector injection was measured. The distance covered over the 90-min test was assessed using an open field actimeter. FIG. 3A demonstrates that treatment increases distance traveled. FIG. 3B depicts the escape test measurements in the 5 groups of mice, again demonstrating that treatment increases function. FIG. 3C demonstrates the specific tetanic force of isolated EDL muscles from KO mice injected at an early and late stage of the disease 6 months after vector delivery compared to saline-injected KO and WT littermates, showing again increased function in treated animals.

FIGS. 9A-9C demonstrate that systemic gene replacement therapy ameliorates pathological hallmarks of myotubular myopathy in skeletal muscles. Constitutive Mtm1 knockout mice (KO-Mtm1) at 3 weeks of age received a single intravenous injection of rAAV-Mtm1 as described elsewhere herein. Saline injected KO-Mtm1 and WT mice served as controls. Distribution of myofiber diameters of tibialis anterior (TA, FIG. 9A, upper panels) and biceps brachii (BI, FIG. 9B lower panels) muscles at 2 weeks (5 weeks of age) and 6 months post-injection in the two group of animals (3 weeks and 5 weeks of age at injection), showing that treatment restored fiber diameter to wild type distributions. The percentage of myofibers with internal nuclei was quantified in tibialis anterior muscle and biceps brachii of mice from the various treatment conditions (FIG. 9B)

Systemic Administration of MTM1

The data presented herein document long-lasting benefits of a single systemic administration of rAAV-mediated myotubularin gene replacement therapy in mouse models of XLMTM, a fatal congenital myopathy. Use of the muscle-specific desmin promoter to drive transgene expression was validated by equivalent results in whole-body and muscle-restricted knockout mice. Treatment with rAAV-Mtm1 reversed defects in skeletal muscles throughout the body, and promoted survival and normal growth. As assessed by histology, muscle strength, and global motor activity, gene therapy restored a nearly normal phenotype in myotubularin-deficient mice for at least one year.

Protein expression in response to varying amounts of rAAV-Mtm1 vector assessed several months after injection indicated that myotubularin production was gene dose-dependent. At a higher vector level, the amount of myotubularin in treated KO-Mtm1 mice exceeded that in WT at 2 weeks post-injection, and by 6 months was more than 7-fold above normal in muscles throughout the body. This potent response could be a potential concern because elevated expression of the homologous lipid phosphatase, myotubularin MTM-1 in Caenorhabditis elegans interferes with phagocytosis of apoptotic cells. Failure to remove cell corpses may exacerbate autoimmunity and other disease processes. In addition, it was found previously that elevated levels of myotubularin in mouse myofibers can lead to the accumulation of internal membrane saccules. However, in the present study such pathological features were not evident. Furthermore, at a 6-fold lower rAAV-Mtm1 vector dose, the quantity of myotubularin protein in skeletal muscles of mKO-Mtm1 mice 12 months post-injection was similar to WT, and the muscular structure and function of treated animals appeared nearly normal. The threshold myotubularin content required for therapeutic benefit may be considerably lower. For example, mice engineered to have only trace myotubularin activity, due to a missense mutation that also interferes with RNA splicing, survive 8 times longer than absolute myotubularin-knockout mutants. These findings suggest gene dose can be adjusted to express sufficient myotubularin enzymatic activity for efficacy, while avoiding potential side effects of supra-physiological production.

Local rAAV-mediated myotubularin gene therapy to a limb muscle of young XLMTM dogs yielded conspicuous improvements in muscle gross morphology, myofiber size, and subcellular architecture compared to untreated limbs. Intravenous infusion with rAAV-MTM1 resulted in systemic effects demonstrated by robust improvement in histopathology, sarcotubular organization and normalization of muscular strength. Remarkably, infused XLMTM dogs remained robust with improved survival beyond 18 weeks-of-age, with the first infused dog surviving for more than a year. Although pretreatment muscle biopsies were not obtained from these dogs, it is noted that skeletal muscles of myotubularin-deficient mice show significant sarcotubular disorganization by two weeks-of-age. Thus, if similar disorganization is evident in the dog muscles during early maturation, these findings suggest that delivery of an MTM1 vector can reverse established pathological changes in mutant muscle and restore normal structure.

From a clinical perspective, the most important observation is the extraordinary and rapid functional improvement following local or intravenous regional infusion of AAV8-MTM1 gene therapy. Untreated limb muscles of affected male dogs became progressively weaker than those of control littermates. By contrast, as measured in isometric and eccentric contraction tests, the strength of vector-injected limbs gained significantly by 4 weeks and reached 70-80% of normal at 6 weeks. This finding holds true for intramuscular or intravenous administration of rAAV8-MTM1. In the present study, regional intravenous infusion of vector suspended in saline under pressure against a tourniquet resulted in significant "leak" above the level of the tourniquet with vector transduction of non injected contralateral limb muscles. The findings presented herein are in contrast to the lack of vector transduction of contralateral limbs or organs in a canine model of hemophilia following regional limb perfusion with AAV2 at comparable doses. Reasons for these differences are not clear. Although blood flow was monitored using ultrasound above and below the tourniquet, the possibility of collateral circulation or of tourniquet slippage during the 10-minute infusion cannot be excluded.

The detailed mechanism by which myotubularin gene therapy corrects the muscle defects of mutant mice and dogs is not yet known. Important functions controlled by members of the myotubularin phosphoinositide 3-phospatase family include: endosomal and membrane trafficking and remodeling; surface localization of receptors and integrins; cytoskeletal dynamics; ion channel activity; and cell survival or apoptosis. Ablation of myotubularin in zebrafish or mice elevates PI(3)P in muscle. This, in turn, inhibits phosphorylation of the serine/threonine kinase AKT, a key signal transduction enzyme regulated by phosphoinositide second messengers. The precise pathway(s) by which this aberrant signaling leads to muscle cell failure in XLMTM remains conjectural. However, expression profiling supports histological observations pointing to remodeling of matrix, membrane, and cytoskeletal architecture as factors responsible for disorganization of organelles and muscular hypotrophy.

A cellular feature closely associated with the muscular dysfunction in XLMTM is the disorganization of T-tubules. These specialized membranous structures play an essential role in excitation-contraction coupling, by which nerve signals received by skeletal muscles are transmitted over the sarcolemma as an action potential (AP). The AP is sensed by the dihydropyridine receptor in the T-tubule membrane which initiates release of calcium via the ryanodine receptor from the sarcoplasmic reticulum. The increased cytosolic calcium concentration activates the actin/myosin. Restoration of normal T-tubule architecture correlates with the potent effect of myotubularin gene therapy on muscle strength in murine and canine mutants.

Whatever the mechanistic basis, the beneficial results of gene therapy in the animal models encourage future steps towards clinical translation. The data presented herein highlight the sustained expression of myotubularin in muscles of mutant small- and large-animal models treated with a single dose of recombinant adeno-associated virus. Genomes of rAAV vectors persist in transduced cells mainly as intranuclear concatameric episomes. This mode facilitates long-term correction of somatic cells, especially those that do not undergo rapid turnover. The rate of skeletal myofiber replacement in XLMTM patients is not known. However, in contrast to Duchenne muscular dystrophy (DMD), the low degree of tissue inflammation associated with XLMTM invites speculation that muscle turnover is comparable to that in unaffected individuals. Normal skeletal myocytes are long-lived; birth dating of human muscle cells, based on $^{14}$C levels in people who lived through the era of atmospheric nuclear testing, gave an average age of 15.1 years.

Immune responses to rAAV viral capsids or to the transgene product can persist for years. If immune reactions appear problematic, they potentially may be controlled by choice of administration route or by treatments to induce immune tolerance. In the XLMTM dog, adverse immune responses to either the vector (AAV8) or the transgene (MTM1 protein) were not observed in the present study. Interestingly, long-term expression of the MTM1 transgene was observed in the absence of detectable humoral or cellular immune responses against the restored protein, demonstrating in this animal model the lack of transgene-driven immune response.

It is anticipated that the clinical development of myotubularin gene replacement therapy will begin with local or loco-regional delivery. Targeting of wrist and hand muscles to enable control of a wheelchair and communication devices might improve quality of life for XLMTM patients. Furthermore, most patients are ventilator-dependent and require continuous management. Targeted injection of the diaphragm could relieve this burden and potentially decrease mortality.

The sustained benefit of gene therapy in myotubularin-knockout mice suggests that systemic treatment of human patients eventually will be feasible. It is project that this could be carried out shortly after birth to decrease the risk of immune reaction. Molecular assays are available to rapidly identify MTM1 mutations in symptomatic newborns or prenatally. Systemic vector delivery in older individuals also appears plausible, as evidenced by a recent study using rAAV8-mediated gene transfer in hemophilia B. Overall, the positive safety record of rAAV clinical trials, in which over 300 human subjects have enrolled since the mid-1990s, together with the completion of a Phase I clinical trial in DMD using an improved vector for gene therapy of muscle diseases, stimulate optimism for successful translation in XLMTM.

Example 2

Effects of Systemic AAV-MTM1 on Muscles of Respiration

The diaphragm is a parachute-shaped skeletal muscle that is the primary muscle used in respiratory inspiration. The diaphragm extends across the bottom of the rib cage, separating the thoracic cavity from the abdominal cavity. During inhalation, the diaphragm contracts, reducing thoracic pressure and volume and causing air to be pulled into the lungs. During exhalation, the diaphragm relaxes and elastic recoil of the lungs occurs. The diaphragm is weakened in those with XLMTM, thereby leading to respiratory dysfunction. Given the location of the diaphragm, it is difficult, invasive, and often dangerous to provide local delivery of therapeutics through intramuscular delivery to the diaphragm. It is described herein, that system delivery of MTM1 surprisingly increases the strength and function of the diaphragm in subjects with MTM1 deficiency.

Figure 27A:
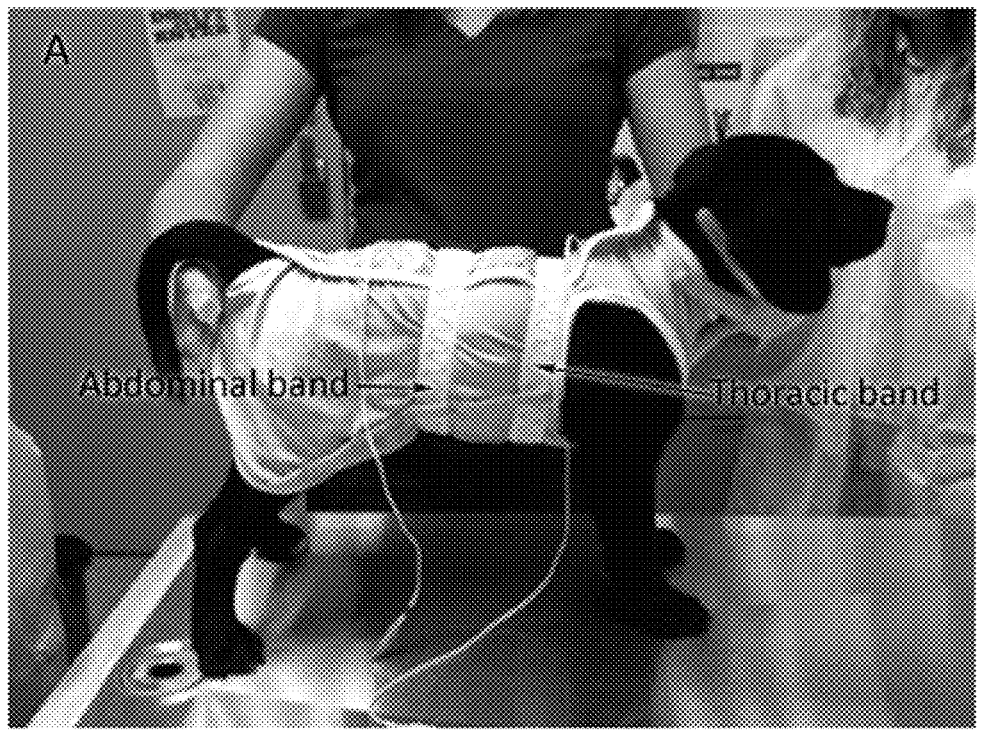
FIGS. 27A-27B are a set of images depicting the use of Respiratory Impedance Plethysmography (RIP) to measure diaphragm strength.
Figure 27B:

The studies presented herein measure diaphragm strength using Respiratory Impedance Plethysmography (RIP). Canine subjects were fitted with a jacket with wired bands placed at the thorax and abdomen (emka Technology). Changes in low impedance current passed through the bands are interpreted as changes in volume. (FIGS. 27A-27B). Anesthetized dogs were challenged with the respiratory stimulant, doxapram chloride. Doxapram acts centrally to stimulate respiration and thus allows for the assessment of the at-work diaphragm.

Figure 28:
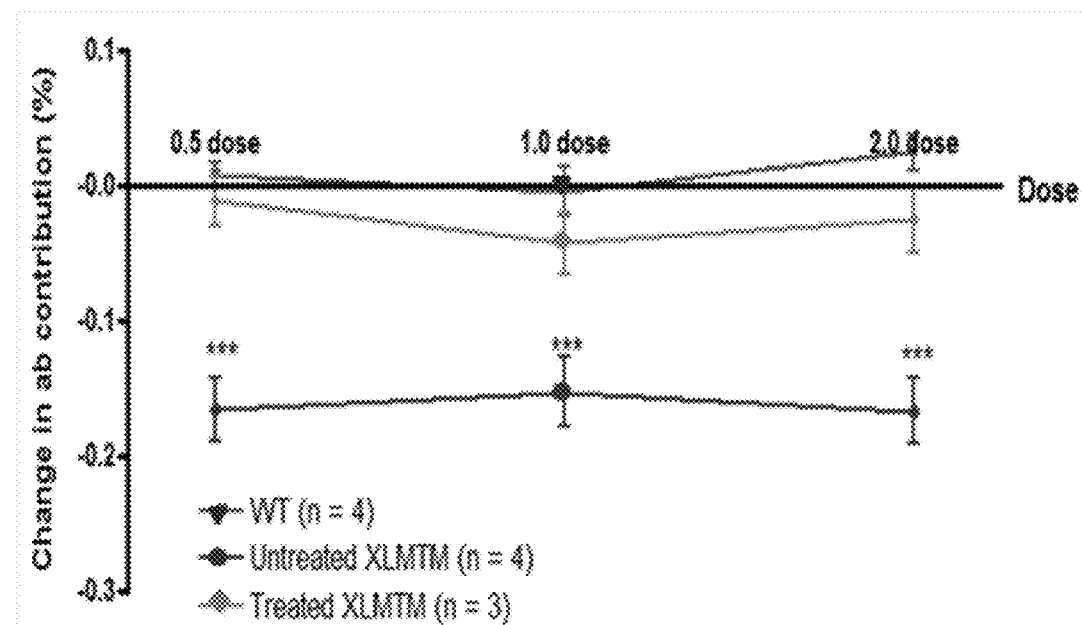
FIG. 28 is a graph depicting the results of experiments demonstrating that systemic AAV8-MTM1 delivery improves movement of diaphragm muscle in XLMTM subjects.

FIG. 28 depicts the change in percent abdominal contribution in response to doxapram dose, as compared to baseline in dogs at 16 weeks of age. The data depicted in FIG. 28 demonstrates that systemic treatment with AAV8-MTM1 in XLMTM dogs improves the movement of muscle diaphragm such that the change in abdominal contribution is not different from wild type.

Figure 29:
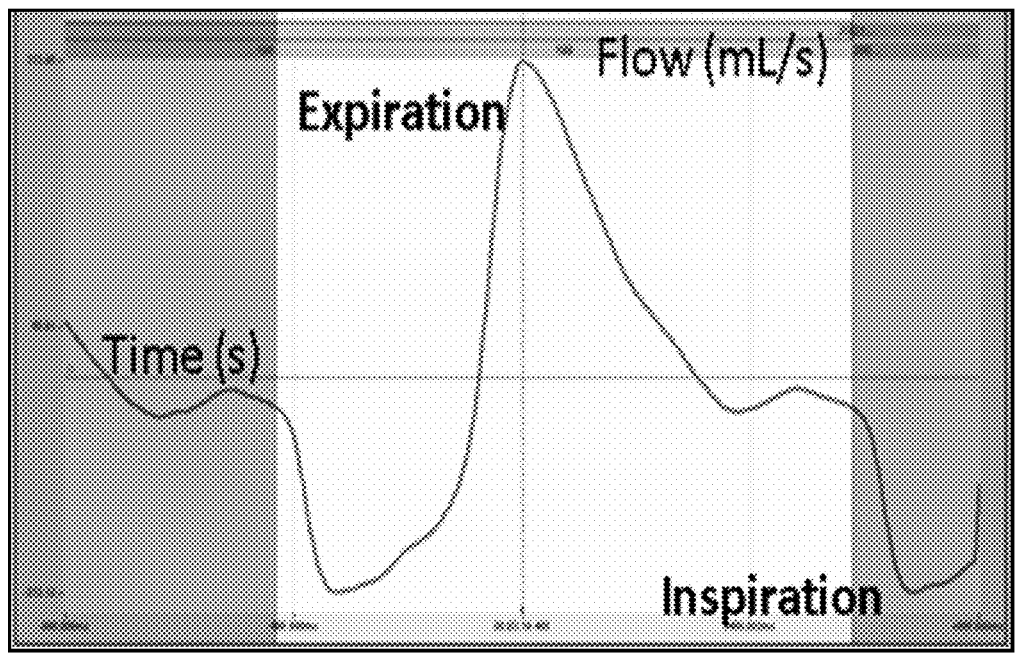
FIG. 29 is a schematic of flow versus time as measured by a pneumotach. The area under the curve is used to calculate volume

In other experiments, the tidal breathing flow-volume loop (TBFVL) was used to diagnose respiratory dysfunction. TBFVLs were developed to assess respiratory function in infants, where maximal voluntary effort is difficult. It has then adapted for use in cats and dogs. In normal dogs, the loop is D-shaped. TBFVLs are derived from pneumotach measures of airflows. A pneumotach is used to measure airflow after administration of 1.0 mg/kg doxapram. As shown in FIG. 29, the volume is determined by finding the area under the curve of flow over time. Measures were then adjusted for weight and averaged.

Figure 30:
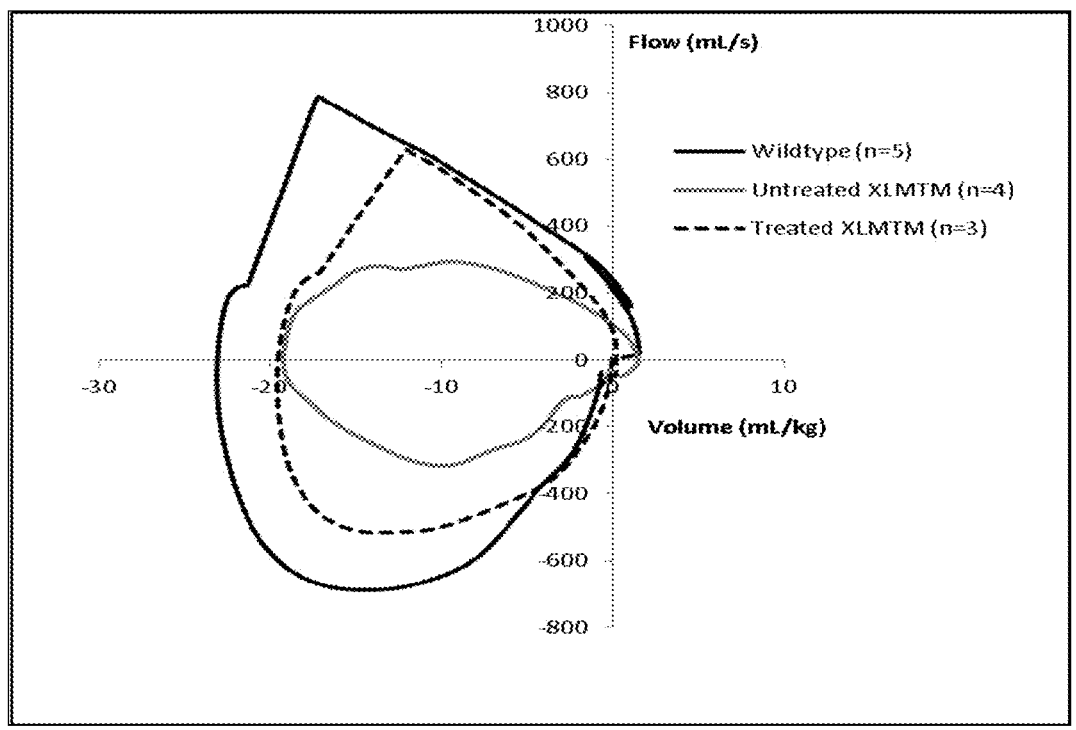
FIG. 30 is a graph depicting the results of experiments demonstrating that the TBFVL of XLMTM subjects treated with systemic AAV8-MTM1 is improved over untreated subjects, thereby revealing improved diaphragm function.
Figure 31:
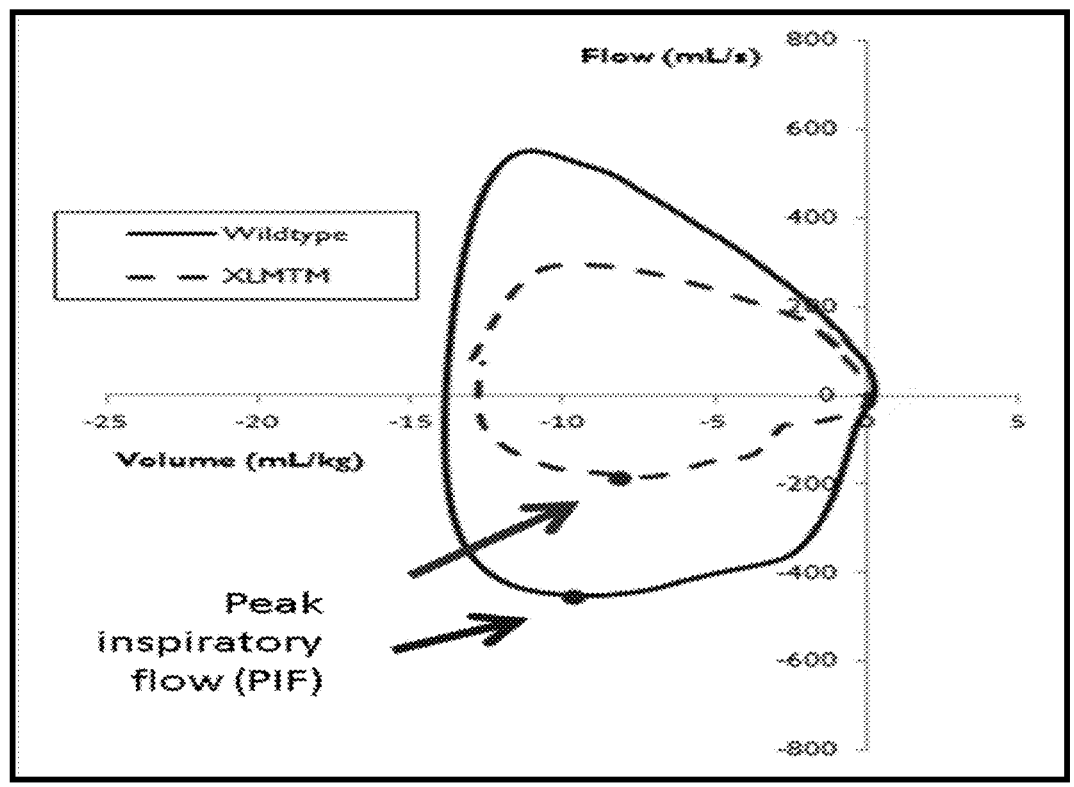
FIG. 31 is a graph depicting the TBFVL and the peak inspiratory flow of wild type and XLMTM dogs.
Figure 32:
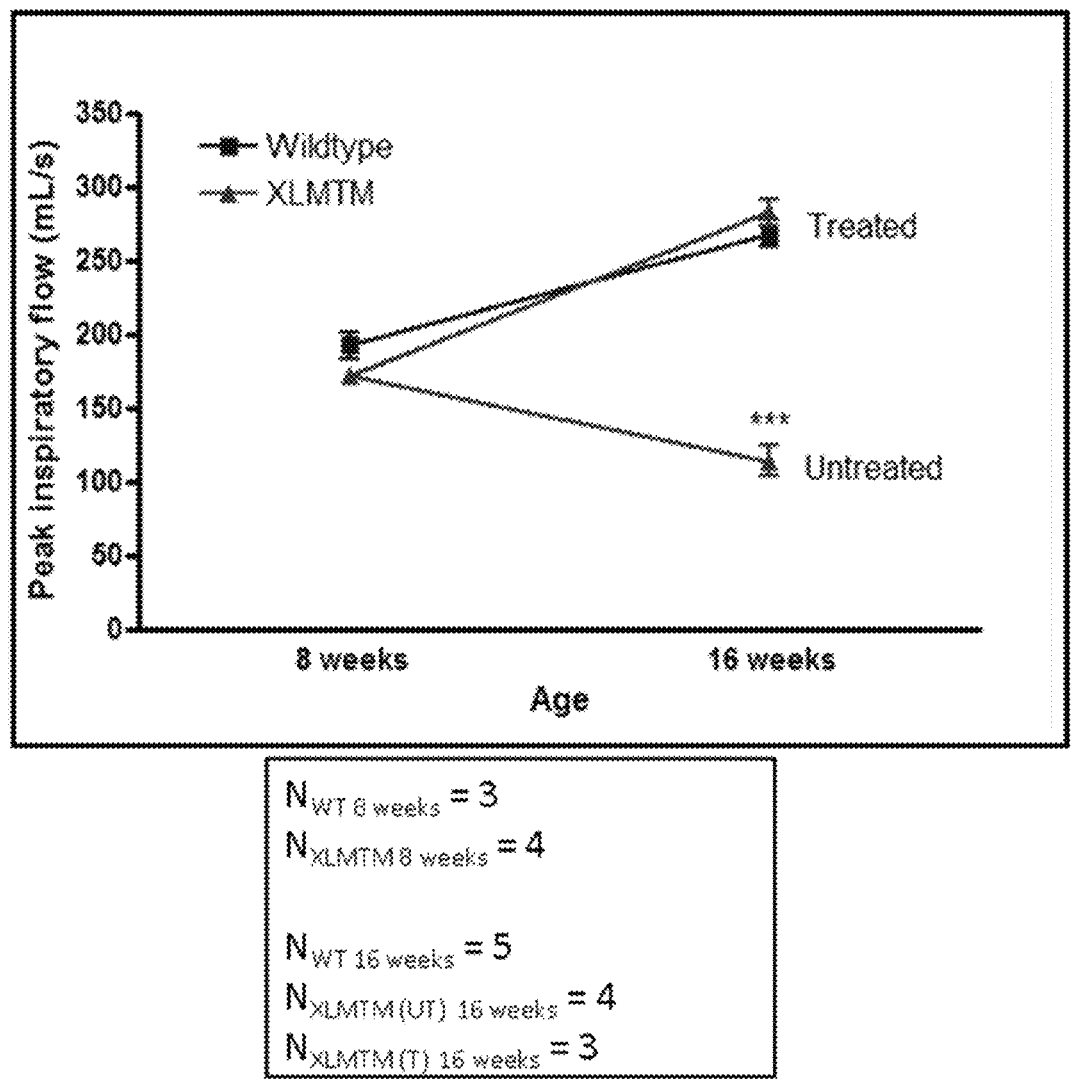
FIG. 32 is a graph depicting the results of experiments demonstrating that peak inspiratory flow improves flowing systemic delivery of AAV8-MTM1.

As shown in FIG. 30, prior to treatment, the TBFVL for XLMTM dogs is much smaller compared to normal, wild type dogs. However, 8 weeks after treatment, TBFLV in treated dogs reveal much improved function. Because quantitative analysis of TBFLV is difficult, peak inspiratory flow (PIF), was selected as a primary measure for quantifying respiratory function (FIG. 31). Shown in FIG. 32 is PIF measured at 8 week and 16 weeks of age in XLMTM dogs and their normal wild type littermates. In treated XLMTM dogs, measures are taken just prior to AAV8-MTM1 gene therapy at 8 weeks of age; 16 week measures are two months post-treatment. In untreated XLMTM dogs, 16 weeks marks the terminal end point. Significance was determined by ANOVA with Bonferroni posttest ($P<0.0001$), with untreated XLMTM PIF being significantly lower than both wild type and treated dogs. ($N_{WT}$ at 8 weeks=3, $N_{WT}$ at 16 weeks=5, $N_{XLMTM}$ at 8 weeks=4, $N_{untreated}$ XLMTM at 16 weeks=4, $N_{Treated}$ XLMTM at 16 weeks=3).

The data presented herein demonstrate that AAV8-MTM1 delivered by high pressure limb infusion results in improved respiratory muscle function in XLMTM dogs. The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating an X-linked myotubular myopathy (XLMTM) in a human in need thereof, the method comprising administering to the human a composition that increases expression of myotubularin in a muscle of the human, wherein the composition comprises an adeno-associated viral (AAV) vector comprising a nucleic acid sequence encoding a human Myotubularin 1 (MTM1) gene operably linked to a muscle specific promoter wherein the function of the diaphragm of the human is improved, as compared to the diaphragm of a human in the absence of administration of the composition, wherein strength is increased in the muscle.

2. The method of claim 1, wherein the AAV vector comprises a serotype selected from the group consisting of AAV1, AAV2, AAV3, AAV4, AAV5, AAV6, AAV7, AAV8, and AAV9.

3. The method of claim 1, wherein the composition is administered to the human systemically.

4. The method of claim 1, wherein the administration route comprises at least one selected from the group consisting of intravenous, intra-arterial, and intramuscular.

5. The method of claim 1, wherein the muscle of the human exhibits an increase in myotubularin expression for a period of up to 1 year, as compared to the muscle of a human in the absence of administration of the composition.

6. The method of claim 1, wherein the muscle of the human exhibits a sustained increase in strength for up to 6 months, as compared to the muscle of a human in the absence of administration of the composition.

7. The method of claim 1, wherein the human has a longer survival rate than a human in the absence of administration of the composition.

8. The method of claim 1, wherein the administration is selected from the group consisting of a single administration and at least two administrations.

9. A method of prolonging the survival of a human with an X-linked myotubular myopathy (XLMTM), the method comprising administering to the human a composition that increases the expression of myotubularin in a muscle of the human, wherein the composition comprises an adeno-associated viral (AAV) vector comprising a nucleic acid sequence encoding a human Myotubularin 1 (MTM1) gene operably linked to a muscle specific promoter.

10. The method of claim 9, wherein the function of the diaphragm of the human is improved, as compared to the diaphragm of a human in the absence of administration of the composition, wherein strength is increased in the muscle, and wherein survival of the human is prolonged.

11. The method of claim 9, wherein the AAV vector comprises a serotype selected from the group consisting of AAV1, AAV2, AAV3, AAV4, AAV5, AAV6, AAV7, AAV8, and AAV9.

12. The method of claim 9, wherein the composition is administered to the human systemically.

13. The method of claim 9, wherein the administration route comprises at least one selected from the group consisting of intravenous, intra-arterial, and intramuscular.

14. The method of claim 9, wherein the muscle of the human exhibits an increase in myotubularin expression for a period of up to 1 year, as compared to the muscle of the human in the absence of administration of the composition.

15. The method of claim 9, wherein the muscle of the human exhibits a sustained increase in strength for up to 6 months, as compared to the muscle of a human in the absence of administration of the composition.

16. The method of claim 9, wherein the administration is selected from the group consisting of a single administration and at least two administrations.

17. A method of treating an X-linked myotubular myopathy (XLMTM) in a human in need thereof, the method comprising administering to the human a composition that increases the expression of myotubularin in a muscle of the human, wherein the composition comprises a viral vector comprising a nucleic acid sequence encoding a human Myotubularin 1 (MTM1) gene operably linked to a muscle specific promoter.

18. The method of claim 17, wherein the muscle of the human administered the composition exhibits an increase in MTM1 expression for a period selected from the group consisting of up to 3 months, up to 6 months and up to 1 year, as compared with the muscle of a human not administered the composition.

19. The method of claim 17, wherein the viral vector is selected from the group consisting of a lentiviral vector, retroviral vector, adenoviral vector, and adeno-associated viral (AAV) vector.

20. The method of claim 19, wherein the AAV vector comprises a serotype selected from the group consisting of AAV1, AAV2, AAV3, AAV4, AAV5, AAV6, AAV7, AAV8, and AAV9.

21. The method of claim 17, wherein the composition is administered to the human systemically.

22. The method of claim 17, wherein the administration route comprises at least one selected from the group consisting of intravenous, intra-arterial, and intramuscular.

23. The method of claim 17, wherein the muscle of the human administered the composition exhibits a sustained increase in strength for up to 6 months, as compared with the muscle of a human not administered the composition.

24. The method of claim 17, wherein the human administered the composition has a longer survival rate than a human not administered the composition.

25. The method of claim 17, wherein the function of the diaphragm of the human administered the composition is improved, as compared with the diaphragm of a human in the absence of administration of the composition.

26. The method of claim 17, wherein the administration is selected from the group consisting of a single administration and at least two administrations.

27. A method of treating an X-linked myotubular myopathy (XLMTM) in a human in need thereof, the method comprising administering to the human a composition that increases the expression of myotubularin in a muscle of the human, wherein the composition comprises a viral vector comprising a nucleic acid sequence encoding a human Myotubularin 1 (MTM1) gene operably linked to a muscle specific promoter.

28. The method of claim 27, wherein the function of the diaphragm of the human is improved, as compared to the diaphragm of a human in the absence of administration of the composition, wherein strength is increased in the muscle.

29. The method of claim 27, wherein the muscle of the human administered the composition exhibits an increase in MTM1 expression for a period selected from the group consisting of up to 3 months, up to 6 months and up to 1 year, as compared with the muscle of a human not administered the composition.

30. The method of claim 27, wherein the composition is administered to the human systemically.

31. The method of claim 27, wherein the viral vector is selected from the group consisting of a lentiviral vector, retroviral vector, adenoviral vector, and adeno-associated viral (AAV) vector.

32. The method of claim 31, wherein the AAV vector comprises a serotype selected from the group consisting of AAV1, AAV2, AAV3, AAV4, AAV5, AAV6, AAV7, AAV8, and AAV9.

33. The method of claim 27, wherein the administration route comprises at least one selected from the group consisting of intravenous, intra-arterial, and intramuscular.

34. The method of claim 27, wherein the administration is selected from the group consisting of a single administration and at least two administrations.

35. A method of prolonging the survival of a human with an X-linked myotubular myopathy (XLMTM), the method comprising administering to the human a composition that increases the expression of myotubularin in a muscle of the human, wherein the composition comprises a viral vector comprising a nucleic acid sequence encoding a human Myotubularin 1 (MTM1) gene operably linked to a muscle specific promoter.

36. The method of claim 35, wherein the composition is administered to the human systemically.

37. The method of claim 35, wherein the function of the diaphragm of the human is improved, as compared to the diaphragm of a human in the absence of administration of the composition, wherein strength is increased in the muscle, and wherein survival of the human is prolonged.

38. The method of claim 35, wherein the viral vector is selected from the group consisting of a lentiviral vector, retroviral vector, adenoviral vector, and adeno-associated viral (AAV) vector.

39. The method of claim 38, wherein the AAV vector comprises a serotype selected from the group consisting of AAV1, AAV2, AAV3, AAV4, AAV5, AAV6, AAV7, AAV8, and AAV9.

40. The method of claim 35, wherein the administration route comprises at least one selected from the group consisting of intravenous, intra-arterial, and intramuscular.

41. The method of claim 35, wherein the muscle of the human administered the composition exhibits an increase in MTM1 expression for a period selected from the group consisting of up to 3 months, up to 6 months and up to 1 year, as compared with the muscle of a human not administered the composition.

42. The method of claim 35, wherein the muscle of the human exhibits a sustained increase in strength for up to 6 months, as compared to the muscle of a human in the absence of administration of the composition.

43. The method of claim 35, wherein the administration is selected from the group consisting of a single administration and at least two administrations.

44. A method of restoring normal muscle function in a human with an X-linked myotubular myopathy (XLMTM), the method comprising administering to the human a composition that increases the expression of myotubularin in a muscle of the human, wherein the composition comprises a viral vector comprising a nucleic acid sequence encoding an Myotubularin 1 (MTM1) gene operably linked to a muscle specific promoter.

45. The method of claim 44, wherein the muscle of the human administered the composition exhibits an increase in MTM1 expression to achieve a level similar to the MTM1 expression in the muscle of a healthy human.

46. The method of claim 44, wherein the viral vector is selected from the group consisting of a lentiviral vector, retroviral vector, adenoviral vector, and adeno-associated viral (AAV) vector.

47. The method of claim 46, wherein the AAV vector comprises a serotype selected from the group consisting of AAV1, AAV2, AAV3, AAV4, AAV5, AAV6, AAV7, AAV8, and AAV9.

48. The method of claim 44, wherein the composition is administered to the human systemically.

49. The method of claim 44, wherein the administration route comprises at least one selected from the group consisting of intravenous, intra-arterial, and intramuscular.

50. The method of claim 44, wherein the muscle of the human administered the composition exhibits sustained increase in strength to reach a level similar to the muscle of a healthy human.

51. The method of claim 44, wherein the function of the diaphragm of the human administered the composition exhibits sustained improvement to reach a level similar to the function of the diaphragm of a healthy human.

52. The method of claim 44, wherein the administration is selected from the group consisting of a single administration and at least two administrations.

53. A pharmaceutical composition comprising a viral vector comprising a nucleic acid sequence encoding an Myotubularin 1 (MTM1) gene operably linked to a muscle specific promoter.

54. The pharmaceutical composition of claim 53, wherein the viral vector is selected from the group consisting of a lentiviral vector, retroviral vector, adenoviral vector, and adeno-associated viral (AAV) vector.

55. The pharmaceutical composition of claim 53, wherein the AAV vector comprises a serotype selected from the group consisting of AAV1, AAV2, AAV3, AAV4, AAV5, AAV6, AAV7, AAV8, and AAV9.

56. The pharmaceutical composition of claim 53, wherein the muscle specific promoter is a desmin promoter.

* * * * *